(12) United States Patent
Kimura

(10) Patent No.: US 8,975,374 B2
(45) Date of Patent: *Mar. 10, 2015

(54) PHARMACEUTICAL COMPOSITION COMPRISING ANTI-HB-EGF ANTIBODY AS ACTIVE INGREDIENT

(75) Inventor: Naoki Kimura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 419 days.

This patent is subject to a terminal disclaimer.

(21) Appl. No.: 12/584,360

(22) Filed: Sep. 3, 2009

(65) Prior Publication Data

US 2010/0266502 A1 Oct. 21, 2010

Related U.S. Application Data

(63) Continuation-in-part of application No. 12/311,960, filed as application No. PCT/JP2007/070487 on Oct. 19, 2007.

(30) Foreign Application Priority Data

Oct. 20, 2006 (JP) ................................. 2006-286824
Apr. 16, 2007 (JP) ................................. 2007-107207

(51) Int. Cl.
*C07K 16/00* (2006.01)

(52) U.S. Cl.
USPC ..................................... 530/387.1; 424/130.1

(58) Field of Classification Search
None
See application file for complete search history.

(56) References Cited

U.S. PATENT DOCUMENTS

| | | | |
|---|---|---|---|
| 6,342,219 B1 * | 1/2002 | Thorpe et al. ............... | 424/145.1 |
| 2005/0272634 A1 | 12/2005 | Bahlmann et al. | |
| 2010/0061933 A1 | 3/2010 | Kimura | |
| 2010/0273988 A1 | 10/2010 | Kimura | |

FOREIGN PATENT DOCUMENTS

| | | |
|---|---|---|
| EP | 2 039 704 | 3/2009 |
| EP | 2 078 731 | 7/2009 |
| EP | 2 093 237 | 8/2009 |
| WO | WO 2005066348 A2 | 7/2005 |
| WO | 2007/142277 | 12/2007 |
| WO | WO 2007/142277 | 12/2007 |
| WO | 2008/047914 | 4/2008 |
| WO | 2008/047925 | 4/2008 |
| WO | WO 2008/047914 A1 | 4/2008 |
| WO | WO 2008148884 A1 | 12/2008 |
| WO | WO 2009/040134 | 4/2009 |
| WO | 2009/072628 | 6/2009 |

OTHER PUBLICATIONS

Toki et al. (J. of Cellular Physiology, vol. 202:839-848, 2005).*
Wang et al. (Oncogene, vol. 21, pp. 2584-2592, 2002).*
Iwamoto, Ryo et al., "Heparin-binding EGF-like growth factor and ErbB signaling is essential for heart function," *Proc. Natl. Acad. Sci. USA*,; vol. 100, No. 6, (2003), pp. 3221-3226.
Abraham, Judith A., "Heparin-Binding EGF-Like Growth Factor: Characterization of Rat and Mouse cDNA Clones, Protein Domain Conservation Across Species, and Transcript Expression in Tissues," *Biochemical and Biophysical Research Communications*, vol. 190, No. 1, (1993), pp. 125-133.
Davids-Fleischer, Karen M et al., Structure and Function of Heparin-Binding EGF-like Growth Factor (HB-EGF), *Frontiers in Bioscience*, 3, (1998), pp. 288-299.
Raab, Gerhard et al., "Heparin-Binding EGF-like Growth Factor," *Biochemica et Biophysica Acta*, 1333, (1997), pp. F179-F199.
Yamazaki, Satoru et al., "Mice with Defects in HB-EGF Ectodomain Shedding Show Severe Developmental Abnormalities," *J Cell Biol*, vol. 163, No. 3, (2003), pp. 469-475.
Ongusaha, Pat P. et al., "HB-EGF Is a Potent Inducer of Tumor Growth and Angiogenesis," *Cancer Research*, 64, (2004), pp. 5283-5290.
Iwamoto, Ryo et al., "Heparin-binding EGF-like Growth Factor, Which Acts as the Diphtheria Toxin Receptor, Forms a Complex with Membrane Protein DRAP27/CD9, which Up-Regulates Functional Receptors and Diphtheria Toxin Sensitivity," *EMBO J.*, vol. 13, No. 10, (1994), pp. 2322-2330.
Naglich, Joseph G. et al., "Expression Cloning of a Diphtheria Toxin Receptor: Identity with a Heparin-Binding EGF-like Growth Factor Precursor," *Cell*, vol. 69, (1992), pp. 1051-1061.
Iwamoto, Ryo et al., "Contact-Dependent Growth Inhibition and Apoptosis of Epidermal Growth Factor (EGF) Receptor-Expressing Cells by the Membrane-Anchored Form of Heparin-Binding EGF-like Growth Factor," *J. Biol. Chem.*, vol. 274, No. 36, (1999), pp. 25906-25912.
Miyamoto, Shingo et al., "Heparin-Binding Epidermal Growth Factor-like Growth Factor as a Novel Targeting Molecule for Cancer Therapy," *Cancer Sci.*, vol. 97, No. 5, (2006), pp. 341-347.
Blotnick, Sully et al., "T Lymphocytes Synthesize and Export Heparin-Binding Epidermal Growth Factor-like Growth Factor and Basic Fibroblast Growth Factor, Mitogens for Vascular Cells and Fibroblasts: Differential Production and Release by CD4+ and CD8+ T Cells," *Proc. Natl. Acad. Sci. USA*, vol. 91, (1994) 2890-2894.

(Continued)

*Primary Examiner* — Laura B Goddard
(74) *Attorney, Agent, or Firm* — Sterne, Kessler, Goldstein & Fox P.L.L.C.

(57) ABSTRACT

An anti-HB-EGF antibody having an internalizing activity is disclosed. A cytotoxic substance is preferably bound to the anti-HB-EGF antibody of the present invention. Also provided are an anti-cancer agent and a cell proliferation inhibitor, which comprise the antibody of the present invention as an active ingredient, a method of treating cancer and a method of diagnosing cancer, which comprise the administration of the antibody of the present invention. Cancers that can be treated by the anti-cancer agent of the present invention include pancreatic cancer, liver cancer, esophageal cancer, melanoma, colorectal cancer, gastric cancer, ovarian cancer, uterine cervical cancer, breast cancer, bladder cancer, brain tumors, and hematological cancers.

10 Claims, 29 Drawing Sheets

(56) References Cited

OTHER PUBLICATIONS

Hashimoto, Koji et al., "Heparin-Binding Epidermal Growth Factor-like Growth Factor is an Autocrine Growth Factor for Human Keratinocytes," *J. Biol. Chem.*, vol. 269, No. 31, (1994), pp. 20060-20066.

Mishima, Kazuhiko et al., "Heparin-Binding Epidermal Growth Factor-like Growth Factor Stimulates Mitogenic Signaling and is Highly Expressed in Human Malignant Gliomas," *Acta Neurophathol.*, 96, (1998), pp. 322-328.

Wang, Yue Dan, "Cooperation Between Heparin-Binding EGF-like Growth Factor and Interleukin-6 in Promoting the Growth of Human Myeloma Cells," *Oncogene*, 21, (2002), pp. 2584-2592.

Miyamoto, Shingo, "Heparin-Binding EGF-like Growth Factor is a Promising Target for Ovarian Cancer Therapy," *Cancer Res.*, 64, (2004) pp. 5720-5727.

Buzzi, Silvio et al., "CRM197 (nontoxic diphtheria toxin): Effects on Advanced Cancer Patients," *Cancer Immunol Immunother*, 53, (2004), pp. 1041-1048.

E. Tagliabue et al. "Selection of Monoclonal Antibodies which Induce Internalization and Phosphorylation of p185$^{HER2}$ and Growth Inhibition of Cells with HER2/NEU Gene Amplification," *Int. J. Cancer*, 47(6), 1991, pp. 933-937.

C.J. Wikstrand et al. "Cell Surface Localization and Density of Tumor associated Variant of the Epidermal Growth Factor Receptor, EGFRvIII," *Cancer Research*, 57(18), 1997, pp. 4130-4140.

International Preliminary Report on Patentability and Written Opinion of the International Searching Authority issued in corresponding International Patent Application No. PCT/JP2007/070487 dated Apr. 19, 2009.

S. Blotnick et al., "T lymphocytes synthesize and export heparin-binding epidermal growth-factor like growth factor and basic fibroblast growth factor, mitogens for vascular cells and fibroblasts: Differential production and release by CD4$^+$ and CD8$^+$ T Cells," *Proc Natl. Acad. Sci* USA, 91,1994, pp. 2890-2894.

K. Hashimoto et al. "Heparin-binding Epidermal Growth Factor-like Growth Factor is an Autocrine Growth Factor for Human Keratinocytes," *The Journal of Biological Chemistry*, 269(31), 1994, pp. 20060-20066.

Y. D. Wang et al. "Cooperation between heparin-binding EGF-like growth factor and interleukin-6 in promoting the growth of human myeloma cells," *Oncogene*, 21, 2002, pp. 2584-2592.

Miyamoto, S., et al., "Potential for molecularly targeted therapy against epidermal growth factor receptor ligands", Anticancer Research, Mar. 2009, vol. 29, No. 3, pp. 823-830.

International Search Report issued in connection with corresponding International Application No. PCT/JP2010/005074.

Poul, Marie-Alix et al., "Selection of Tumor-Specific Internalizing Human Antibodies from Phage Libraries," *Journal of Molecular Biology*, vol. 301 (2000), pp. 1149-1161.

International Search Report issued in connection with corresponding International Application No. PCT/JP2009/003915.

Office Action, dated Aug. 2, 2011, issued in connection with corresponding Russian Patent Application No. 2008152746/15(069532).

Huang, P. P., et al., "Autologous Transplantation of Peripheral Blood Stem Cells as an Effective Therapeutic Approach for Severe Arteriosclerosis Obliterans of Lower Extremities", Thrombosis and Haemostasis, Dec. 2003, vol. 91, No. 3, pp. 606-609.

Office Action from the Chinese Patent Office dated Sep. 7, 2011, in connection with corresponding Chinese Application No. 200780045144.7.

Goishi, K., et al., "Phorbol Ester Induces the Rapid Processing of Cell Surface Heparin-binding EGF-like Growth Factor: Conversion from Juxtacrine to Paracrine Growth Factor Activity", Molecular Biology of the Cell, vol. 6, pp. 967-980; Aug. 31, 1995.

Von Mehren, M., et al., "Monoclonal Antibody Therapy for Cancer", Annu. Rev. Med., vol. 54, pp. 343-369; Feb. 28, 2003.

Office Action from the Australian Patent Office dated Oct. 28, 2011, in connection with corresponding Australian Application No. 2007311957.

Wang, Y. D., et al., "Cooperation Between Heparin-binding EGF-Like Growth Factor and Interleukin-6 in Promoting the Growth of Human Myeloma Cells", *Oncogene*, 2002, vol. 21, pp. 2584-2592.

Blotnick, S., et al., "T lymphocytes synthesize and export heparin-binding epidermal growth factor-like growth factor and basic fibrolast growth factor, mitogens for vascular cells and fibroblasts: Differential production and release by CD4+ and CD8+ T cells", *Proc. Nati. Acad. Sci. USA*, Apr. 1994, vol. 91, pp. 2890-2894.

Hashimoto, K. et al., "Heparing-binding Epidermal Growth Factor-like Growth Factor Is an Autocrine Growth Factor for Human Keratinocytes", *Journal of Biological Chemistry*, vol. 269, No. 31, pp. 20060-20066; Aug. 5, 1994.

Nielsen, U. B., et al., "Internalizing Antibodies and Targeted Cancer Therapy: Direct Selection from Phage Display Libraries", *Pharmaceutical Science & Technology Today*, vol. 3, No. 8, pp. 282-291; Aug. 2000.

Asakura, Masanori, et al. "Cardiac hypertrophy is inhibited by antagonism of ADAM12 proceeding of HB-EGF: Metalloproteinase inhibitors as a new therapy," Nature Medicine, vol. 8, No. 1, Jan. 2002, pp. 35-40.

Chinese Office Action, dated Aug. 22, 2012, issued in connection corresponding Chinese Application No. 200780045023.2.

International Search Report, dated Jun. 28, 2012, issued in connection with corresponding European Application No. 07830221.3.

International Search Report, dated May 30, 2012, issued in connection with corresponding European Application No. 07830200.7.

Yagi et al. (British Journal of Cancer, vol. 92, pp. 1737-1745, Apr. 2005).

Rudikoff et al. Proc Natl Acad Sci USA 1982 vol. 79 p. 1979.

MacCallum et al. J. Mol. Bioi. (1996) 262,732-745.

Pascalis et al. The Journal of Immunology (2002) 169, 3076-3084.

Casset et al. BBRC 2003, 307:198-205.

Vajdos et al. J. Mol. Bioi. (2002) 320, 415-428.

Chen et al. J. Mol. Bio. (1999) 293, 865-881.

Wu et al. J. Mol. Bioi. (1999) 294, 151-162.

Padlan et al. PNAS 1989, 86:5938-5942.

Lamminmaki et al. JBC 2001, 276:36687-36694.

Y. Myoken et al., "Monoclonal Antibodies Against Heparin-Binding Growth Factor-1: Neutralization of Biological Activity and Recognition of Specific Amino Acid Sequences", *Biochemical and Biophysical Research Communications*, 197(3), 1993, pp. 1450-1457.

International Preliminary Report on Patentability and Written Opinion of the International Searching Authority dated Apr. 30, 2009, issued in connection with International Patent Application No. PCT/JP2007/070466, which corresponds to commonly owned U.S. Appl. No. 12/311,950.

International Search Report, dated Sep. 28, 2010, issued in connection with International Patent Application No. PCT/JP2010/005074, which corresponds to commonly owned U.S. Appl. No. 12/311,960.

White et al. (2001, Ann. Rev. Med., 2001, 52:125-145).

U.S. Appl. No. 13/391,171, filed May 3, 2012, Kimura.

Office Action dated Feb. 6, 2013, from the Chinese Patent Office concerning the corresponding Chinese Application No. 200780045144.7.

Introduction of Immunology,1999, pp. 49, table 3-3 and pp. 224, section 2.

Hamaoka, M., et al. "Anti-human HB-EGF monoclonal antibodies inhibiting ectodomain shedding of HB-EGF and diphtheria toxin binding." J. Biochem. (2010) vol. 148 (1) pp. 55-69.

Murata, T., et al. "HB-EGF and PDGF Mediate Reciprocal Interactions of Carcinoma Cells with Cancer-Associated Fibroblasts to Support Progression of Uterine Cervical Cancers." Cancer Res. (2011) vol. 71, pp. 6633-6642.

Murata, T., et al. "HB-EGF and PDGF Mediate Reciprocal Interactions of Carcinoma Cells with Cancer-Associated Fibroblasts to Support Progression of Uterine Cervical Cancers." Cancer Res. (2011) vol. 71, pp. 6633-6642. Supplementary Materials and Methods.

Kusano, et al. "Immunocytochemical study on internalization of anti-carbohydrate monoclonal antibodies." Anticancer Research (1993), vol. 13, pp. 2207-2212.

Japanese Written Interrogation directed to related Japanese Patent Application No. 2008-539888, Appeal No. 2013-12560, mailed May 27, 2014; 4 pages.

(56) References Cited

OTHER PUBLICATIONS

Yu at al., "CD44 anchors the assembly of matrilysin/MMP-7 with heparin-binding epidermal growth factor precursor and ErbB4 and regulates female reproductive organ remodeling," *Genes & Development.* 16(3): 307-323; (Feb. 2002).

Japanese Office Action, dated Nov. 6, 2012, issued in connection with corresponding Japanese Application No. 2008-539894.

Tee Fern Khong, et al. Kidney International, 2000, vol. 58, pp. 1098-1107.

Peter J Gaillard, et al. International Congress Series, Apr. 2005, vol. 1277, pp. 185-198.

Japanese Office Action, dated Nov. 6, 2012, issued in connection with corresponding Japanese Application No. 2008-539888.

"Funakoshi General Catalog of Antibody 2004 Part I Antibody", Funakoshi Co., 2004, p. 405, xiii.

Office Action issued on Nov. 21, 2012, in connection with corresponding European Patent Application No. 07830200.7.

McKay Brown, et al.: "Tolerance to single, but not multiple, amino add replacements in antibody V-H CDR2: A means of minimizing B cell wastage from somatic hypermutation?", The Journal of Immunology, The American Association of Immunologists, US, vol. 156, No. 9, Jan. 1, 1996, pp. 3285-3291.

Office Action issued on May 30, 2013 for commonly-owned U.S. Appl. No. 12/311,950.

F.W. Falkenberg et al., "Polyclonal Antibodies as Reagents in Biochemical and in Clinical-Chemical Analysis," J. Clin. Chem. Clin. Biochem., vol. 22, No. 12, 1984, pp. 867-882.

Extended European Search Report, dated May 6, 2013, from the European Patent Office concerning the corresponding European Application No. 10809728.8.

Collet TA , et al. "A binary plasmid system for shuffling combinatorial antibody libraries." Proc. Natl. Acad. Sci. USA vol. 89: pp. 10026-10030 (1992).

\* cited by examiner

【Fig. 1】
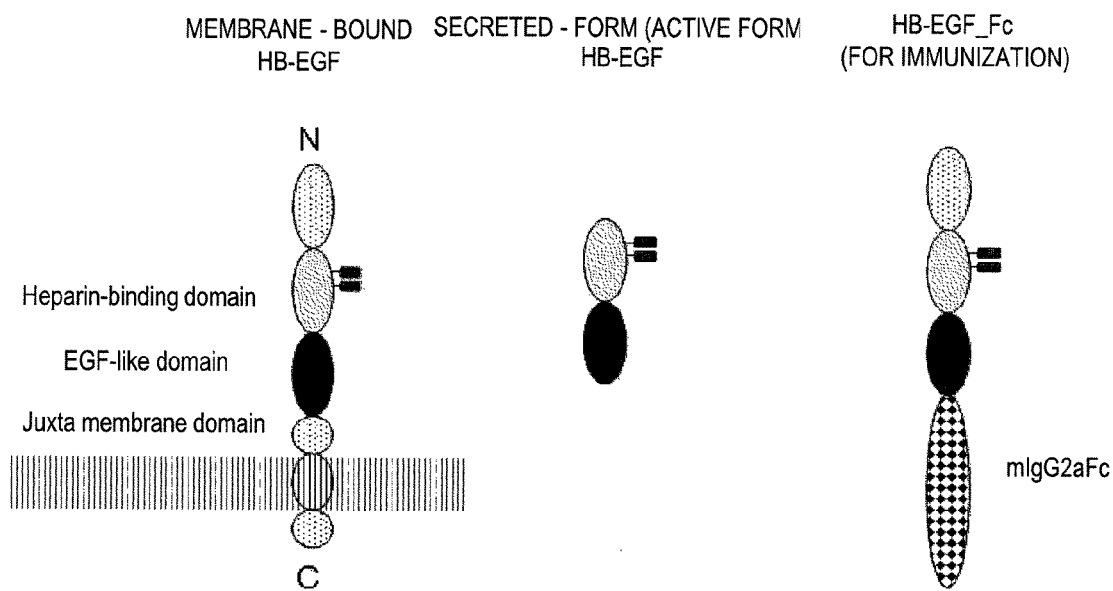
【Fig. 2a】
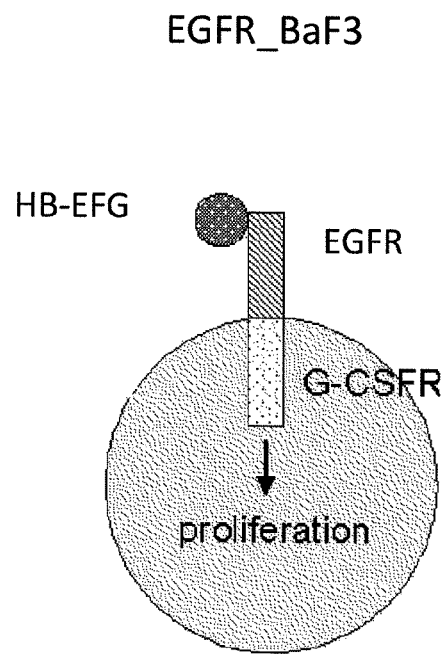

【Fig. 2b】
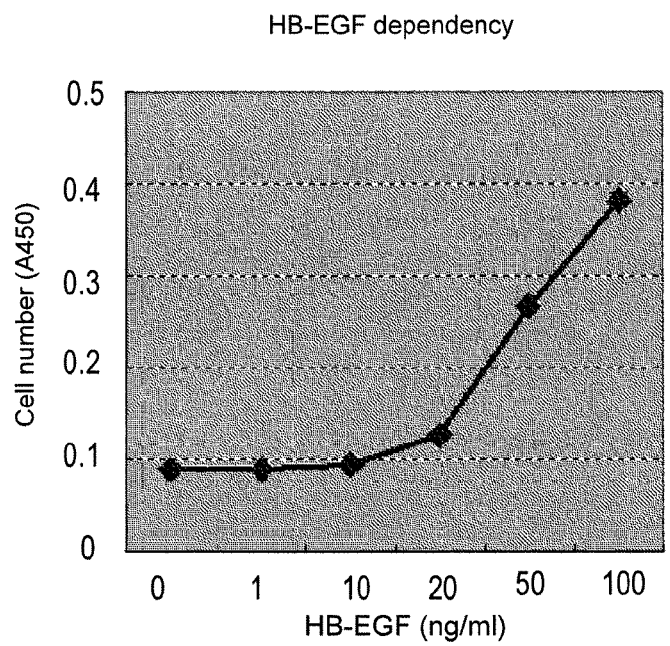
【Fig. 3a】
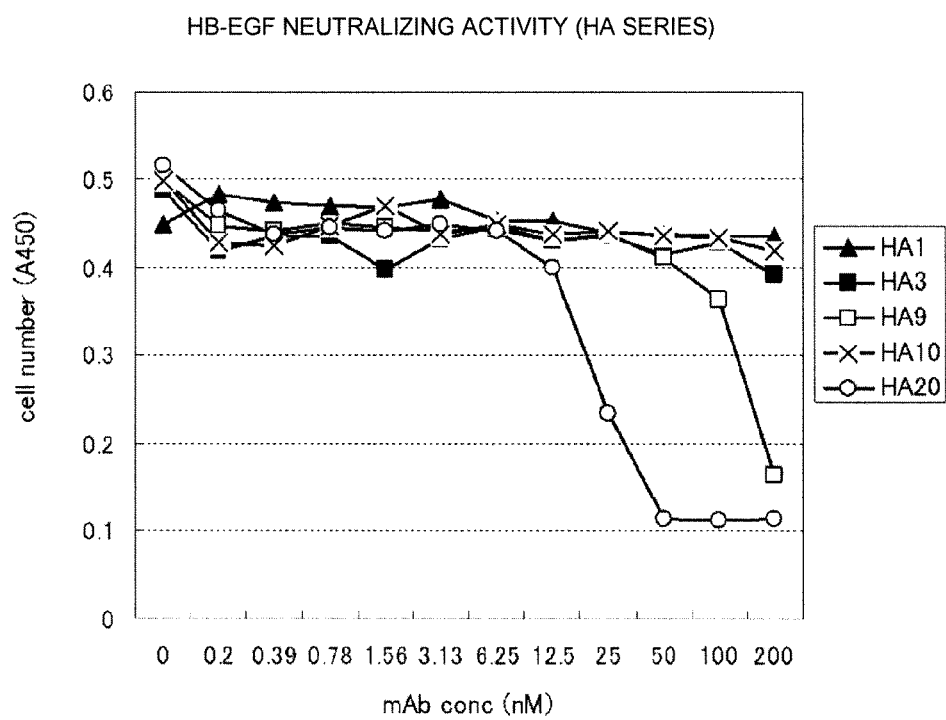

[Fig. 3b]
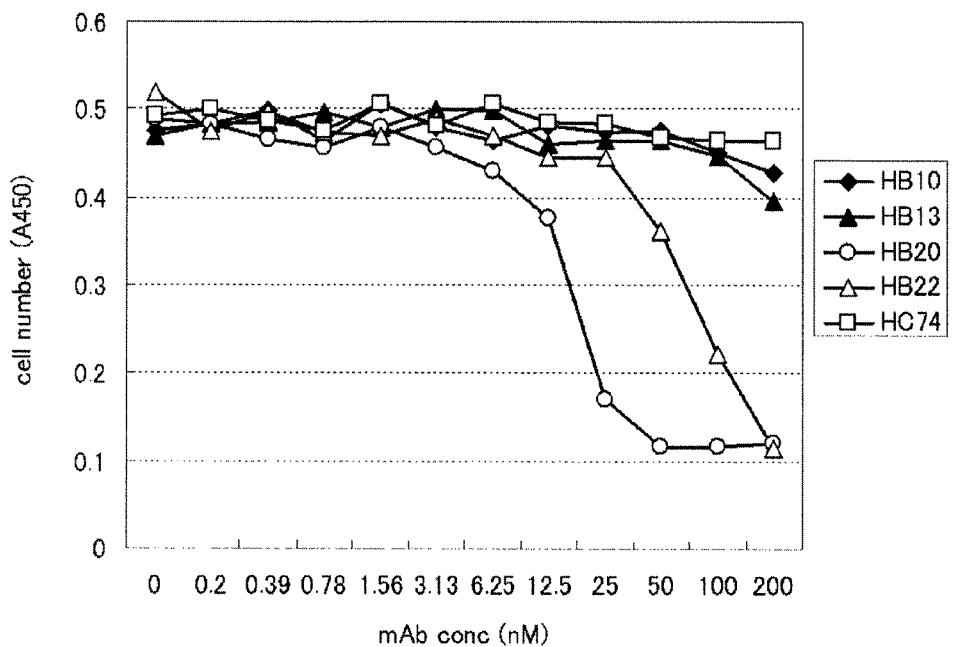
[Fig. 3c]
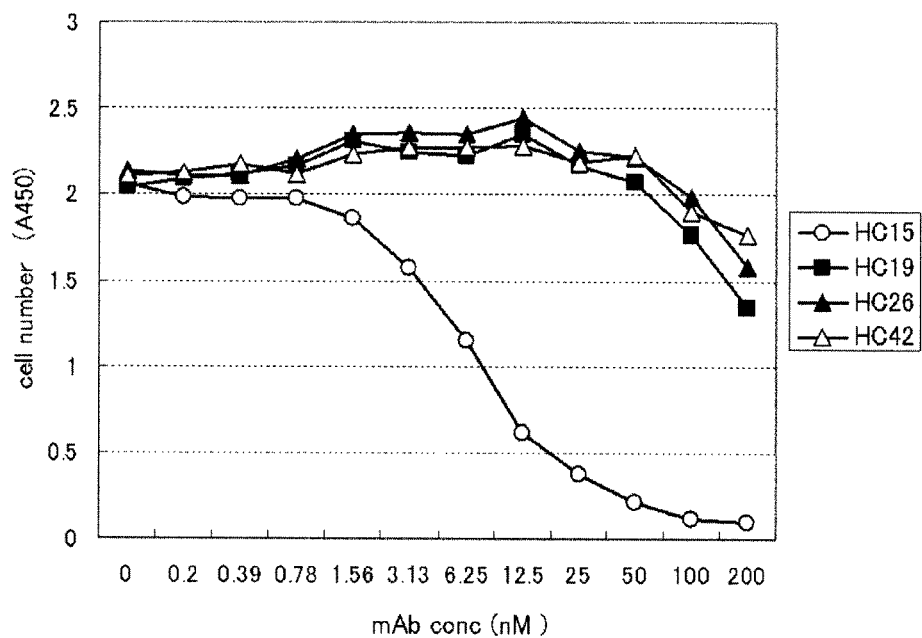

```
        VH Segments
        FR1                                       CDR1    FR2             CDR2
        ---------1---------2---------3----- -----4---------- 5----------6-----
        12345678901234567890123456789 0     12345AB 67890123456789  012A3456789012345
HA20    QVQLQQPGAELVKPGASVKLSCKAS            GYTFT   SYWMH    WVKQRPGQGLE WIG EINPSNGRTNYNEKFKS
HB20    QVQLKESGPGLVAPSQSLSITCTVS            GFSLT   GYGIN    WVRQPPGKGLE WLG MIW-GDGSADYNSALKS
HC15    EVQLQQSGPELVKPGASVKISCKAS            GYSFT   GYYMH    WVKQSPEKRLE WIG EINPRTGITTYNQKFKA
HE39_VH VQLQQSGPELMKPGASVKMSCKAS             GYIFT   DYYMN    WVKQSHGKSLE WIG RVNPNNGGTSYSQKFKD JH Segments
        FR3                                     CDR3
        ----7---------8-------------9----  ----10------------- -----11----
        6789012345678901 2abc345678901234  567890ABCDEFGHIJK12 35678901234
HA20    KATLTVDKSSSTAYMQLSSLTSEDSAVYYCVW   SLFDY-------------- WGQGTTLTVSS
HB20    RLSIRKDNSKSQVFLEMNSLQTDDTARYYCAR   GDYYGYRFSY---------- WGQGTLVTVSA
HC15    KATLTVDKSSSTAYMQLKSLTSEDSAVYYCAR   VGSSGPFTY----------- WGQGTLVTVSA
HE39_VH KATLTVDKSLNTAYMQVNSLTSEDSAVYYCAR   IYYGGSD             WGQGTTLTVSS
```

VL

```
          VK Segments
          FR1                                    CDR1             FR2             CDR2
          ---------1---------2----  -----3----------    -----4---------- 5------
          12345678901234567890123   45678901ABCDE234    567890123456789  0123456
HA20      EIVLTQSPTTMAASPGEKITITC   SASSSISSNYLH        WYQQKPGFSPKLLIY  RTSNLAS
HB20      NIMLTQSPSSLAVSAGEKVTMSC   KSSQSVLYSSNQKNFLA   WYQQKPGQSPKLLIY  WASTRES
HC15      DIVMTQSPSSLSVSAGDKVTMSC   KSSQSLLNSRNQKNYLA   WYQQKPWQPPKLLIY  GASTRES
HE39_VL-1 EIVMTQTPLSLSVTIGQPASISC   KSSQSLLYTTGKTYLN    WLQQRPGQAPKHLMY  QVSKLVP JK Segments
          FR3                                         CDR3                FR4
          ---6---------7---------8--------   -9-------------     ---10-----
          78901234567890123456789012345678   9012345ABCDEF67     8901234567
HA20      GVPARFSGSGSGTSYSLTIGTMEAEDVATYYC   QQGSSIPFT           FGSGTKLEIK
HB20      GVPDRFAGSGSGTDFTLTISSVQTEDLAVYYC   HQYLSSYT            FGGGTKLEIK
HC15      GVPDRFTGSGSGTDFTLTISSVQAEDLAVYYC   QNDYSYPFT           FGTGTKLEIK
HE39_VL-1 GIPDRFSGSGSETDFTLKISRVEAEDLGVYYC   LQGTYYPHT           FGSGTKLEIK
```

Figure 4B

| Antibody | Chain | Variable Region | Nucleotide Sequence (SEQ ID NO) | Amino Acid Sequence (SEQ ID NO) |
|---|---|---|---|---|
| HA20 | H | Full Length (aa1-19 is signal) | 37 | 38 |
| | | CDR1 | 1 | 2 |
| | | CDR2 | 3 | 4 |
| | | CDR3 | 5 | 6 |
| HA20 | L | Full Length (aa1-18 is signal) | 39 | 40 |
| | | CDR1 | 7 | 8 |
| | | CDR2 | 9 | 10 |
| | | CDR3 | 11 | 12 |
| HB20 | H | Full Length (aa1-19 is signal) | 41 | 42 |
| | | CDR1 | 13 | 14 |
| | | CDR2 | 15 | 16 |
| | | CDR3 | 17 | 18 |
| HB20 | L | Full Length (aa1-20 is signal) | 43 | 44 |
| | | CDR1 | 19 | 20 |
| | | CDR2 | 21 | 22 |
| | | CDR3 | 23 | 24 |
| HC15 | H | Full Length (aa1-19 is signal) | 45 | 46 |
| | | CDR1 | 25 | 26 |
| | | CDR2 | 27 | 28 |
| | | CDR3 | 29 | 30 |
| HC15 | L | Full Length (aa1-20 is signal) | 47 | 48 |
| | | CDR1 | 31 | 32 |
| | | CDR2 | 33 | 34 |
| | | CDR3 | 35 | 36 |

[Fig. 5]
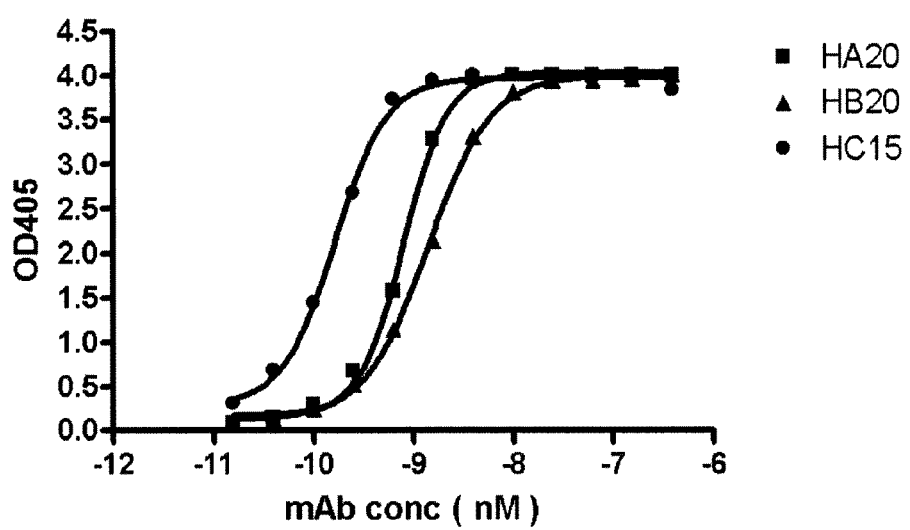

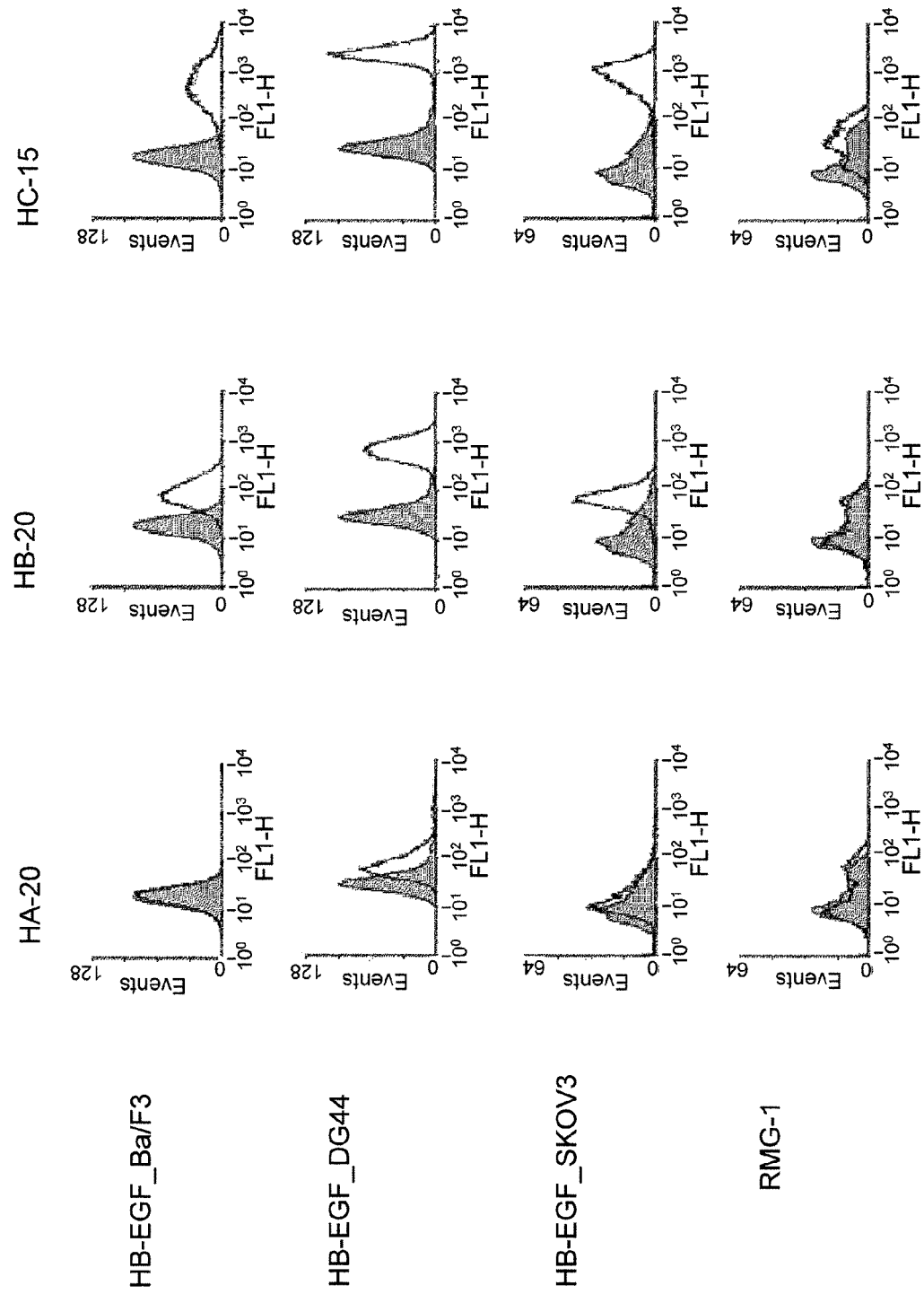
[Fig. 6]

[Fig. 7]
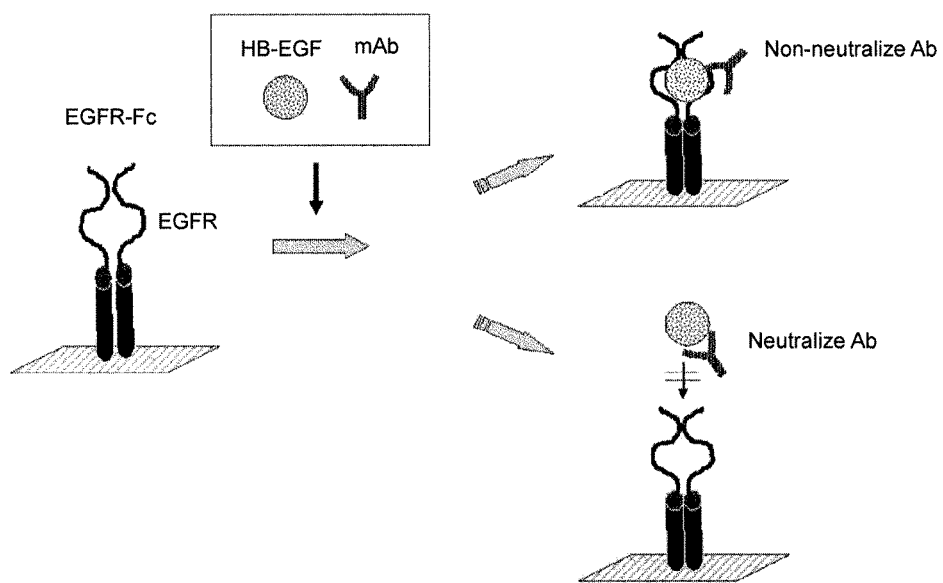
[Fig. 8]
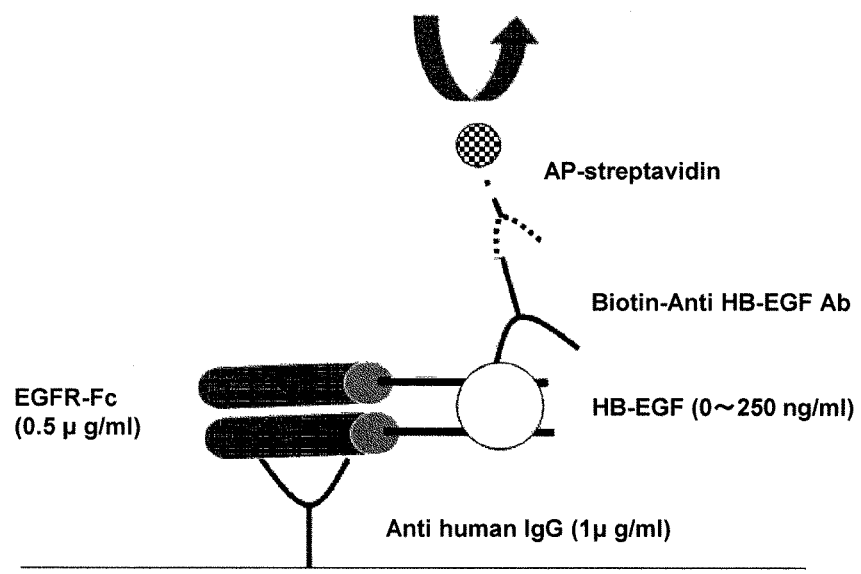

[Fig. 9]
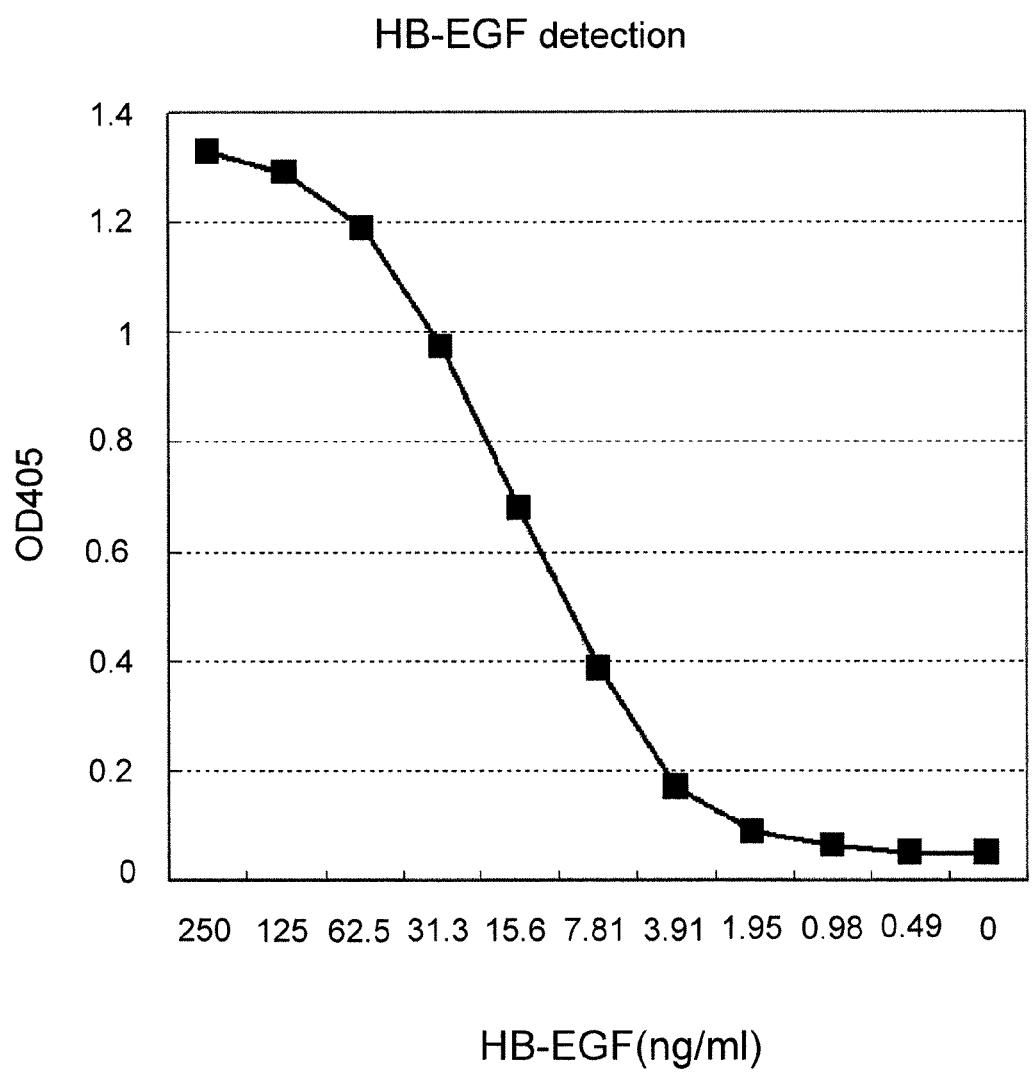

[Fig. 10]
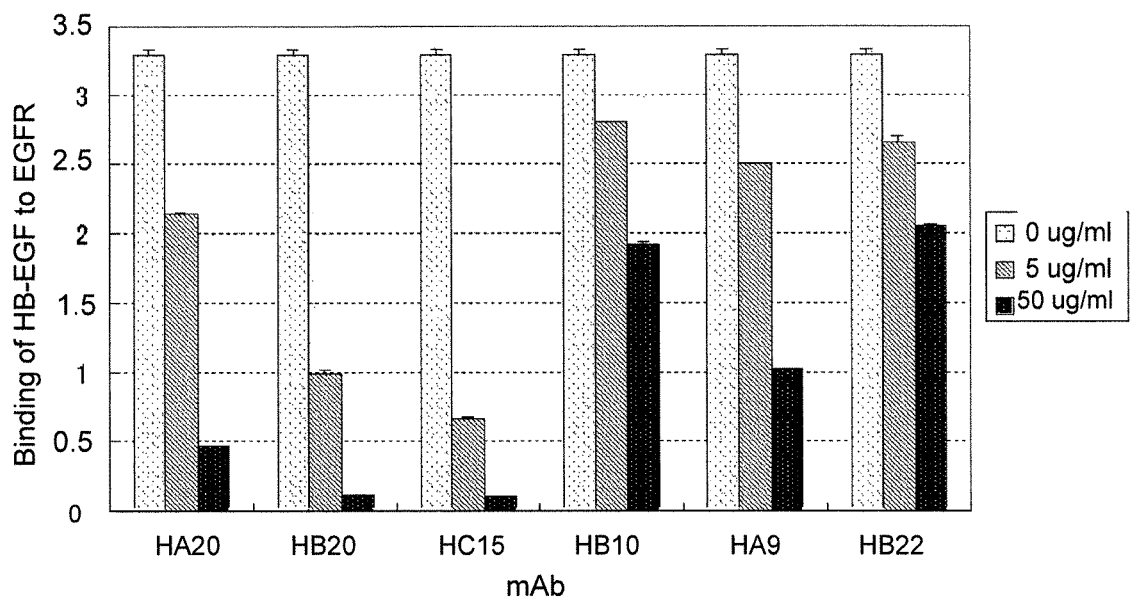
[Fig. 11]
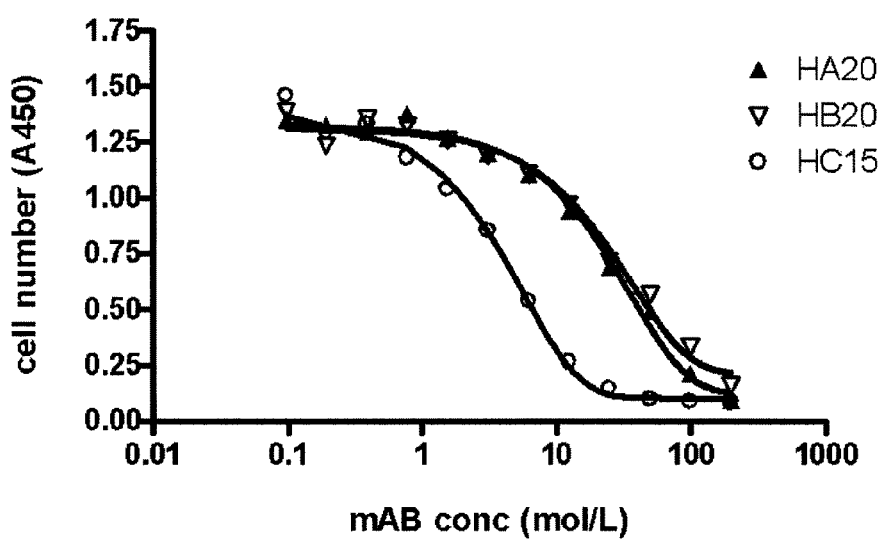

[Fig. 12a]
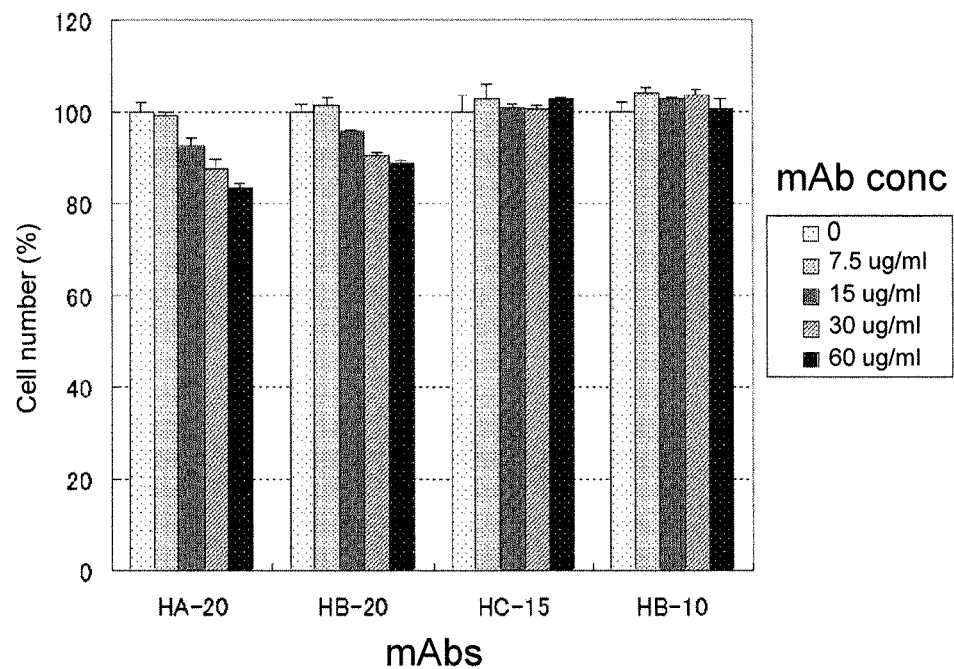
[Fig. 12b]
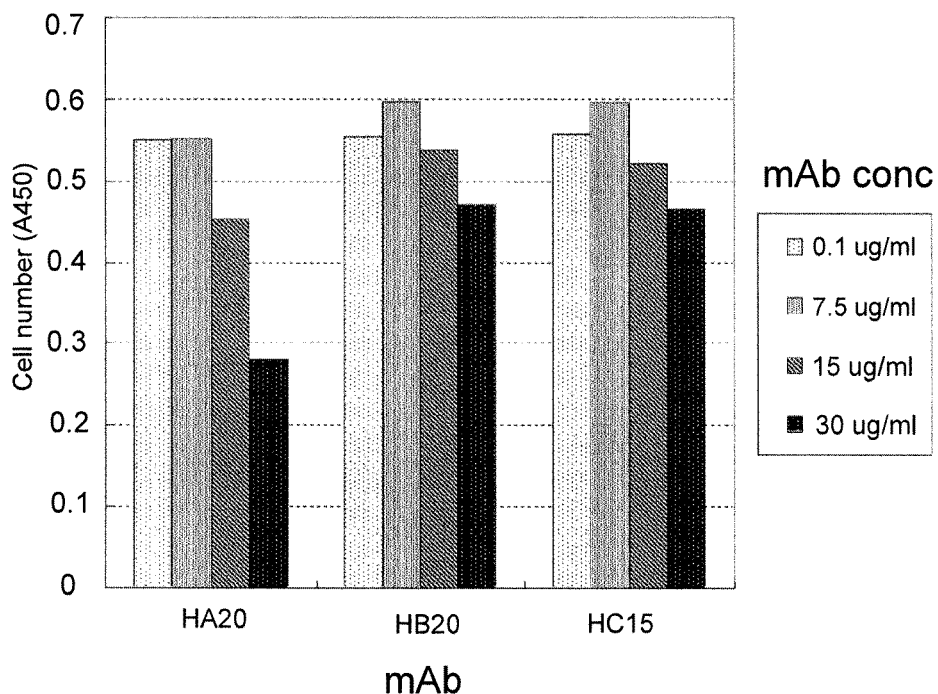

【Fig. 13】
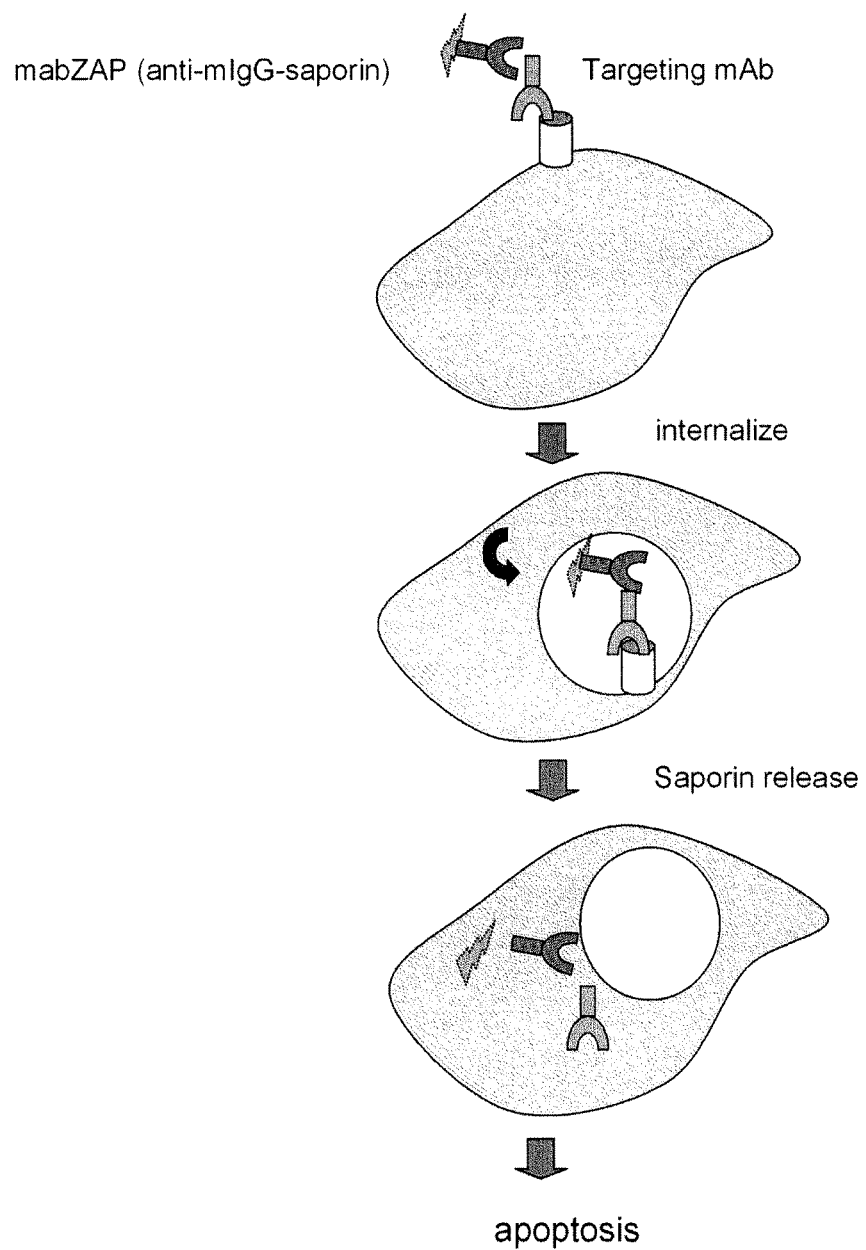

【Fig. 14】
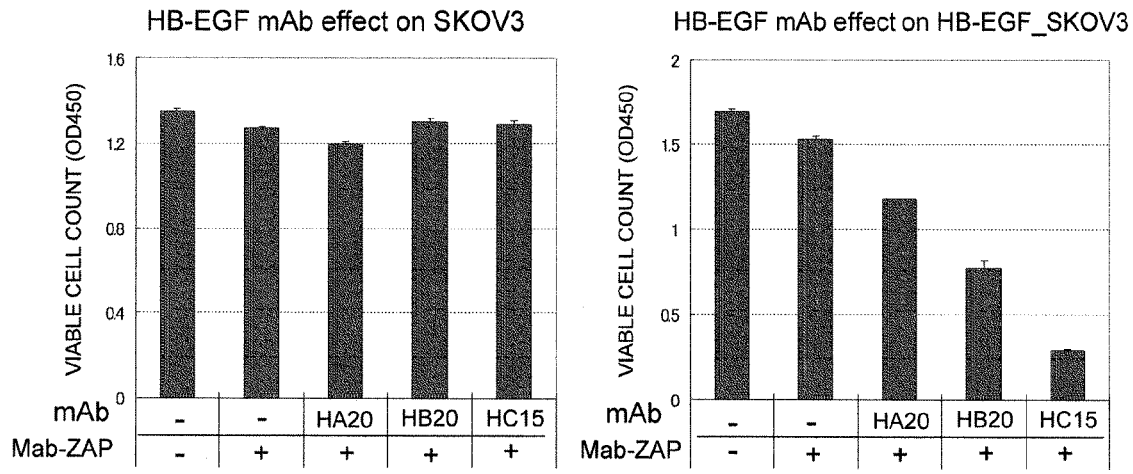
【Fig. 15】
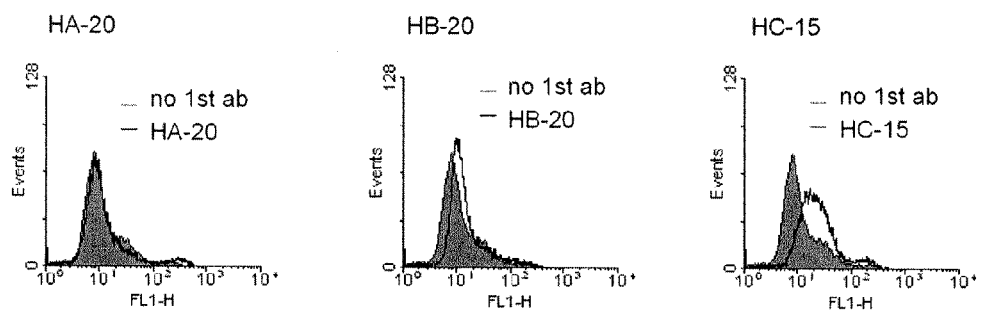

【Fig. 16】
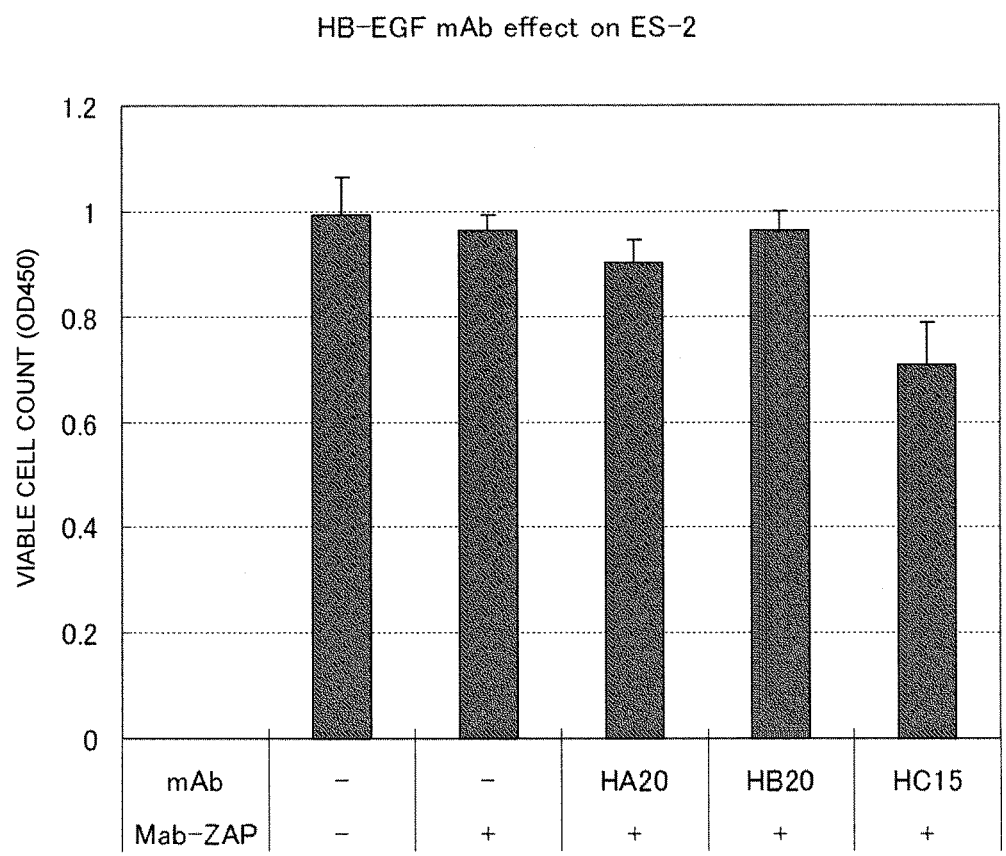
【Fig. 17】
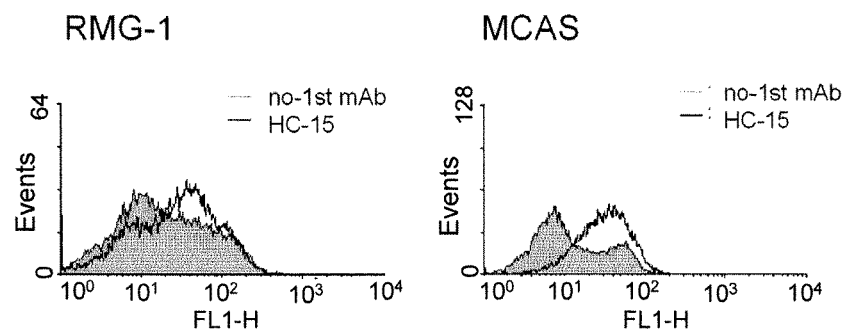

[Fig. 18]
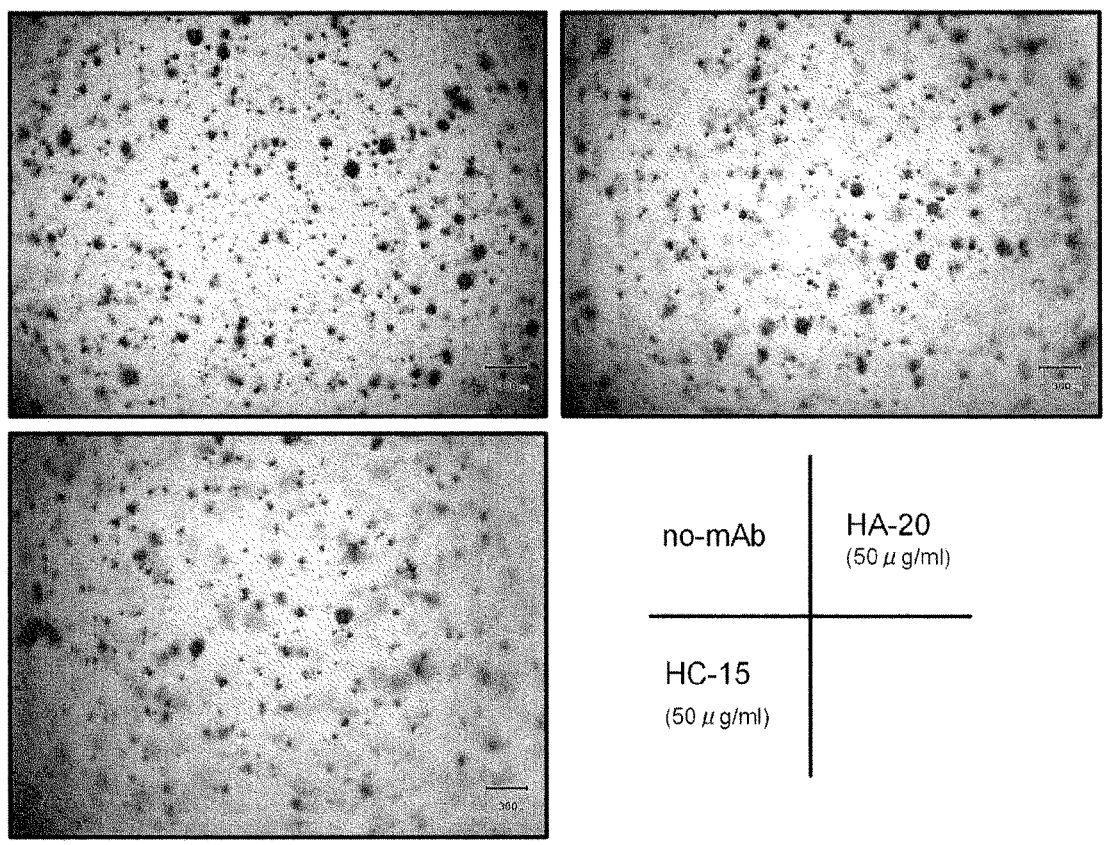

【Fig. 19】
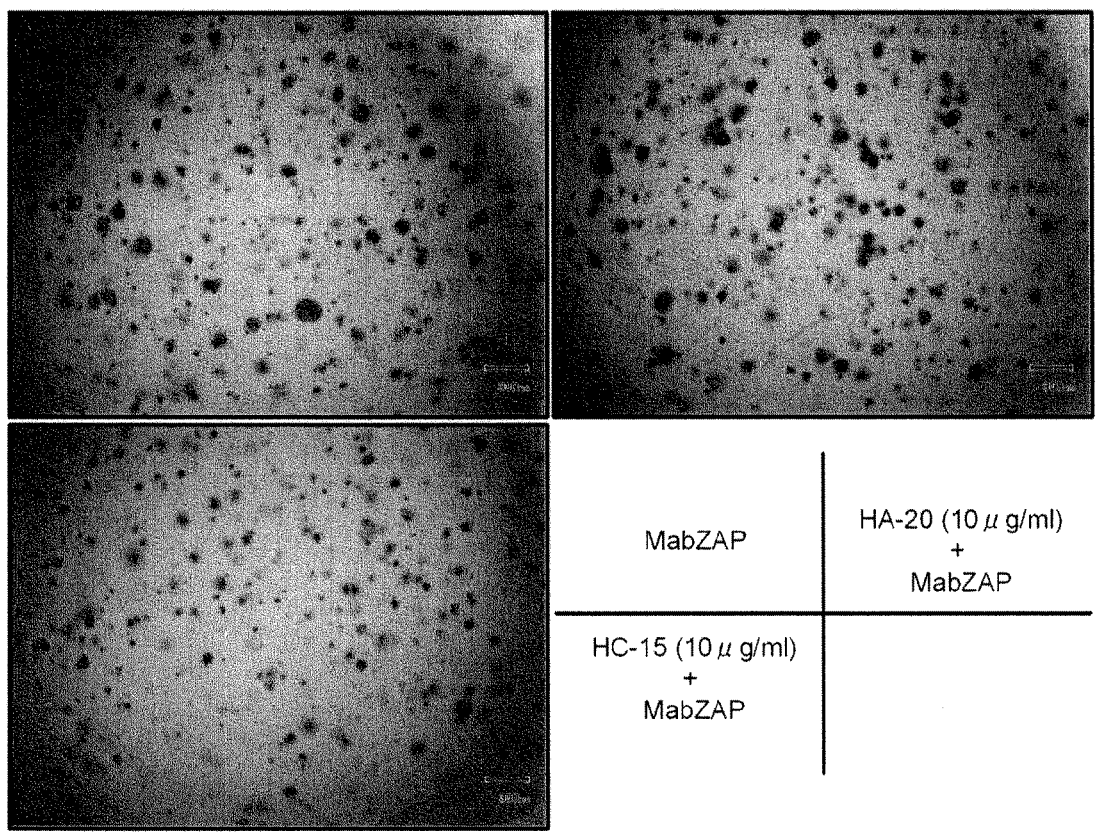

[Fig. 20]
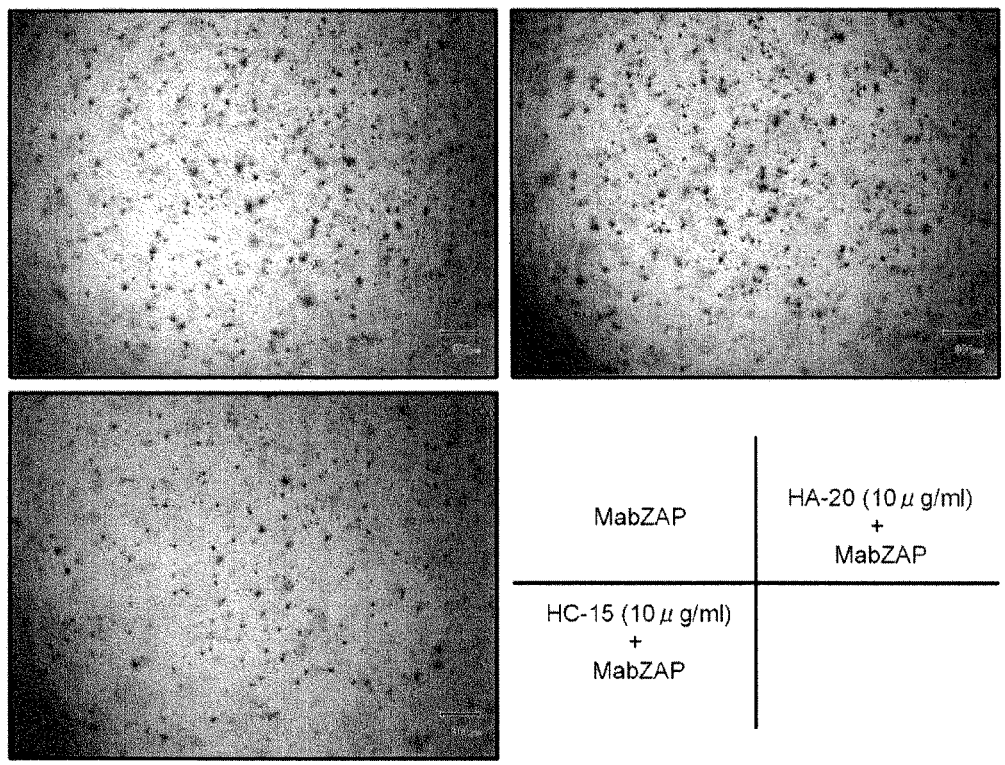
[Fig. 21]
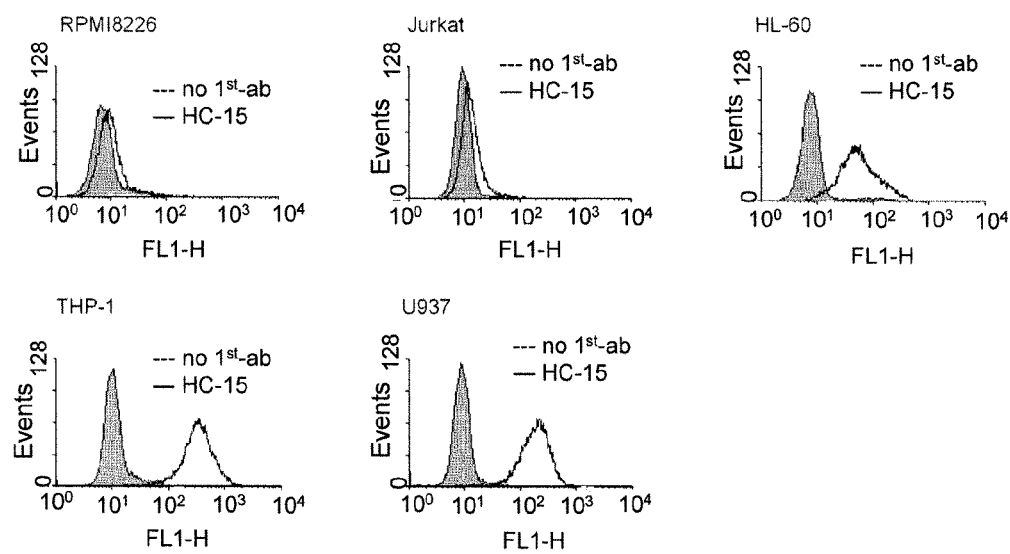

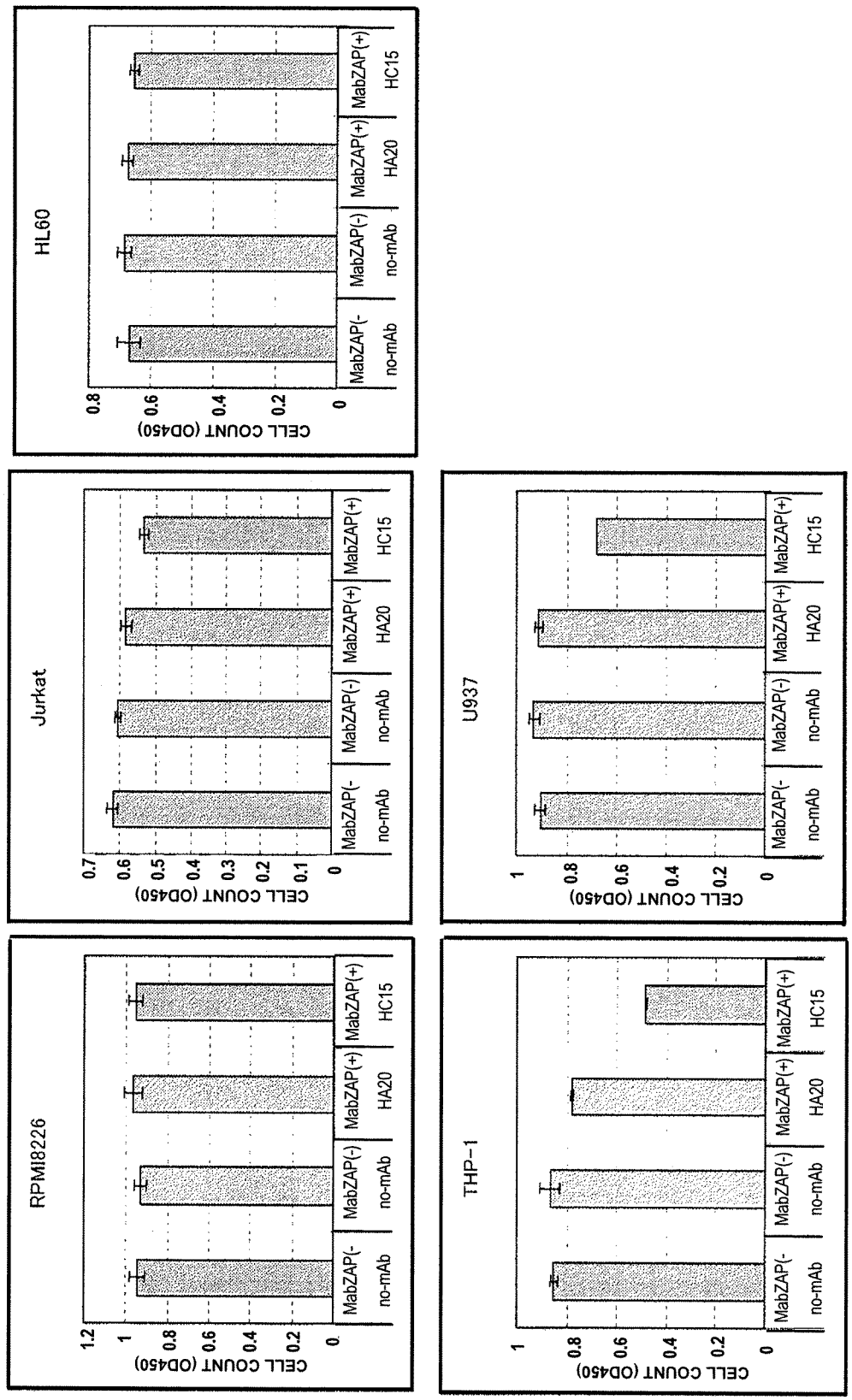
[Fig. 22]

[Fig. 23a]
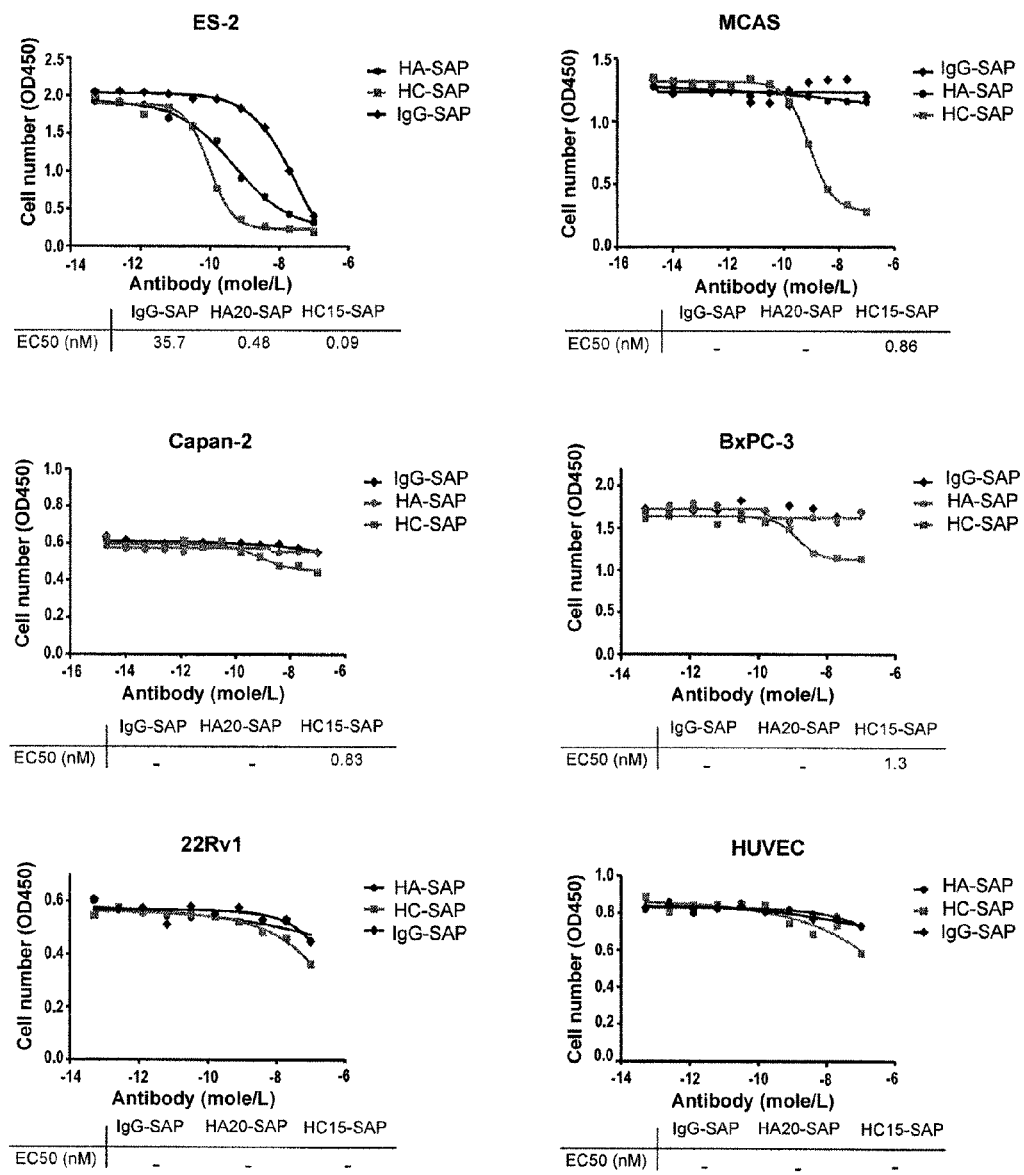

【Fig. 23b】
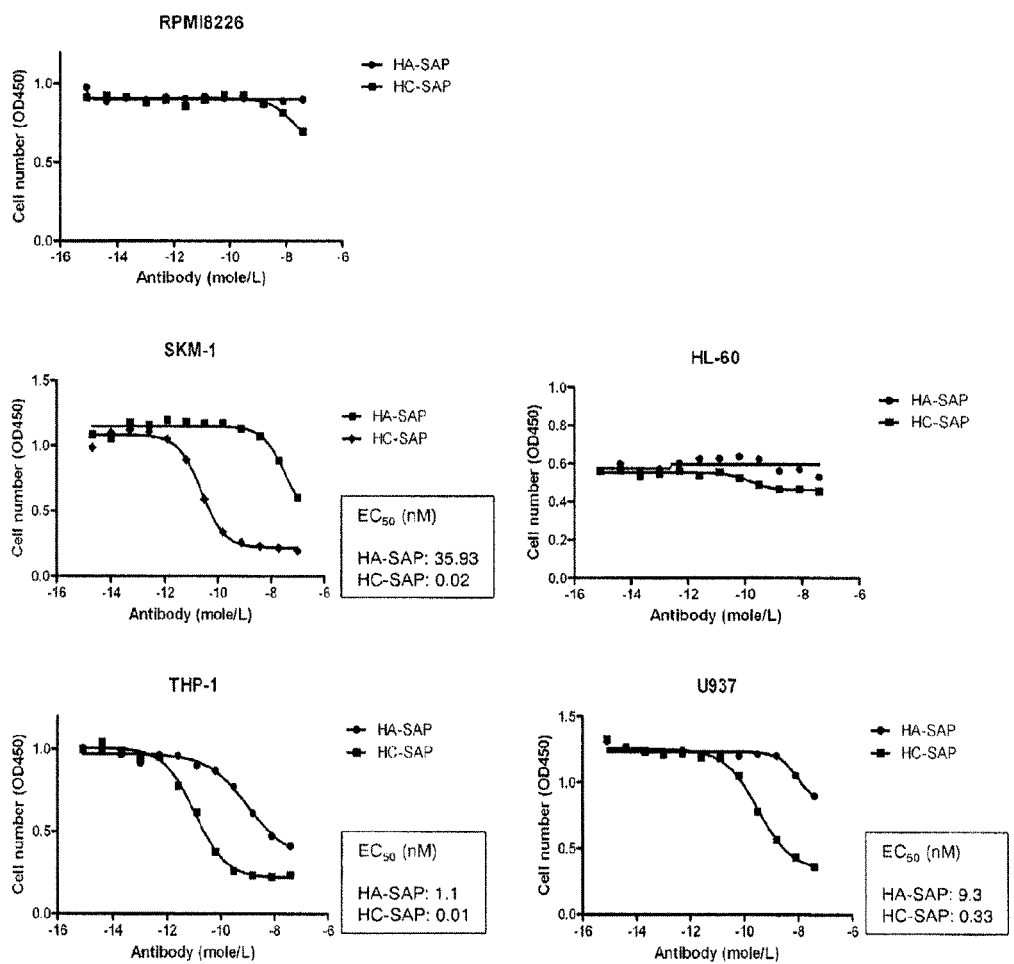
【Fig. 24】
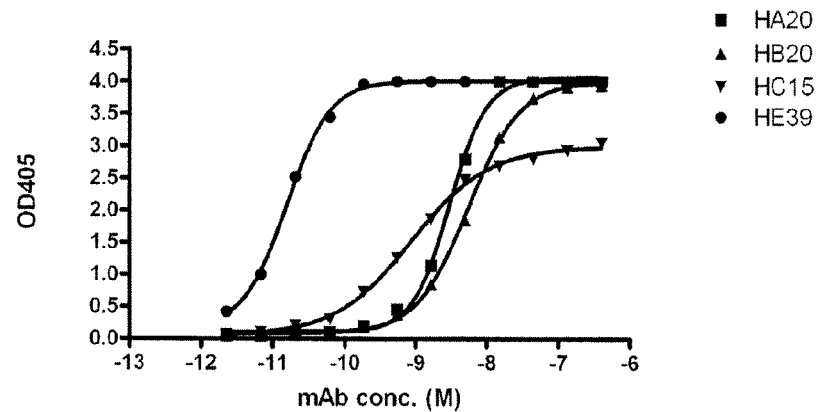

[Fig. 25]
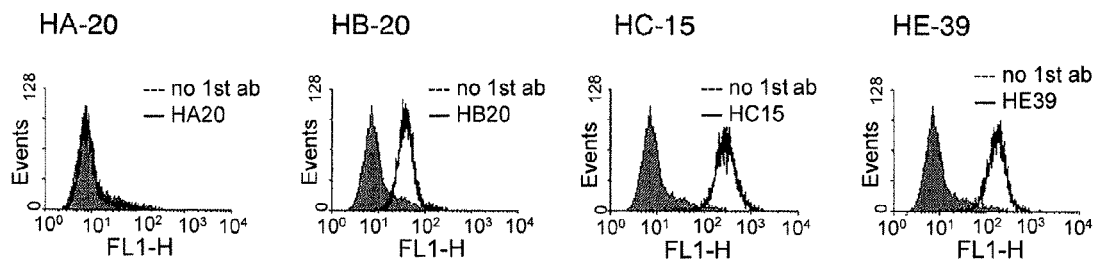
[Fig. 26]
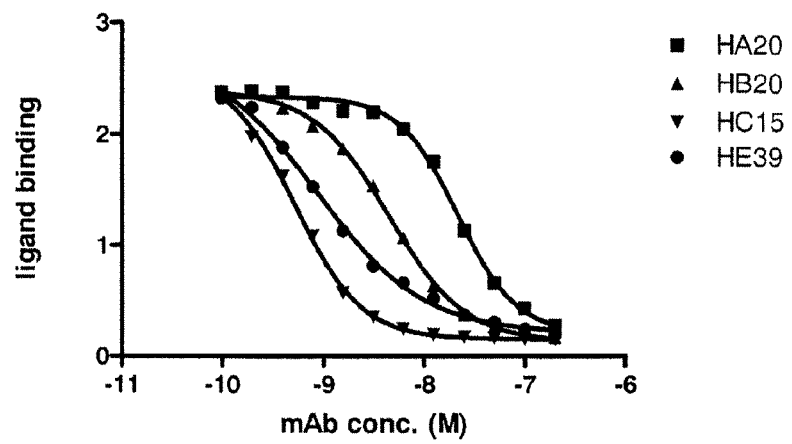
[Fig. 27]
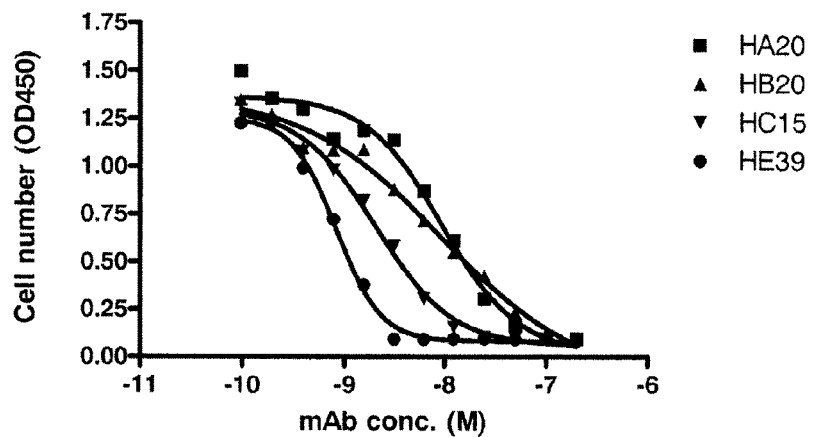

[Fig. 28]

HE39 VARIABLE REGIONS

H CHAIN
```
         VH Segments
         FR1                                        CDR1   FR2              CDR2
         ---------1----------2----------3           -----  ----4---------   5----------6-----
         12345678901234567890123456789012345AB      12345AB 67890123456789  012A3456789012345
HE39_VH  VQLQQSGPELMKPGASVKMSCKASGYIFT              DYYMN   WVKQSHGKSLEWIG   RVNPNNGGTSYSQKFKD JH Segments
         FR3                                         CDR3
         ----7--------8------------9----             ----10--------------   -----11----
         67890123456789012abc345678901234             567890ABCDEFGHIJK12    35678901234
HE39_VH  KATLTVDKSLNTAYMQVNSLTSEDSAVYYCAR             IYYGGSD                WGQGTTLTVSS
```

L CHAIN
```
            VK Segments
            FR1                              CDR1                FR2             CDR2
            ---------1----------2---   ------3---------    -----4---------    5------
            12345678901234567890123    45678901ABCDE234    567890123456789    0123456
HE39_VL-1   EIVMTQTPLSLSVTIGQPASISC    KSSQSLLYTTGKTYLN    WLQQRPGQAPKHLMY    QVSKLVP
HE39_VL-2   NVLTQSPAIMSASPGEKVTMTCS    ASSSVSSMYLH         WYQQKSGASPKLWIY    GTSNLAS JK Segments
            FR3                                         CDR3              FR4
            ---6---------7----------8--------   -9--------------   ---10-----
            789012345678901234567890123456789   9012345ABCDEF67    8901234567
HE39_VL-1   GIPDRFSGSGSETDFTLKISRVEAEDLGVYYC    LQGTYYPHT          FGSGTKLEIK
HE39_VL-2   GVPTRLSGSGSGTSYSLTISSVEAENAATYYC    QQYHSDPFT          FGTGTKLEIK
```

| ANTIBODIES | CHAINS | VARIABLE REGIONS | NUCLEOTIDE SEQUENCES (SEQ ID NOs:) | AMINO ACID SEQUENCES (SEQ ID NOs:) |
|---|---|---|---|---|
| HE39 | H CHAIN | FULL LENGTH (aa1-33 IS SIGNAL) | 85 | 86 |
| | | CDR1 | | 76 |
| | | CDR2 | | 77 |
| | | CDR3 | | 78 |
| HE39 | L-1 CHAIN | FULL LENGTH (aa1-20 IS SIGNAL) | 87 | 88 |
| | | CDR1 | | 79 |
| | | CDR2 | | 80 |
| | | CDR3 | | 81 |
| HE39 | L-2 CHAIN | FULL LENGTH (aa1-23 IS SIGNAL) | 89 | 90 |
| | | CDR1 | | 82 |
| | | CDR2 | | 83 |
| | | CDR3 | | 84 |

【Fig. 29a】
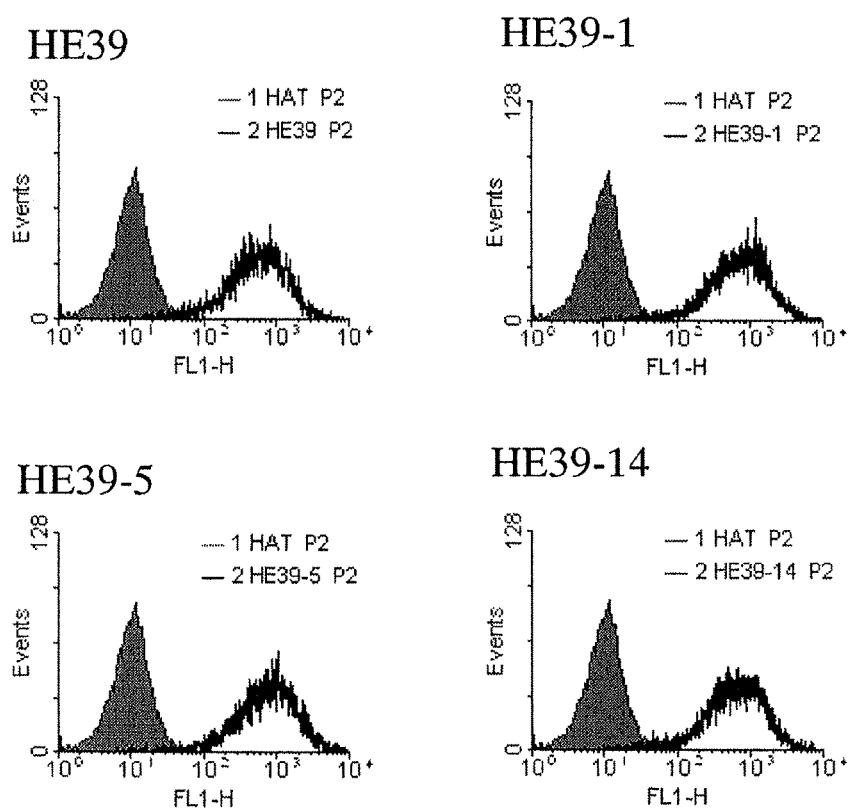

【Fig. 29b】
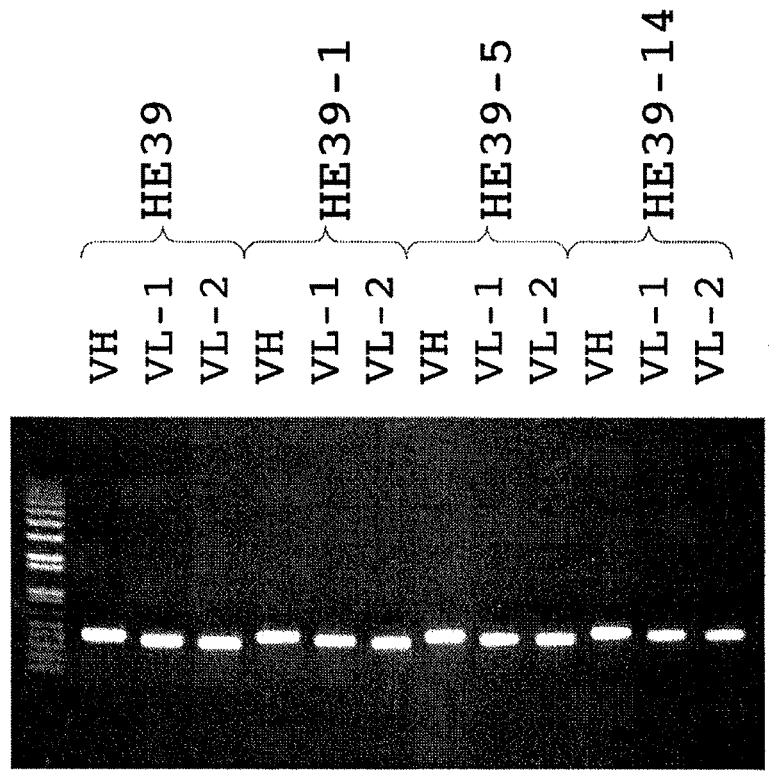
【Fig. 30】
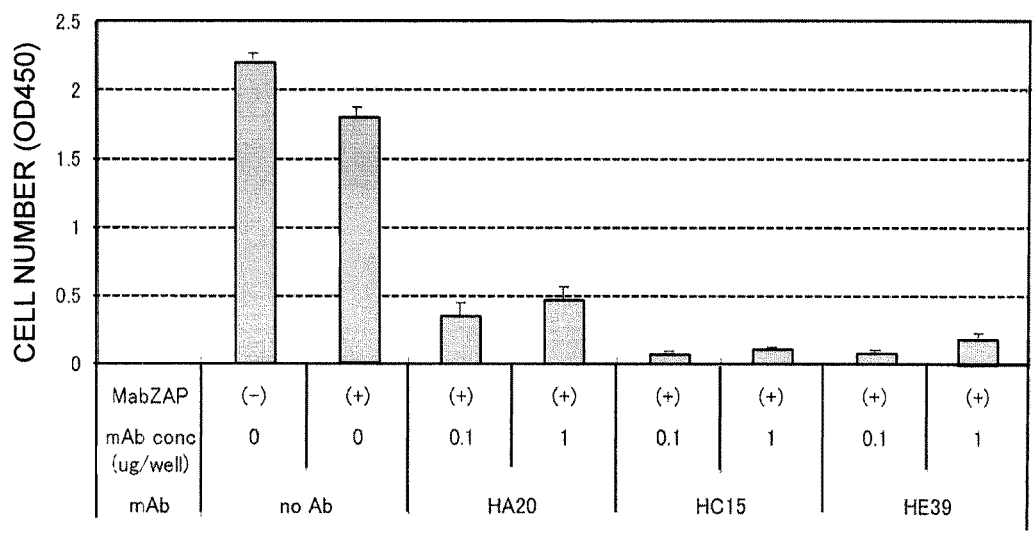

[Fig. 31a]
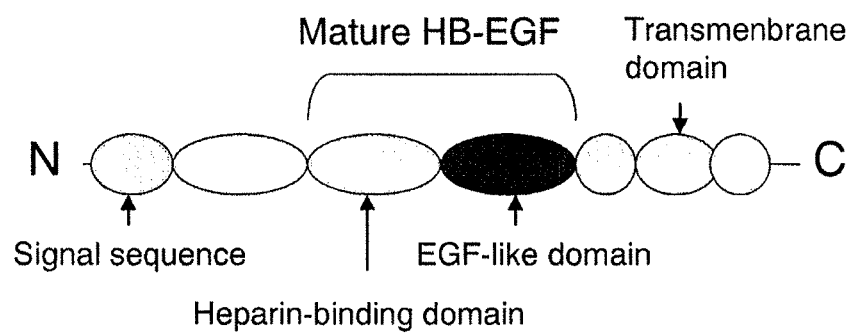

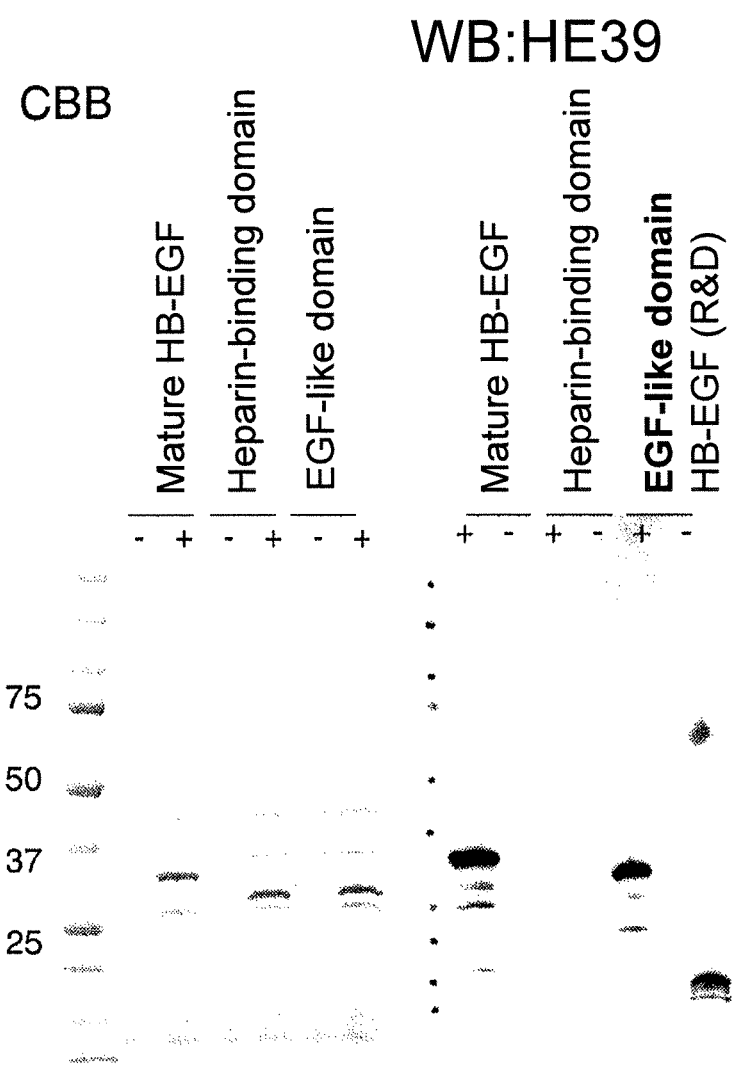
[Fig. 31b]

[Fig. 32a]
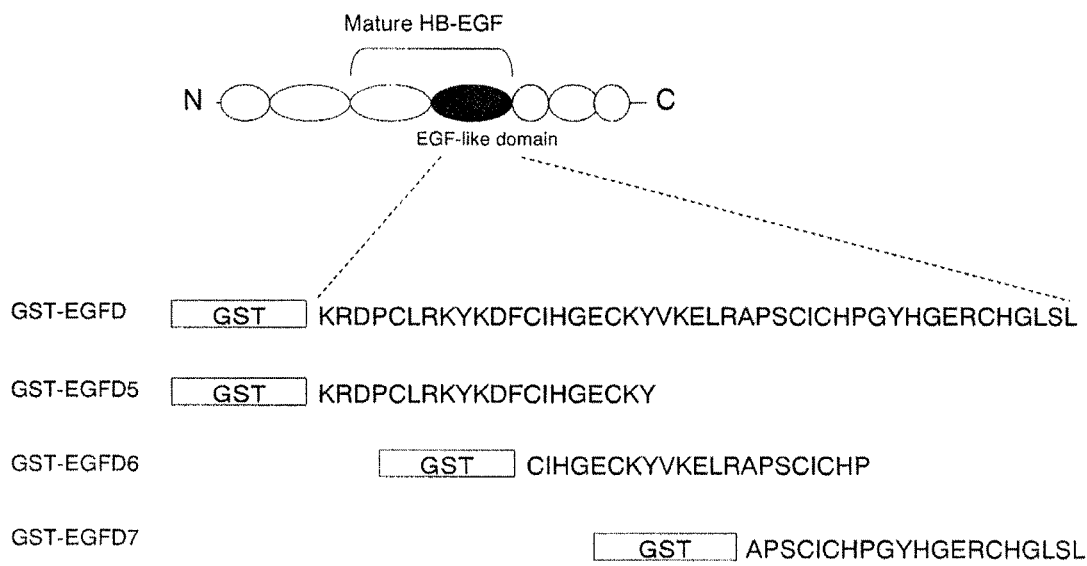
[Fig. 32b]
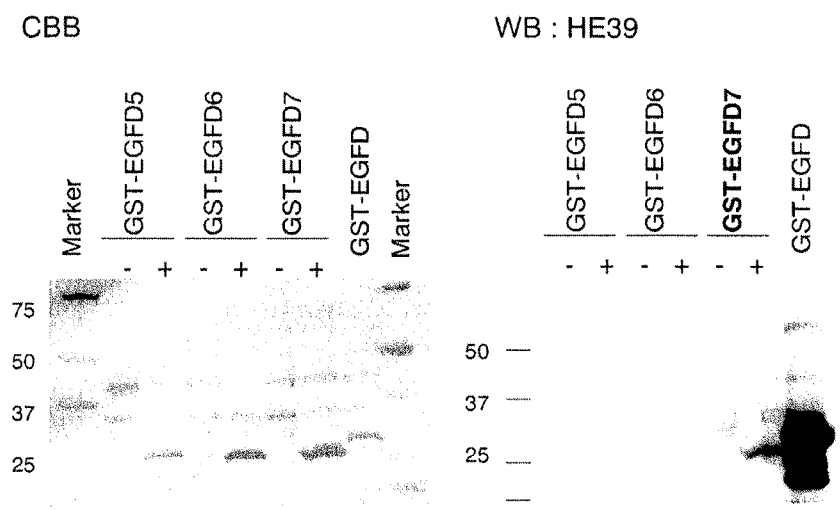

【Fig. 33a】
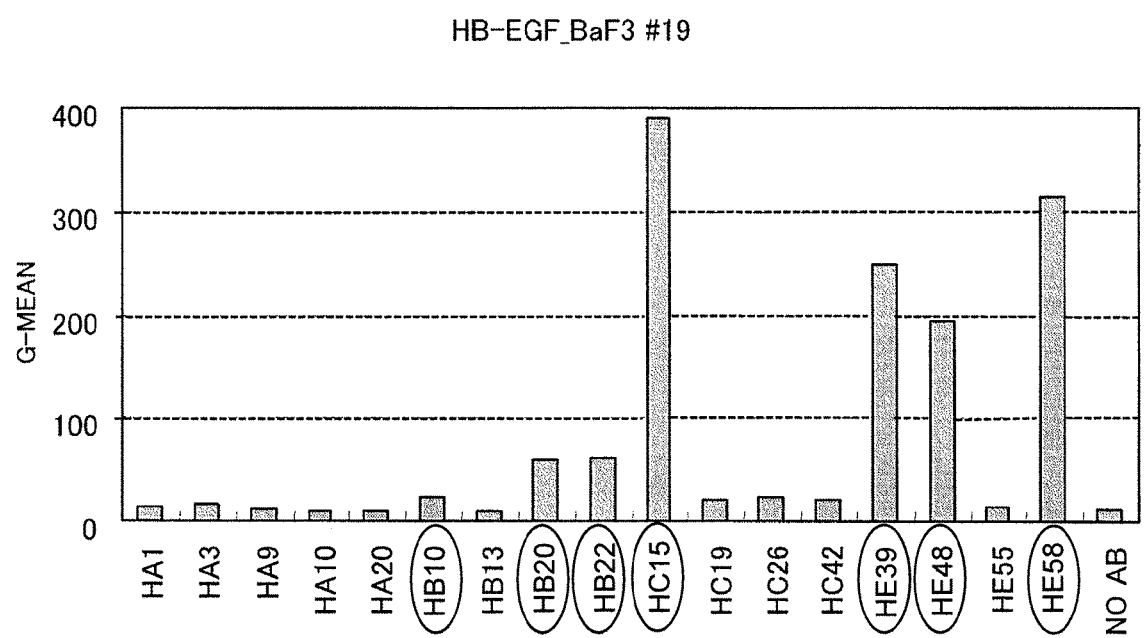

[Fig. 33b]
ADCC
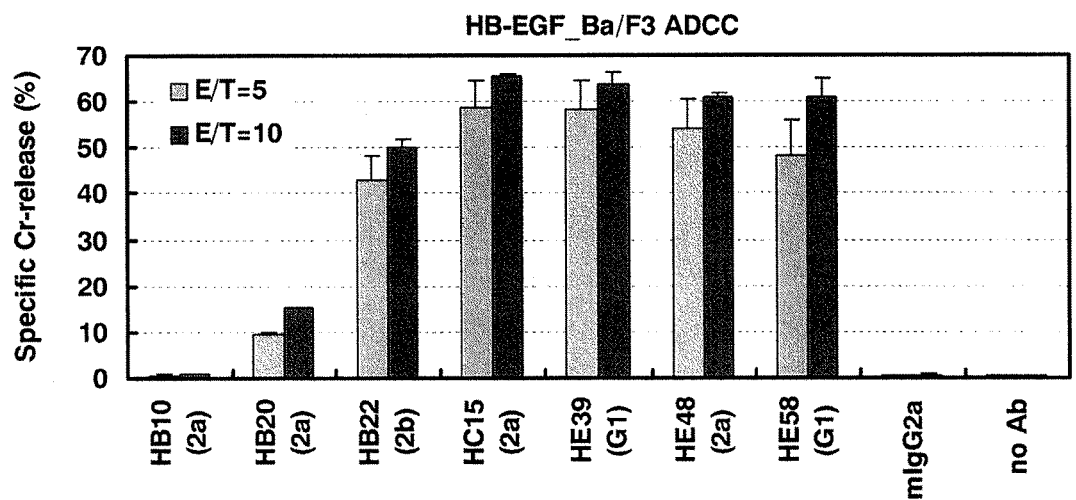
CDC
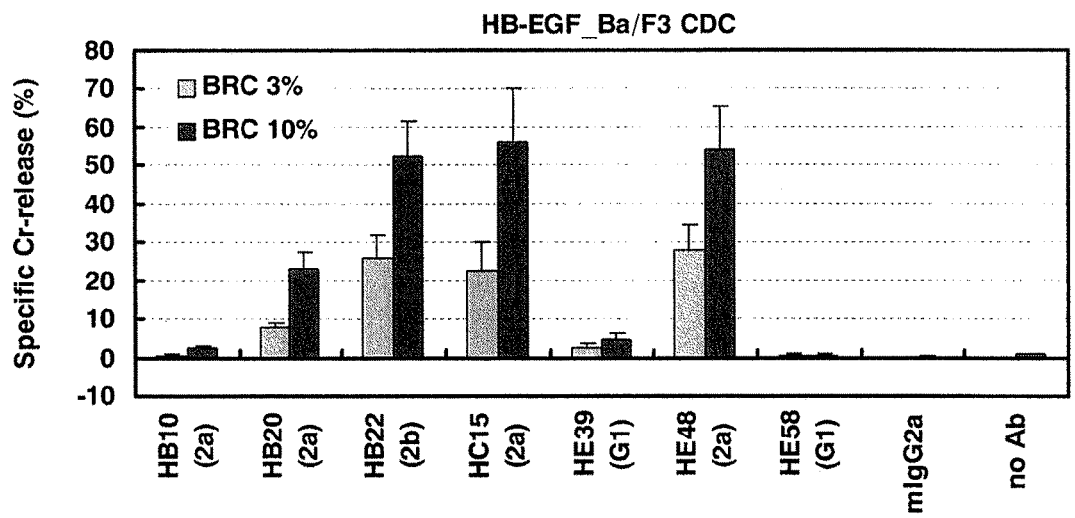

PHARMACEUTICAL COMPOSITION COMPRISING ANTI-HB-EGF ANTIBODY AS ACTIVE INGREDIENT

CROSS REFERENCE TO RELATED PATENT APPLICATIONS

This application is a continuation in part of U.S. patent application Ser. No. 12/311,960 filed Apr. 20, 2009, which is a national phase of International Application No. PCT/JP2007/070487, filed Oct. 19, 2007, which claims priority to Japanese Application No. 2006-286824, filed Oct. 20, 2006 and Japanese Application No. 2007-107207, filed Apr. 16, 2007, the disclosures of which are all hereby incorporated by reference herein.

TECHNICAL FIELD

The present invention relates to a method of treating cancer and to an anti-cancer agent.

BACKGROUND

Heparin-binding epidermal growth factor-like growth factor, or HB-EGF, is a growth factor belonging to the EGF ligand family. HB-EGF gene-null knockout mice exhibit very detrimental phenotypes, such as cardiac function failure accompanied by cardiohypertrophy, and quickly die after birth (Nonpatent Reference 1). This shows that HB-EGF makes a profound contribution to the formation of the heart during gestation. In the adult, on the other hand, its expression is distributed across a relatively broad range of tissues, e.g., the lung, heart, brain, and skeletal muscle (Nonpatent Reference 2), and HB-EGF has a very important role not just during gestation, but also in maintaining biological function in the adult (Nonpatent Reference 3).

HB-EGF occurs as two different structures in vivo: a membrane-bound HB-EGF that is expressed on the cell surface of HB-EGF-expressing cells (designated below as proHB-EGF) and a secreted-form that occurs free from the cell (designated below as sHB-EGF or active-form HB-EGF). The structures of proHB-EGF and sHB-EGF are shown schematically in FIG. 1. The proHB-EGF precursor protein is composed of 208 amino acids and is composed, considered from the N-terminal, of a signal peptide, propeptide, heparin-binding domain, EGF-like domain, juxtamembrane domain, transmembrane domain, and cytoplasmic domain. Cleavage of the signal peptide from the proHB-EGF precursor protein results in the expression of proHB-EGF as a type 1 transmembrane protein. Subsequently, proHB-EGF is subjected to protease digestion, known as ectodomain shedding, and sHB-EGF, composed of 73 to 87 amino acid residues, is released into the extracellular environment. This sHB-EGF is composed of just two domains, the heparin-binding domain and the EGF-like domain, and binds as an active ligand to the EGF receptor (Her1) and EGF receptor 4 (Her4). This results in the induction of proliferation, via the downstream ERK/MAPK signaling pathway, in a variety of cells, e.g., NIH3T3 cells, smooth muscle cells, epithelial cells, keratinocytes, renal tubule cells, and so forth (Nonpatent Reference 4). A substantial reduction in proliferation ability occurs with cells that express only proHB-EGF due to the introduction of mutation into the region that participates in ectodomain shedding. In addition, transgenic mice that express only proHB-EGF have the same phenotype as HB-EGF knockout mice. Based on these observations, the function of HB-EGF as a growth factor is thought to be borne mainly by the secreted form of HB-EGF (Nonpatent References 5 and 6).

proHB-EGF, on the other hand, is also known to have a unique function in vivo different from that of sHB-EGF. That is, proHB-EGF was initially known to function as a receptor for the diphtheria toxin (DT) (Nonpatent References 7 and 8). However, subsequent research demonstrated that proHB-EGF forms complexes at the cell surface with molecules such as DRAP27/CD9 and also integrin $\alpha_3\beta_1$ and heparin sulfate and participates in cell adhesion and migration. Operating through the EGF receptor (designated hereafter as EGFR) via a juxtacrine mechanism, proHB-EGF has also been shown to inhibit the growth of neighboring cells and to induce neighboring cell death. Thus, with regard to HB-EGF in its role as a ligand for EGFR, the membrane-bound proHB-EGF and secreted-form sHB-EGF are known to transmit diametrically opposite signals (Nonpatent References 5 and 8).

HB-EGF has a strong promoting activity on cell proliferation, cell movement, and infiltration in a variety of cell lines, for example, cancer cells. In addition, an increase in HB-EGF expression over that in normal tissue has been reported for a broad range of cancer types (e.g., pancreatic cancer, liver cancer, esophageal cancer, melanoma, colorectal cancer, gastric cancer, ovarian cancer, uterine cervical cancer, breast cancer, bladder cancer, and brain tumors), suggesting that HB-EGF is strongly implicated in cancer proliferation or malignant transformation (Nonpatent References 4 and 10).

Based on these findings, the inhibition of cancer cell growth via an inhibition of HB-EGF activity has therefore been pursued. The following effects, inter alia, have been reported for efforts to inhibit the action of HB-EGF using anti-HB-EGF neutralizing antibodies: an inhibition of DNA synthesis in 3T3 cells (Nonpatent Reference 11), an inhibition of keratinocyte growth (Nonpatent Reference 12), an inhibition of glioma cell growth (Nonpatent Reference 13), and an inhibition of DNA synthesis in myeloma cells (Nonpatent Reference 14).

Meanwhile the use of an attenuated diphtheria toxin (CRM197) that specifically binds to HB-EGF as an HB-EGF inhibitor has also been pursued. In fact, in a test of the efficacy in a mouse xenograft model (transplantation of an ovarian cancer cell line), the group receiving CRM197 presented a superior tumor shrinkage effect (Nonpatent Reference 15). In addition, clinical testing with CRM197 has also been carried out in cancer patients (Nonpatent Reference 16).

The references cited in this specification is listed below. The contents of these documents are herein incorporated by reference in their entirety. None of these documents is admitted as prior art to the present invention:

Nonpatent Reference 1: Iwamoto R, Yamazaki S, Asakura M et al., Heparin-binding EGF-like growth factor and ErbB signaling is essential for heart function. *Proc. Natl. Acad. Sci. USA,* 2003; 100:3221-6.

Nonpatent Reference 2: Abraham J A, Damm D, Bajardi A, Miller J, Klagsbrun M, Ezekowitz R A. Heparin-binding EGF-like growth factor: characterization of rat and mouse cDNA clones, protein domain conservation across species, and transcript expression in tissues. *Biochem Biophys Res Commun,* 1993; 190:125-33.

Nonpatent Reference 3: Karen M., *Frontiers in Bioscience,* 3, 288-299, 1998.

Nonpatent Reference 4: Raab G, Klagsbrun M. Heparin-binding EGF-like growth factor. *Biochim Biophys Acta,* 1997; 1333:F179-99.

Nonpatent Reference 5: Yamazaki S, Iwamoto R, Saeki K et al. Mice with defects in HB-EGF ectodomain shedding show severe developmental abnormalities. *J Cell Biol,* 2003; 163:469-75.

Nonpatent Reference 6: Ongusaha P., *Cancer Res,* (2004) 64, 5283-5290.

Nonpatent Reference 7: Iwamoto R., Higashiyama S., *EMBO J.* 13, 2322-2330 (1994).

Nonpatent Reference 8: Naglich J G., Metherall J E., *Cell,* 69, 1051-1061 (1992).

Nonpatent Reference 9: Iwamoto R, Handa K, Mekada E. Contact-dependent growth inhibition and apoptosis of epidermal growth factor (EGF) receptor-expressing cells by the membrane-anchored form of heparin-binding EGF-like growth factor. *J. Biol. Chem.* 1999; 274:25906-12.

Nonpatent Reference 10: Miyamoto S, *Cancer Sci.* 97, 341-347 (2006).

Nonpatent Reference 11: Blotnick S., *Proc. Natl. Acad. Sci. USA,* (1994) 91, 2890-2894.

Nonpatent Reference 12: Hashimoto K., *J. Biol. Chem.* (1994) 269, 20060-20066.

Nonpatent Reference 13: Mishima K., *Act Neuropathol.* (1998) 96, 322-328.

Nonpatent Reference 14: Wang Y D. *Oncogene,* (2002) 21, 2584-2592.

Nonpatent Reference 15: Miyamoto S., *Cancer Res.* (2004) 64, 5720

Nonpatent Reference 16: Buzzi S., *Cancer Immunol Immunother,* (2004) 53, 1041-1048.

DISCLOSURE OF THE INVENTION

An object of the present invention is to provide a novel pharmaceutical composition comprising an anti-HB-EGF antibody. A more particular object is to provide a novel method for treating cancer using an anti-HB-EGF antibody, a novel cell proliferation inhibitor that comprises an anti-HB-EGF antibody, a novel anti-cancer agent that comprises an anti-HB-EGF antibody, as well as a novel anti-HB-EGF antibody.

The present inventors have discovered that an internalizing activity is exhibited by antibody against HB-EGF, which is a protein highly expressed in cancer cells. The present inventors have also discovered that antibody against HB-EGF exhibits an antibody-dependent cell-mediated cytotoxicity (ADCC) and/or a complement-dependent cytotoxicity (CDC). Based on the findings, the present inventors also discovered that anti-HB-EGF antibody is effective for the treatment of cancers in which HB-EGF expression is upregulated, most prominently ovarian cancer, and thereby achieved the present invention.

When the present inventors produced monoclonal antibody by immunizing mice with HB-EGF protein, they found that the obtained antibody had an internalizing activity. In addition, when a cytotoxic substance was bound to the obtained internalizing anti-HB-EGF antibody and the cell death-inducing activity was measured, a significant cell death-inducing activity was noted. Furthermore, when the ADCC activity and CDC activity of the obtained anti-HB-EGF antibody were measured, the anti-HB-EGF antibody was found to exhibit ADCC activity and/or CDC activity.

Thus, the present application provides a monoclonal antibody and a lower molecular weight antibody derivative selected from the following (1) to (24):

(1) An anti-HB-EGF antibody having an internalizing activity;

(2) An anti-HB-EGF antibody to which a cytotoxic substance is attached;

(3) The antibody according to (2), having an internalizing activity;

(4) An anti-HB-EGF antibody having an ADCC activity or a CDC activity;

(5) The antibody according to any one of (1) to (4), further having a neutralizing activity;

(6) An antibody selected from the following [1] to [13]:

[1] an antibody comprising a heavy chain variable region having the amino acid sequence of SEQ ID NO: 14 as CDR1, the amino acid sequence of SEQ ID NO: 16 as CDR2, and the amino acid sequence of SEQ ID NO: 18 as CDR3;

[2] an antibody comprising a light chain variable region having the amino acid sequence of SEQ ID NO: 20 as CDR1, the amino acid sequence of SEQ ID NO: 22 as CDR2, and the amino acid sequence of SEQ ID NO: 24 as CDR3;

[3] an antibody comprising the heavy chain according to [1] and the light chain according to [2];

[4] an antibody comprising a heavy chain variable region having the amino acid sequence of SEQ ID NO: 26 as CDR1, the amino acid sequence of SEQ ID NO: 28 as CDR2, and the amino acid sequence of SEQ ID NO: 30 as CDR3;

[5] an antibody comprising a light chain variable region having the amino acid sequence of SEQ ID NO: 32 as CDR1, the amino acid sequence of SEQ ID NO: 34 as CDR2, and the amino acid sequence of SEQ ID NO: 36 as CDR3;

[6] an antibody comprising the heavy chain according to [4] and the light chain according to [5];

[7] an antibody comprising a heavy chain variable region having the amino acid sequence of SEQ ID NO: 76 as CDR1, the amino acid sequence of SEQ ID NO: 77 as CDR2, and the amino acid sequence of SEQ ID NO: 78 as CDR3 (HE-39H chain);

[8] an antibody comprising a light chain variable region having the amino acid sequence of SEQ ID NO: 79 as CDR1, the amino acid sequence of SEQ ID NO: 80 as CDR2, and the amino acid sequence of SEQ ID NO: 81 as CDR3 (HE-39 L chain-1);

[9] an antibody comprising a light chain variable region having the amino acid sequence of SEQ ID NO: 82 as CDR1, the amino acid sequence of SEQ ID NO: 83 as CDR2, and the amino acid sequence of SEQ ID NO: 84 as CDR3 (HE-39 L chain-2);

[10] an antibody comprising the heavy chain according to [7] and the light chain according to [9];

[11] an antibody comprising the heavy chain according to [7] and the light chain according to [9];

[12] an antibody having the activity equivalent to that of the antibody according to any of [1] to [11]; and

[13] an antibody that binds an epitope that is the same as the epitope bound by an antibody described in any of [1] to [12].

(7) A pharmaceutical composition comprising an antibody according to any one of (1) to (6);

(8) A pharmaceutical composition comprising a cytotoxic substance attached to the antibody according to any one of (1) to (6);

(9) The pharmaceutical composition according to (7) or (8), which is a cell proliferation inhibitor;

(10) The pharmaceutical composition according to (9), which is an anti-cancer agent;

(11) The pharmaceutical composition according to (10), wherein the cancer is pancreatic cancer, liver cancer, esophageal cancer, melanoma, colorectal cancer, gastric cancer, ovarian cancer, uterine cervical cancer, breast cancer, bladder cancer, a brain tumor, or a hematological cancer;

(12) A method of delivering a cytotoxic substance into a cell by means of an anti-HB-EGF antibody;

(13) A method of inhibiting cell proliferation with a cytotoxic substance attached to an anti-HB-EGF antibody;

(14) The method according to (13), wherein the cell is a cancer cell;

(15) The method according to any one of (12) to (14), wherein the cytotoxic substance is a chemotherapeutic agent, a radioactive substance, or a toxic peptide;

(16) Use of an anti-HB-EGF antibody for transporting a cytotoxic substance into a cell;

(17) Use of an anti-HB-EGF antibody having an internalizing activity for inhibiting cell proliferation;

(18) The use according to (17), wherein the anti-HB-EGF antibody further comprises a neutralizing activity;

(19) The use according to (18), wherein the anti-HB-EGF antibody further comprises an ADCC activity or a CDC activity;

(20) The use according to any one of (16) to (19), wherein the cell is a cancer cell;

(21) The use according to any one of (16) to (19), wherein a cytotoxic substance is attached to the anti-HB-EGF antibody;

(22) A method of producing a pharmaceutical composition comprising the steps of:
(a) providing an anti-HB-EGF antibody;
(b) determining whether the antibody of (a) has an internalizing activity;
(c) selecting an antibody that has an internalizing activity; and
(d) attaching a cytotoxic substance to the antibody selected in (c);

(23) The production method according to (22), wherein the pharmaceutical composition is an anti-cancer agent;

(24) A method of diagnosing cancer using an anti-HB-EGF antibody;

(25) The diagnostic method according to (24) comprising using an anti-HB-EGF antibody to which a labeling substance is attached;

(26) The diagnostic method according to (24) or (25), wherein an intracellularly incorporated anti-HB-EGF antibody is detected;

(27) An anti-HB-EGF antibody to which a labeling substance is attached;

(28) The antibody according to (27), having an internalizing activity.

BRIEF DESCRIPTION OF THE DRAWINGS

FIG. 1 is a diagram that schematically depicts the structure of proHB-EGF, sHB-EGF, and the HB-EGF_Fc used as immunogen;

FIG. 2a is a diagram that schematically depicts the influence of the binding of HB-EGF to the EGFR_Ba/F3 cell;

FIG. 2b is a graph that shows the dependence of EGFR_Ba/F3 cell proliferation on the HB-EGF concentration;

FIG. 3a is a graph that shows the neutralizing activity of HB-EGF antibodies (HA-1, HA-3, HA-9, HA-10, and HA-20) on the HB-EGF-dependent growth of EGFR_Ba/F3 cells;

FIG. 3b is a graph that shows the neutralizing activity of HB-EGF antibodies (HB-10, HB-13, HB-20, HB-22, and HC-74) on the HB-EGF-dependent growth of EGFR_Ba/F3 cells;

FIG. 3c is a graph that shows the neutralizing activity of HB-EGF antibodies (HC-15, HC-19, HC-26, and HC-42) on the HB-EGF-dependent growth of EGFR_Ba/F3 cells;

FIG. 4A is a comparison of the variable region sequences of HB-EGF neutralizing antibodies;

FIG. 4B is a comparison of the variable region sequences of HB-EGF neutralizing antibodies;

FIG. 5 is a graph that shows the binding activity of antibodies HA-20, HB-20, and HC-15 to active-form HB-EGF;

FIG. 6 shows histograms that show the binding activity of antibodies HA-20, HB-20, and HC-15 to proHB-EGF;

FIG. 7 is a schematic illustration showing the inhibition of binding between HB-EGF and EGFR by HB-EGF antibody on a solid phase;

FIG. 8 is a schematic illustration showing an ELISA-based analysis model for the EGFR/HB-EGF binding mode;

FIG. 9 is a graph that shows the concentration curve for HB-EGF detected in the ELISA-based analysis model for the EGFR/HB-EGF binding mode;

FIG. 10 is a graph that shows the inhibition of binding of HB-EGF to EGFR by antibodies HA-20, HB-20, and HC-15;

FIG. 11 is a graph that compares the inhibition of the growth of EGFR_Ba/F3 cells by antibodies HA-20, HB-20, and HC-15;

FIG. 12a is a graph that shows the inhibition of growth of the ovarian cancer cell line RMG-1 by the antibodies HA-20, HB-20, and HC-15 in a medium containing 8% FCS;

FIG. 12b is a graph that shows the inhibition of growth of the ovarian cancer cell line RMG-1 by the antibodies HA-20, HB-20, and HC-15 in a medium containing 2% FCS;

FIG. 13 is a schematic diagram of the process in which cell death is induced by the internalization into a cell of an antibody bound to antigen (complex of HB-EGF targeting antibody and saporin-labeled antibody);

FIG. 14 is a graph that shows the internalization-mediated activity of the HA-20, HB-20, and HC-15 antibodies to induce cell death in SKOV-3 cells (original cell line) and HB-EGF_SKOV3 cells (high HB-EGF-expressing SKOV-3 cells);

FIG. 15 is a histograms that show the binding activity of the HA-20, HB-20, and HC-15 antibodies for the HB-EGF on ES-2 cells;

FIG. 16 is a graph that shows the internalization-mediated cell death inducing activity of HA-20, HB-20, and HC-15, on ES-2 ovarian cancer cells;

FIG. 17 shows histograms of the FACS analysis of the expression of HB-EGF by ovarian cancer lines (RMG-1, MCAS);

FIG. 18 is a diagram of the analysis of the neutralizing activity of the antibodies HA-20 and HC-15, to inhibit proliferation of RMG-1 cells in the soft agar colony formation assay;

FIG. 19 is a diagram of the analysis of the internalization-mediated proliferation inhibiting activity of the antibodies HA-20 and HC-15 on RMG-1 ovarian cancer cells in the soft agar colony formation assay;

FIG. 20 is a diagram of the analysis of the internalization-mediated proliferation inhibiting activity of the antibodies HA-20 and HC-15 on MCAS ovarian cancer cells in the soft agar colony formation assay;

FIG. 21 shows histograms of the FACS analysis of the expression of HB-EGF by several hematological cancer cell lines;

FIG. 22 shows graphs that show the internalization-mediated inhibition of proliferation by the HA-20 and HC-15 antibodies on several hematological cancer cell lines;

FIG. 23a is a diagram of the analysis of the proliferation inhibiting activity exhibited by saporin-labeled HA-20 antibody (HA-SAP), saporin-labeled HC-15 antibody (HC-SAP), and saporin-labeled control antibody (IgG-SAP) on various solid cancer cell lines and normal human endothelial cells;

FIG. 23b is a diagram of the analysis of the proliferation inhibiting activity exhibited by saporin-labeled HA-20 antibody (HA-SAP) and saporin-labeled HC-15 antibody (HC-SAP) on various hematological cancer cell lines;

FIG. 24 is a graph that compares the binding activity of the antibody HE-39 to the active-form HB-EGF with the binding activity of the antibodies HA-20, HB-20, and HC-15 to the active-form HB-EGF;

FIG. 25 shows histograms that show the binding activity of the antibody HE-39 and the antibodies HA-20, HB-20, and HC-15 to the proHB-EGF overexpressed in DG44 cells;

FIG. 26 is a graph that shows the ability of the HA-20, HB-20, HC-15, and HE-39 antibodies to inhibit binding of HB-EGF to EGFR;

FIG. 27 shows a graph that compares the growth inhibiting activity exhibited by the HA-20, HB-20, HC-15, and HE-39 antibodies on EGFR_Ba/F3 cells;

FIG. 28 is a comparison of the variable region sequences of the HE-39 antibody;

FIG. 29a shows histograms that show the binding activity for the proHB-EGF overexpressed in DG44 cells of the monoclonal antibodies (HE39-1, HE39-5, HE39-14) obtained by the performance of an additional limit dilution of the HE-39 antibody;

FIG. 29b is a schematic diagram in which the expression of the individual variable regions (VH, VL-1, VL-2) is identified by RT-PCR for the monoclonal antibodies (HE39-1, HE39-5, HE39-14) obtained by an additional limit dilution of the HE-39 antibody;

FIG. 30 is a graph that shows the internalization-mediated cell death inducing activity exhibited by the antibodies HE-39, HA-20, and HC-15 on HB-EGF_DG44 cells;

FIG. 31a is a diagram that schematically depicts the structure of HB-EGF (top), and the structure of the fusion proteins between GST protein and mature HB-EGF or each individual domain (heparin-binding domain, EGF-like domain) (bottom);

FIG. 31b shows the results of SDS-PAGE on the GST fusion proteins expressed in *E. coli* and CBB staining (left) and Western blotting with the HE-39 antibody (right);

FIG. 32a shows the amino acid sequence of the EGF-like domain (EGFD) of HB-EGF and the amino acid sequences of the EGF-like domain divided into three fragments (EGFD5, EGFD6, EGFD7); these sequences were fused to the C terminal of GST protein for use in epitope mapping;

FIG. 32b shows the results of SDS-PAGE on the GST fusion proteins (GST-EGFD, GST-EGFD5, GST-EGFD6, GST-EGFD7) expressed in *E. coli* and CBB staining (left) and Western blotting with the HE-39 antibody (right);

FIG. 33a is a graph of the FACS analysis of the binding activity exhibited by various anti-HB-EGF antibodies for HB-EGF overexpressed in Ba/F3 cells; the fluorescence intensity is expressed on the vertical axis as the G-mean value; and FIG. 33b shows the ADCC activity exhibited by various anti-HB-EGF antibodies on HB-EGF_Ba/F3 cells (upper) and the CDC activity exhibited by various anti-HB-EGF antibodies on HB-EGF_Ba/F3 cells (lower); the vertical axis shows the amount of chromium released from the cells due to ADCC-mediated or CDC-mediated cytotoxicity.

PREFERRED EMBODIMENT OF THE INVENTION

The molecular forms of HB-EGF

HB-EGF is a growth factor that belongs to the EGF ligand family; the sequence of the gene encoding human HB-EGF is disclosed as GenBank accession number NM_001945 (SEQ ID NO: 49) and the amino acid sequence of HB-EGF is disclosed as GenBank accession number NP_001936 (SEQ ID NO: 50). Within the context of the present invention, "HB-EGF protein" is a term that encompasses both the full-length protein and fragments thereof. Within the context of the present invention, a "fragment" is a polypeptide that contains any region of the HB-EGF protein, wherein the fragment may not exhibit the functionality of the naturally occurring HB-EGF protein.

sHB-EGF, which is used herein as a specific embodiment of a fragment, is a molecule composed of 73 to 87 amino acid residues and is produced in vivo when the proHB-EGF expressed on the cell surface of an HB-EGF-expressing cell is subjected to protease cleavage in a process known as ectodomain shedding. Multiple sHB-EGF molecules are known; these sHB-EGF molecules have a structure in which the carboxyl terminal is the proline residue at position 149 in the proHB-EGF molecule, with the proHB-EGF molecule being composed of the 208 amino acids shown in SEQ ID NO: 50 while the amino terminal is the asparagine residue at position 63 of the proHB-EGF molecule, the arginine residue at position 73 of the proHB-EGF molecule, the valine residue at position 74 of the proHB-EGF molecule, or the serine residue at position 77 of the proHB-EGF molecule.

The Anti-HB-EGF Antibody

The anti-HB-EGF antibody of the present invention is an antibody that binds to HB-EGF protein, but there are no limitations with regard to its origin (mouse, rat, human, and so forth), type (monoclonal antibody, polyclonal antibody), and configuration (engineered antibodies, low molecular weight antibodies, modified antibodies, and so forth).

The anti-HB-EGF antibody used in the present invention preferably binds specifically to HB-EGF. The anti-HB-EGF antibody used in the present invention is also preferably a monoclonal antibody.

Antibody that has an internalizing activity is a preferred embodiment of the antibody used in the present invention. The "antibody that has an internalizing activity" denotes antibody that is transported into the cell (into the cytoplasm, vesicles, other organelles, and so forth) upon binding to the HB-EGF on the cell surface.

The presence/absence of an internalizing activity by an antibody can be determined using methods known to those skilled in the art. For example, the internalizing activity can be determined by bringing a label-conjugated anti-HB-EGF antibody into contact with HB-EGF-expressing cells and checking the presence/absence of label incorporation into the cell, or by bringing a cytotoxin-conjugated anti-HB-EGF antibody into contact with HB-EGF-expressing cells and checking whether or not cell death has been induced in the HB-EGF-expressing cells. In more specific terms, the presence/absence of an internalizing activity by the antibody can be determined, for example, by the method described in the examples provided below.

In those instances in which the anti-HB-EGF antibody has an internalizing activity, the anti-HB-EGF antibody is preferably an antibody capable of binding proHB-EGF and more preferably is an antibody that binds to proHB-EGF more strongly than to sHB-EGF.

The Cytotoxic Substance

Another preferred embodiment of the antibody used in the present invention is an antibody to which a cytotoxic substance is attached. Such a cytotoxic substance-conjugated antibody may be incorporated into a cell, resulting in the cytotoxic substance-mediated induction of the death of the cell that has incorporated the antibody. Accordingly, the cytotoxic substance-conjugated antibody preferably also has an internalizing activity.

The cytotoxic substance used in the present invention may be any substance that can induce cell death in a cell and may include toxins, radioactive substances, chemotherapeutic agents, and so forth. The cytotoxic substance used in the present invention encompasses prodrugs that undergo alteration in vivo to an active cytotoxic substance. The prodrug activation may proceed via an enzymatic alteration or a nonenzymatic alteration.

Within the context of the present invention, toxin denotes various cytotoxic proteins polypeptides, and so forth, of microbial, animal, or plant origin. The toxins used in the present invention may include the following: diphtheria toxin A chain (Langone J. J. et al., *Methods in Enzymology*, 93, 307-308, 1983), pseudomonas exotoxin (*Nature Medicine*, 2, 350-353, 1996), ricin A chain (Fulton R. J. et al., *J. Biol. Chem.*, 261, 5314-5319, 1986; Sivam G., et al., *Cancer Res.*, 47, 3169-3173, 1987; Cumber A. J. et al., *J. Immunol. Methods*, 135, 15-24, 1990; Wawrzynczak E. J. et al., *Cancer Res.*, 50, 7519-7562, 1990; Gheeite V. et al., *J. Immunol. Methods*, 142, 223-230, 1991), deglycosylated ricin A chain (Thorpe P. E. et al., *Cancer Res.*, 47, 5924-5931, 1987), abrin A chain (Wawrzynczak E. J. et al., *Br. J. Cancer*, 66, 361-366, 1992; Wawrzynczak E. J. et al., *Cancer Res.*, 50, 7519-7562, 1990; Sivam G. et al., *Cancer Res.*, 47, 3169-3173, 1987; Thorpe P. E. et al., *Cancer Res.*, 47, 5924-5931, 1987), gelonin (Sivam G. et al., *Cancer Res.*, 47, 3169-3173, 1987; Cumber A. J. et al., *J. Immunol. Methods*, 135, 15-24, 1990; Wawrzynczak E. J. et al., *Cancer Res.*, 50, 7519-7562, 1990; Bolognesi A. et al., *Clin. Exp. Immunol.*, 89, 341-346, 1992), PAP-s (pokeweed anti-viral protein from seeds; Bolognesi A. et al., *Clin. Exp. Immunol.*, 89, 341-346, 1992), briodin (Bolognesi A. et al., *Clin. Exp. Immunol.*, 89, 341-346, 1992), saporin (Bolognesi A. et al., *Clin. Exp. Immunol.*, 89, 341-346, 1992), momordin (Cumber A. J. et al., *J. Immunol. Methods*, 135, 15-24, 1990; Wawrzynczak E. J. et al., *Cancer Res.*, 50, 7519-7562, 1990; Bolognesi A. et al., *Clin. Exp. Immunol.*, 89, 341-346, 1992), momorcochin (Bolognesi A. et al., *Clin. Exp. Immunol.*, 89, 341-346, 1992), dianthin 32 (Bolognesi A. et al., *Clin. Exp. Immunol.*, 89, 341-346, 1992), dianthin 30 (Stirpe F., Barbieri L., *FEBS Letter*, 195, 1-8, 1986), modeccin (Stirpe F., Barbieri L., *FEBS Letter*, 195, 1-8, 1986), viscumin (Stirpe F., Barbieri L., *FEBS Letter*, 195, 1-8, 1986), volkesin (Stirpe F., Barbieri L., *FEBS Letter*, 195, 1-8, 1986), dodecandrin (Stirpe F., Barbieri L., *FEBS Letter*, 195, 1-8, 1986), tritin (Stirpe F., Barbieri L., *FEBS Letter*, 195, 1-8, 1986), luffin (Stirpe F., Barbieri L., *FEBS Letter*, 195, 1-8, 1986), and trichokirin (Casellas P., et al., *Eur. J. Biochem.*, 176, 581-588, 1988; Bolognesi A. et al., *Clin. Exp. Immunol.*, 89, 341-346, 1992).

The radioactive substance in the present invention denotes a substance that contains a radioisotope. There are no particular limitations on the radioisotope and any radioisotope may be used. Examples of usable radioisotopes are $^{32}P$, $^{14}C$, $^{125}I$, $^{3}H$, $^{131}I$, $^{186}Re$, $^{188}Re$, and so forth.

The chemotherapeutic agent in the present invention denotes a cytotoxic substance other than the toxin and radioactive substance cited above and encompasses, for example, cytokines, antitumor agents, enzymes, and for forth. The chemotherapeutic agent used in the present invention is not particularly limited, but is preferably a low molecular weight chemotherapeutic agent. At low molecular weights, the chemotherapeutic agent is believed to have a low potential for interfering with antibody function even after the chemotherapeutic agent has been bound to the antibody. Within the context of the present invention, low molecular weight chemotherapeutic agents generally denote a molecular weight of 100 to 2000 and preferably a molecular weight of 200 to 1000. There are no particular limitations in the present invention on the chemotherapeutic agent, and examples of usable chemotherapeutic agents are as follows: melphalan (Rowland G. F. et al., *Nature*, 255, 487-488, 1975), cis-platinum (Hurwitz E. and Haimovich J., *Method in Enzymology*, 178, 369-375, 1986; Schechter B. et al., *Int. J. Cancer*, 48, 167-172, 1991), carboplatin (Ota Y. et al., *Asia-Oceania J. Obstet. Gynaecol.*, 19, 449-457, 1993), mitomycin C (Noguchi A. et al., *Bioconjugate Chem.*, 3, 132-137, 1992), adriamycin (doxorubicin) (Shih L. B. et al., *Cancer Res.*, 51, 4192-4198, 1991; Zhu Z. et al., *Cancer Immunol. Immunother.*, 40, 257-267, 1995; Trail P. A. et al., *Science*, 261, 212-215, 1993; Zhu Z. et al., *Cancer Immunol. Immunother.*, 40, 257-267, 1995; Kondo Y. et al., *Jpn. J. Cancer Res.*, 86, 1072-1079, 1995; Zhu Z. et al., *Cancer Immunol. Immunother.*, 40, 257-267, 1995; Zhu Z. et al., *Cancer Immunol. Immunother.*, 40, 257-267, 1995), daunorubicin (Dillman R. O. et al., *Cancer Res.*, 48, 6097-6102, 1988; Hudecz F. et al., *Bioconjugate Chem.*, 1, 197-204, 1990; Tukada Y. et al., *J. Natl. Cancer Inst.*, 75, 721-729, 1984), bleomycin (Manabe Y. et al., *Biochem. Biophys. Res. Commun.*, 115, 1009-1014, 1983), neocarzinostatin (Kitamura K. et al., *Cancer Immunol. Immunother.*, 36, 177-184, 1993; Yamaguchi T. et al., *Jpn. J. Cancer Res.*, 85, 167-171, 1994), methotrexate (Kralovec J. et al., *Cancer Immunol. Immunother.*, 29, 293-302, 1989; Kulkarni P. N. et al., *Cancer Res.*, 41, 2700-2706, 1981; Shin L. B. et al., *Int. J. Cancer*, 41, 832-839, 1988; Gamett M. C. et al., *Int. J. Cancer*, 31, 661-670, 1983), 5-fluorouridine (Shin L. B. *Int. J. Cancer*, 46, 1101-1106, 1990), 5-fluoro-2'-deoxyuridine (Goerlach A. et al., *Bioconjugate Chem.*, 2, 96-101, 1991), cytosine arabinoside (Hurwitz E. et al., *J. Med. Chem.*, 28, 137-140, 1985), aminopterin (Kanellos J. et al., *Immunol. Cell. Biol.*, 65, 483-493, 1987), vincristine (Johnson J. R. et al., *Br. J. Cancer*, 42, 17, 1980), vindesine (Johnson J. R. et al., *Br. J. Cancer*, 44, 472-475, 1981), interleukin 2 (IL-2), tumor necrosis factor α (TNFα), interferon (INF), carboxypeptidase, alkaline phosphatase, β-lactamase, and cytidine deaminase.

The present invention may use a single cytotoxic substance or a combination of two or more cytotoxic substances.

The aforementioned cytotoxic substances can be bound or conjugated to the anti-HB-EGF antibody by covalent bond or noncovalent bond. Methods for producing antibody conjugated with these cytotoxic substances are known.

The cytotoxic substance may be directly bound to the anti-HB-EGF antibody through, for example, linking groups present on these species themselves, or may be indirectly bound to the anti-HB-EGF antibody through another substance, for example, a linker or intermediary support. The linking group in the case of direct bonding between the anti-HB-EGF antibody and the cytotoxic substance include the disulfide bond, which is based on the utilization of SH groups. In specific terms, an intramolecular disulfide bond in the Fc region of the antibody can be reduced with a reducing agent such as, for example, dithiothreitol; a disulfide bond in the cytotoxic substance can be similarly reduced; and the two species can then be linked to each other by a disulfide bond. The formation of the disulfide bond between the two species may be promoted by preliminary activating either the antibody or the cytotoxic substance with an activation promoter, for example, Ellman's reagent. Examples of other methods for implementing direct bonding between the anti-HB-EGF antibody and the cytotoxic substance are as follows: methods that use a Schiff base, carbodiimide methods, active ester methods (N-hydroxysucccinimide method), methods that use a mixed anhydride, and methods that use the diazo reaction.

Binding between the anti-HB-EGF antibody and cytotoxic substance can also occur by indirect binding through another substance. There are no particular limitations on the other substances employed for indirect binding, and the other substance may include compounds that have at least two groups—comprising a single type or a combination of two or more types—selected from the amino group, carboxyl group, mercapto group, and so forth, and may also include peptide linkers and compounds that have the ability to bind to the anti-HB-EGF antibody. The following are examples of compounds that have at least two groups—comprising a single type or a combination of two or more types—selected from the amino group, carboxyl group, mercapto group, and so forth: N-succinimidyl 3-(2-pyridyldithio)propionate (SPDP; Wawrzynczak E. J. et al., *Cancer Res.*, 50, 7519-7562, 1990; Thorpe P. E. et al., *Cancer Res.*, 47, 5924-5931, 1987), succinimidyl 6-3-[2-pyridyldithio]propionamido)hexanoate (LC-SPDP; Hermanson G. T., *BIOCONJUGATE Techniques*, 230-232, 1996), sulfosuccinimidyl 6-(3-[2-pyridyldithio] propionamido)hexanoate (sulfo-LC-SPDP; Hermanson G. T., *BIOCONJUGATE Techniques*, 230-232, 1996), N-succinimidyl 3-(2-pyridyldithio)butyrate (SPDB; Wawrzynczak E. J. et al., *Br. J. Cancer*, 66, 361-366, 1992), succinimidyloxycarbonyl-α-(2-pyridyldithio)toluene (SMPT; Thorpe P. E. et al., *Cancer Res.*, 47, 5924-5931, 1987), succinimidyl 6-(α-methyl-[2-pyridylditio]toluamide)hexanoate (LC-SMPT; Hermanson G. T., *BIOCONJUGATE Techniques*, 232-235, 1996), sulfosuccinimidyl 6-(a-methyl-[2-pyridyldithio] toluamide)hexanoate (sulfo-LC-SMPT; Hermanson G. T., BIOCONJUGATE Techniques, 232-235, 1996), succinimidyl-4-(p-maleimidophenyl)butyrate (SMPB; Hermanson G. T., *BIOCONJUGATE Techniques*, 242-243, 1996), sulfo-succinimidyl-4-(p-maleimidophenyl)butyrate (sulfo-SMPB; Hermanson G. T., *BIOCONJUGATE Techniques*, 242-243, 1996), m-maleimidobenzoyl-N-hydroxysuccinimide ester (MBS; Hermanson G. T., *BIOCONJUGATE Techniques*, 237-238, 1996), m-maleimidobenzoyl-N-hydroxysulfosuccinimide ester (sulfo-MBS; Hermanson G. T., *BIOCONJU-GATE Techniques*, 237-238, 1996), S-acetyl mercaptosuccinic anhydride (SAMSA; Casellas P. et al., *Eur. J. Biochem.*, 176, 581-588, 1988), dimethyl 3,3'-dithiobispropionimidate (DTBP; Casellas P. et al., *Eur. J. Biochem.*, 176, 581-588, 1988), 2-iminothiolane (Thorpe P. E. et al., Cancer Res., 47, 5924-5931, 1987), and so forth.

Examples of other substances that can be used to bind the cytotoxic substance to the anti-HB-EGF antibody are peptides, antibodies, poly-L-glutamic acid (PGA), carboxymethyl dextran, dextran, aminodextran, avidin-biotin, cis-aconitic acid, glutamic acid dihydrazide, human serum albumin (HSA), and so forth.

Moreover, a cytotoxic protein can also be attached to the antibody by genetic engineering techniques. As a specific example, DNA encoding a cytotoxic peptide as described above can be fused in-frame with DNA encoding the anti-HB-EGF antibody and a recombinant vector can be constructed by incorporation into an expression vector. The vector can be transfected into a suitable host cell, and the resulting transformed cells can be cultured to express the incorporated DNA and obtain a fusion protein comprising the anti-HB-EGF antibody to which the toxic peptide is attached. In those instances where a fusion protein with an antibody is prepared, the drug protein or protein toxin is generally positioned on the C-terminal side of the antibody. In addition, a peptide linker can be interposed between the antibody and the drug protein or protein toxin.

The Neutralizing Activity

The anti-HB-EGF antibody used in the present invention may have a neutralizing activity.

A neutralizing activity generally refers to the ability to inhibit the biological activity of a ligand that exhibits biological activity on a cell, with an agonist being an example of such a ligand. Thus, a substance that has a neutralizing activity denotes a substance that binds to such a ligand—or to the receptor that binds the ligand—and thereby inhibits binding by the ligand or by the receptor. The receptor prevented from binding with the ligand as a consequence of the neutralizing activity is then unable to manifest the biological activity that proceeds through the receptor. An antibody that exhibits such a neutralizing activity is generally known as a neutralizing antibody. The neutralizing activity of a particular test substance can be measured by comparing the biological activity in the presence of the ligand and the test substance with the biological activity in the presence of the ligand and the absence of the test substance.

The EGF receptor is considered to be the principal receptor for the HB-EGF described herein. In this case, a dimer is formed due to binding by the ligand and a tyrosine kinase, which is its own domain within the cell, is thereby activated. The activated tyrosine kinase causes the formation by autophosphorylation of phosphorylated tyrosine-containing peptide, with which various signal transduction accessory molecules associate. These are principally PLCγ (phospholipase Cγ), Shc, Grb2, and so forth. Among these accessory molecules, the former two are additionally phosphorylated by the tyrosine kinase of the EGF receptor. The principal pathway in signal transduction from the EGF receptor is a pathway in which phosphorylation is transduced in the sequence Shc, Grb2, Sos, Ras, Raf/MAPK kinase/MAP kinase. A pathway from PLCγ to PKC, which is a secondary pathway, is additionally thought to be present. This intracellular signal cascade is different in each cell type, and therefore a suitable target molecule can be established for each desired target cell. There is no limitation to the factors cited above. The neutralizing activity can be evaluated by measuring in vivo signal activation. Commercially available kits for measuring in vivo signal activation can be suitably used (for example, the protein kinase C activation measurement system from GE Healthcare Biosciences).

In vivo signal activation can also be detected by focusing on the induction of transcription for a target gene that is present downstream in the in vivo signal cascade. Changes in the transcription activity for a target gene can be detected using the reporter assay concept. In specific terms, a reporter gene (e.g., green fluorescence protein (GFP) or luciferase) can be disposed downstream from the transcription factor or promoter region of the target gene, and by measuring the reporter activity the change in transcription activity can be measured in terms of the reporter activity.

In addition, since signal transduction through the EGF receptor generally acts in the direction of promoting cell growth, the neutralizing activity can be evaluated by measuring the growth activity of a target cell.

Antibody that possesses both a neutralizing activity and an internalizing activity can be a very effective anti-cancer agent for cancers that strongly express HB-EGF.

The ADCC Activity and/or CDC Activity

The anti-HB-EGF antibody used in the present invention may have an antibody-dependent cell-mediated cytotoxicity (ADCC) and/or a complement-dependent cytotoxicity (CDC).

In the present invention, the CDC activity refers to a cell-destroying activity due to the complement system. The ADCC activity, on the other hand, refers to an activity in which a specific antibody attaches to a cell surface antigen on a target cell, an Fcγ receptor-presenting cell (immune cell and so forth) binds through its Fcγ receptor to the Fc region of the antigen-bound antibody, and the target cell is then attacked.

Known methods can be used in the present invention to measure whether an antibody exhibits ADCC activity and whether an antibody exhibits CDC activity (For example, Current Protocols in Immunology. Chapter 7: Immunologic Studies in Humans. Editor: John E. Coligan et al., John Wiley & Sons, Inc. (1993), and so forth).

In specific terms, effector cells, a complement solution, and target cells are first prepared.

(1) Preparation of the Effector Cells

The spleen is removed from, for example, CBA/N mice, and the splenocytes are separated in RPMI1640 medium (Invitrogen Corporation). The effector cells can then be prepared by washing with the same medium containing 10% fetal bovine serum (FBS, HyClone) and subsequently adjusting the cell concentration to $5 \times 10^6$/mL.

(2) Preparation of the Complement Solution

The complement solution can be prepared by diluting baby rabbit complement (Cedarlane Laboratories Ltd.) 10 times with medium containing 10% FBS (Invitrogen Corporation).

(3) Preparation of the Target Cells

Cells that express HB-EGF protein are cultured with 0.2 mCi $^{51}$Cr$^-$ sodium chromate (GE Healthcare Biosciences) for 1 hour at 37° C. on DMEM medium containing 10% FBS in order to radiolabel these target cells. For example, cancer cells (e.g., ovarian cancer cells) or cells transformed with an HB-EGF protein-encoding gene can be used as the HB-EGF protein-expressing cells. After radiolabeling, the cells are washed 3 times with RPMI1640 medium containing 10% FBS and the target cells are prepared by adjusting the cell concentration to $2 \times 10^5$/mL.

The ADCC activity and CDC activity can be measured by the following methods. In order to measure the ADCC activity, 50 μL target cells and 50 μL anti-HB-EGF antibody are added to a 96-well U-bottom plate (Becton, Dickinson and Company) and a reacted for 15 minutes on ice. Then 100 μL effector cells is added and incubated for 4 hours in a $CO_2$ incubator. A final antibody concentration of 0 or 10 μg/mL is employed. After incubation, 100 μL of the supernatant is recovered and the radioactivity is measured with a gamma counter (COBRA II AUTO-GAMMA, MODEL D5005, Packard Instrument Company). Using the obtained values, the cytotoxic activity (%) can be calculated from the formula $(A-C)/(B-C) \times 100$ where A is the radioactivity (cpm) in the particular sample, B is the radioactivity (cpm) in a sample to which 1% NP-40 (Nacalai Tesque, Inc.) has been added, and C is the radioactivity (cpm) of a sample containing only the target cells.

When, on the other hand, the CDC activity is to be measured, 50 μL target cells and 50 μL anti-HB-EGF antibody are added to a 96-well flat-bottom plate (Becton, Dickinson and Company) and a reacted for 15 minutes on ice. This is followed by the addition of 100 μL complement solution and incubation for 4 hours in a $CO_2$ incubator. A final antibody concentration of 0 or 3 μg/mL is employed. After incubation, 100 μL supernatant is recovered and the radioactivity is measured with a gamma counter. The cytotoxic activity can be calculated in the same manner as for measurement of the ADCC activity.

Antibody that possesses both an internalizing activity and an ADCC activity and/or a CDC activity can be a very effective anti-cancer agent for cancers that strongly express HB-EGF. In addition, antibody that possesses both a neutralizing activity and an ADCC activity and/or a CDC activity can be a very effective anti-cancer agent for cancers that strongly express HB-EGF. Moreover, antibody that possesses an internalizing activity plus a neutralizing activity plus an ADCC activity and/or a CDC activity can be a very effective anti-cancer agent for cancers that strongly express HB-EGF.

Antibody Production

Monoclonal anti-HB-EGF antibody according to the present invention can be obtained using known means. Monoclonal antibody of mammalian origin is particularly preferred for the anti-HB-EGF antibody of the present invention. The monoclonal antibody of mammalian origin encompasses, inter alia, monoclonal antibody produced by a hybridoma and monoclonal antibody produced by a host that has been transformed by genetic engineering techniques with an expression vector that comprises the antibody gene.

Monoclonal antibody-producing hybridomas can be prepared using known technology, for example, as described in the following. First an animal is immunized with HB-EGF protein as the sensitizing antigen according to the usual immunization methods. Immune cells obtained from the immunized animal are fused with a known partner cell by the usual cell fusion techniques to obtain hybridomas. Using the usual screening techniques, these hybridomas can be subjected to the selection of hybridomas that produce anti-HB-EGF antibody by screening for cells that produce the desired antibody.

In specific terms, monoclonal antibody production can be carried out, for example, as follows. First, the HB-EGF protein used as the sensitizing antigen for antibody acquisition can be obtained by the expression of an HB-EGF gene. The base sequence of the human HB-EGF gene is disclosed, for example, as GenBank accession number NM_001945 (SEQ ID NO: 49). Thus, the gene sequence encoding HB-EGF is inserted into a known expression vector and a suitable host cell is then transformed with the expression vector; the desired human HB-EGF protein can subsequently be purified from within the host cells or from the culture supernatant. Purified natural HB-EGF protein can also be used in the same manner. The protein may be purified using one or a combination of the usual chromatographic techniques, e.g., ion chromatography, affinity chromatography, and so forth, using a single run or a plurality of runs. The immunogen used in the present invention can also be a fusion protein as obtained by fusion of a desired partial polypeptide from the HB-EGF protein with a different polypeptide. For example, a peptide tag or the Fc fragment from the antibody can be used to produce the fusion protein that will be used as the immunogen. A vector that expresses the fusion protein can be prepared by in-frame fusion of the genes encoding the desired two or more polypeptide fragments and insertion of the fused gene into an expression vector as described above. Methods for producing fusion proteins are described in Molecular Cloning 2nd Edt. (Sambrook, J. et al., Molecular Cloning 2nd Edt., 9.47-9.58, Cold Spring Harbor Laboratory Press, 1989).

The HB-EGF protein purified in the described manner can be employed as the sensitizing antigen used to immunize a mammal. A partial peptide from HB-EGF can also be used as the sensitizing antigen. For example, the following peptides can be used as the sensitizing antigen:

peptide obtained from the amino acid sequence for human HB-EGF by chemical synthesis;

peptide obtained by incorporating a portion of the human HB-EGF gene into an expression vector and expressing same; and peptide obtained by degradation of human HB-EGF protein with a protein degrading enzyme.

There are no limitations on the HB-EGF region used as the partial peptide or on the size of the partial peptide. A preferred region can be selected from the amino acid sequence constituting the extracellular domain of HB-EGF (positions 22 to 149 in the amino acid sequence of SEQ ID NO: 50). The number of amino acids making up the peptide that will be used as the sensitizing antigen is preferably at least 3, for example, at least 5 or at least 6. More specifically, a peptide of 8 to 50 residues and preferably 10 to 30 residues can be used as the sensitizing antigen.

There are no particular limitations on the mammal that may be immunized by the sensitizing antigen described above. In order to obtain monoclonal antibody by cell fusion techniques, the immunized animal is preferably selected considering the compatibility with the partner cell that will be used in cell fusion. Rodents are generally preferred as the immunized animal. Specifically, the mouse, rat, hamster, or rabbit can be used as the immunized animal. Monkeys can also be used as the immunized animal.

The animal as described above can be immunized with the sensitizing antigen according to known methods. For example, as a general method, the mammal can be immunized by subcutaneous or intraperitoneal injection of the sensitizing antigen. In specific terms, the sensitizing antigen may be administered to the mammal a plurality times on a 4 to 21 day schedule. The sensitizing antigen is used diluted to a suitable dilution factor with, for example, phosphate-buffered saline (PBS) or physiological saline. The sensitizing antigen may also be administered in combination with an adjuvant. For example, the sensitizing antigen can be prepared by mixing and emulsification with Freund's complete adjuvant. A suitable carrier can also be used in immunization with the sensitizing antigen. Particularly in those instances in which a low molecular weight partial peptide is used as the sensitizing antigen, immunization is desirably effected with the sensitizing peptide antigen conjugated with a protein carrier, e.g., albumin, keyhole limpet hemocyanin, and so forth.

After the mammal is immunized in the described manner and a desired rise in the serum antibody titer is observed, immune cells are collected from the mammal and are submitted to cell fusion. Splenocytes in particular are preferred immune cells.

Mammalian myeloma cells are used as the cells for fusion with the above-described immune cells. The myeloma cells are preferably provided with a suitable selection marker to support screening. The selection marker denotes a trait that can appear (or that cannot appear) under specific culture conditions. Known selection markers include hypoxanthine-guanine-phosphoribosyltransferase deficiency (abbreviated below as HGPRT deficiency) and thymidine kinase deficiency (abbreviated below as TK deficiency). Cells that are HGPRT- or TK-deficient exhibit hypoxanthine-aminopterin-thymidine sensitivity (abbreviated below as HAT sensitivity). HAT-sensitive cells are unable to undergo DNA synthesis on an HAT selection medium and die; however, when fused with a normal cell, DNA synthesis can continue using the salvage pathway of the normal cell and growth can also occur on HAT selection medium.

HGPRT-deficient cells can be selected on a medium containing 6-thioguanine or 8-azaguanine (8AG), while TK-deficient cells can be selected on a medium containing 5'-bromodeoxyuridine. Normal cells incorporate these pyrimidine analogues into their DNA and die, while cells deficient in these enzymes do not incorporate these pyrimidine analogs and are able to survive on the selection medium. Another selection marker, known as G418 resistance, imparts resistance to 2-deoxystreptamine-type antibiotics (gentamycin analogues) based on the neomycin resistance gene. Various myeloma cells suitable for cell fusion are known. For example, the following myeloma cells can be employed: P3 (P3×63Ag8.653) (*J. Immunol.* (1979) 123, 1548-1550), P3×63Ag8U.1 (*Current Topics in Microbiology and Immunology* (1978) 81, 1-7), NS-1 (Kohler, G. and Milstein, C. *Eur. J. Immunol.* (1976) 6, 511-519), MPC-11 (Margulies, D. H. et al., *Cell* (1976) 8, 405-415), SP2/0 (Shulman, M. et al., *Nature* (1978) 276, 269-270), FO (de St. Groth, S. F. et al., *J. Immunol. Methods* (1980) 35, 1-21), S194 (Trowbridge, I. S. *J. Exp. Med.* (1978) 148, 313-323), and R210 (Galfre, G. et al., *Nature* (1979) 277, 131-133).

Cell fusion between the above-described immune cells and myeloma cells can be carried out according to known methods, for example, according to the method of Kohler and Milstein (Kohler, G. and Milstein, C., *Methods Enzymol.* (1981) 73, 3-46).

More specifically, cell fusion can be carried out, for example, in the usual nutrient culture fluids in the presence of a cell fusion promoter. For example, polyethylene glycol (PEG) or Sendai virus (HVJ) can be used as the fusion promoter. As desired, an auxiliary such as dimethyl sulfoxide can be added in order to boost the fusion efficiency.

The ratio between the immune cells and the myeloma cells can be freely selected. For example, the immune cells are preferably used at from 1× to 10× with respect to the myeloma cells. The culture fluid used for cell fusion can be, for example, RPMI1640 culture medium or MEM culture medium, which are very suitable for the growth of the previously cited myeloma cell lines, or the usual culture media used for this type of cell culture. A serum supplement such as fetal calf serum (FCS) can also be added to the culture medium.

The desired fused cells (hybridomas) are formed by cell fusion by thoroughly mixing prescribed quantities of the immune cells and myeloma cells in a culture fluid as described above and admixing a PEG solution that has been preheated to about 37° C. For example, PEG with an average molecular weight of 1000 to 6000 can be added to the cell fusion process at a concentration generally from 30 to 60% (w/v). Then, the cell fusion agents and so forth that are undesirable for hybridoma growth are removed by repeating the process of adding a suitable culture fluid as described above, centrifuging, and removing the supernatant.

The hybridomas obtained in the described manner can be selected by using a selection medium adapted to the selection markers exhibited by the myeloma used for cell fusion. For example, HGPRT- or TK-deficient cells can be selected by culture on HAT medium (medium containing hypoxanthine, aminopterin, and thymidine). Thus, when HAT-sensitive myeloma cells are used for cell fusion, cells resulting from cell fusion with the normal cells can selectively grow on the HAT medium. Culture on the HAT medium is continued for a period of time sufficient for cells (unfused cells) other than the desired hybridomas to die. In specific terms, the desired hybridomas can be selected generally by culture for from several days to several weeks. The usual limit dilution process can be used for screening and monocloning of hybridomas that produce the desired antibody. Or, antibody that recognizes HB-EGF can also be produced by the method described in WO 03/104453.

Screening for and monocloning the desired antibody can be suitably carried out by a screening procedure based on known antigen-antibody reactions. For example, an antigen may be bound to a carrier (e.g., beads of, for example, polystyrene, or a commercial 96-well microtiter plate) and then reacted with hybridoma culture supernatant. Then, after the carrier has been washed, the cells are reacted with, for example, an enzyme-labeled secondary antibody. If the desired sensitizing antigen-reactive antibody was present in the culture supernatant, the secondary antibody will bind to the carrier through the antibody. The presence/absence of the desired antibody in the culture supernatant can finally be established by detection of the secondary antibody that is bound to the carrier. A hybridoma that produces the desired antigen-binding antibody can be cloned, for example, by the limit dilution method. Here, substantially the same HB-EGF protein is suitably used as the antigen, including those used for immunization. For example, an oligopeptide comprising the extracellular domain of HB-EGF—or comprising a partial amino acid sequence from that region—can be used as the antigen.

In addition to the above-described method of producing a hybridoma by immunizing a nonhuman animal with antigen, the desired antibody can also be obtained by the antigenic sensitization of human lymphocytes. In specific terms, human lymphocytes are first sensitized in vitro with HB-EGF protein. The immunosensitized lymphocytes are then fused with a suitable fusion partner. For example, myeloma cells of human origin having a permanent cell division ability can be used as the fusion partner (refer to Japanese Patent Publication No. H1-59878). The anti-HB-EGF antibody obtained by this method is a human antibody that has the activity to bind to HB-EGF protein.

Human anti-HB-EGF antibody can also be obtained by administering HB-EGF protein as antigen to a transgenic animal that has the entire human antibody gene repertoire. Antibody-producing cells from the immunized animal can be immortalized by cell fusion with a suitable fusion partner or by a treatment such as infection with the Epstein-Barr virus. Human antibody to the HB-EGF protein can be isolated from the resulting immortalized cells (refer to International Publications WO 94/25585, WO 93/12227, WO 92/03918, and WO 94/02602). Moreover, cells that produce antibody having the desired reaction specificity can also be cloned by cloning the immortalized cells. When a transgenic animal is employed as the immunized animal, the animal's immune system recognizes human HB-EGF as foreign. This makes it possible to readily obtain human antibody directed against human HB-EGF. The monoclonal antibody-producing hybridoma constructed in the described manner can be subcultured in the usual culture media. Long-term storage of the hybridoma in liquid nitrogen is also possible.

The aforementioned hybridoma can be cultured according to the usual methods and the desired monoclonal antibody can be obtained from the resulting culture supernatant. Or, the hybridoma can be injected to a mammal compatible with the cells and monoclonal antibody can be obtained from the ascites fluid of the mammal. The former method is well suited for the production of high-purity antibody.

The present invention can also use antibody encoded by an antibody gene that has been cloned from an antibody-producing cell. Antibody expression can be achieved by incorporating the cloned antibody gene into a suitable vector followed by transfection into a host. Methods have already been established for isolating the antibody gene and inserting it into a vector and for transforming the host cell (refer, for example, to Vandamme, A. M. et al., *Eur. J. Biochem.* (1990) 192, 767-775).

For example, cDNA encoding the variable region (V region) of the anti-HB-EGF antibody can be obtained from a hybridoma cell that produces anti-HB-EGF antibody. The total RNA is typically first extracted from the hybridoma. Methods that can be used to extract the mRNA from cells are, for example, the guanidine ultracentrifugal method (Chirgwin, J. M. et al., *Biochemistry* (1979) 18, 5294-5299) and the AGPC method (Chomczynski, P. et al., *Anal. Biochem.* (1987) 162, 156-159).

The extracted mRNA can be purified using, for example, an mRNA Purification Kit (GE Healthcare Biosciences). Or, kits for the direct extraction of the total mRNA from cells are also commercially available, such as the QuickPrep mRNA Purification Kit (GE Healthcare Biosciences). Kits such as these can also be used to obtain the total mRNA from hybridomas. cDNA encoding the antibody V region can be synthesized from the obtained mRNA using a reverse transcriptase. The cDNA can be synthesized with, for example, an AMV Reverse Transcriptase First-Strand cDNA Synthesis Kit (Seikagaku Corporation). In addition, a 5'-Ampli FINDER RACE Kit (Clontech) and the PCR-based 5'-RACE method (Frohman, M. A. et al., *Proc. Natl. Acad. Sci. USA* (1988) 85, 8998-9002; Belyaysky, A., et al., *Nucleic Acids Res.* (1989) 17, 2919-2932) can be used to synthesize and amplify the cDNA. Moreover, suitable restriction enzyme sites, infra, can be introduced at both ends of the cDNA in such a cDNA synthesis procedure.

The target cDNA fragment is purified from the obtained PCR product and is then ligated with vector DNA; the recombinant vector fabricated in this manner is transfected into, for example, *E. coli*, and colonies are selected; and the desired recombinant vector can be prepared from the *E. coli* that has exhibited colony formation. In addition, known methods, for example, the dideoxynucleotide chain termination method, can be used to ascertain whether the recombinant vector has the base sequence of the target cDNA.

In order to obtain a gene that encodes the variable region, PCR using variable region gene amplification primers can also be employed. First, cDNA is synthesized using extracted mRNA as the template in order to obtain a cDNA library. A commercially available kit is conveniently used to synthesize the cDNA library. In actuality, the amount of mRNA obtained from only a small number of cells will be quite small, and thus its direct purification provides a low yield. Accordingly, purification is generally carried out after the addition of carrier RNA that clearly does not contain the antibody gene. Or, in those cases in which a certain amount of RNA can be extracted, it may be possible to achieve an efficient extraction even with only the RNA from the antibody-producing cells. For example, in some cases it may not be necessary to add carrier RNA to RNA extraction from at least 10 or at least 30 and preferably at least 50 antibody-producing cells.

Employing the obtained cDNA library as a template, the antibody gene can be amplified by PCR. Primers for the PCR-based amplification of antibody genes are known. For example, primers for the amplification of human antibody genes can be designed based on the information in the literature (for example, *J. Mol. Biol.* (1991) 222, 581-597). These primers have a base sequence that varies with the immunoglobulin subclass. Thus, when a cDNA library of unknown subclass is employed as the template, PCR is carried out considering all of the possibilities.

In specific terms, when the goal is, for example, the acquisition of genes encoding human IgG, primers can be used that have the ability to amplify genes encoding γ1 to γ5 for the heavy chain and the κ chain and λ chain for the light chain. In order to amplify the IgG variable region gene, a primer that anneals to the region corresponding to the hinge region is ordinarily used for the 3'-side primer. On the other hand, a primer adapted for each subclass can be used for the 5'-side primer.

The PCR products based on gene amplification primers for each heavy chain and light chain subclass are made as respective independent libraries. Using the libraries thus synthesized, immunoglobulin comprising a heavy chain plus light chain combination can be reconstructed. The desired antibody may be screened using as an indicator the binding activity of the reconstructed immunoglobulin for HB-EGF.

Binding by the antibody of the present invention to HB-EGF is more preferably specific binding. Screening for antibody that binds HB-EGF can be carried out, for example, by the following steps:
(1) bringing HB-EGF into contact with antibody comprising a V region encoded by cDNA obtained from a hybridoma;
(2) detecting binding between the HB-EGF and the antibody; and
(3) selecting antibody that binds to the HB-EGF.

Methods of detecting binding between an antibody and HB-EGF are known. In specific terms, the test antibody may be reacted with HB-EGF that has been immobilized on a carrier and then reacted with a labeled antibody that recognizes the antibody. When, after washing, the labeled antibody can be detected on the carrier as an indicator of binding of the test antibody to the HB-EGF. A fluorescent substance such as FITC or an enzymatic protein such as peroxidase or β-galactoside can be used for the label. HB-EGF-expressing cells in immobilized form can also be used to evaluate the antibody's binding activity.

Panning using a phage vector can also be employed as a method of antibody screening using binding activity as the indicator. Screening using a phage vector is advantageous when as described above the antibody genes are obtained as heavy chain subclass and light chain subclass libraries. The genes encoding the heavy chain and light chain variable regions can be made into a single-chain Fv (scFv) by linking with a suitable linker sequence. The scFv-encoding gene may be inserted into a phage vector to obtain a phage that expresses scFv on its surface. The phage is brought into contact with the target antigen, and the recovery of phage that was bound to the antigen enables the recovery of DNA coding for scFv that has the desired binding activity. scFv having the desired binding activity can be enriched by repeating this process as necessary.

In the present invention, antibody-encoding polynucleotide may encode the full length of the antibody or may encode a portion of the antibody. This portion of the antibody may be any portion of the antibody molecule. Antibody fragment is a term used below in some instances to indicate a portion of an antibody. Preferred antibody fragments in the present invention comprise the complementarity determination region (CDR). A more preferred antibody fragment in the present invention comprises all of the three CDRs that constitute the variable region.

Once the cDNA encoding the V region of the target anti-HB-EGF antibody has been obtained, cDNA is digested by restriction enzymes that recognize the restriction enzyme sites that have been inserted at both ends of the cDNA. Preferred restriction enzymes will recognize and digest base sequences that have a low potential of occurrence in the base sequence constituting the antibody gene. In order to insert 1 copy of the digestion fragment in the correct direction in the vector, a restriction enzyme that provides cohesive ends is preferred. An antibody expression vector can be obtained by inserting the cDNA encoding the anti-HB-EGF antibody V region, digested as described in the preceding, into a suitable expression vector. At this point, a chimeric antibody can be obtained through the in-frame fusion of a gene encoding the antibody constant region (C region) with the aforementioned V region-encoding gene. Here, chimeric antibody refers to a product having different origins for the constant region and variable region. Accordingly, in the context of the present invention "chimeric antibody" also encompasses human-human allochimeric antibodies in addition to heterochimeric antibodies such as mouse-human. A chimeric antibody expression vector can also be constructed by inserting the aforementioned V region gene into an expression vector that already carries the constant region.

In specific terms, for example, a restriction enzyme recognition sequence for a restriction enzyme used to digest the aforementioned V region gene can be disposed in advance on the 5' side of an expression vector that holds the DNA coding for the desired antibody constant region (C region). Digestion of the two with the same restriction enzyme combination and in-frame fusion results in the construction of a chimeric antibody expression vector.

In order to produce the anti-HB-EGF antibody of the present invention, the antibody gene can be incorporated in the expression vector in such a manner that expression occurs under control by an expression control region. Expression control regions for antibody expression include, for example, enhancers and promoters. Recombinant cells that express DNA coding for anti-HB-EGF antibody can then be obtained by transforming suitable host cells with the expression vector under consideration.

For expression of the antibody gene, the DNA coding for the antibody heavy chain (H chain) and the DNA coding for the antibody light chain (L chain) can be incorporated in separate expression vectors. An antibody molecule provided with H and L chains can be expressed by simultaneously transforming (co-transfect) the same host cell with the vector incorporating the H chain and the vector incorporating the L chain. Or, DNA encoding the H chain and L chain may be incorporated in a single expression vector and the host cell may then be transformed (International Publication WO 94/11523).

Numerous host/expression vector combinations are known for antibody production by isolating temporarily the antibody gene and transfecting a suitable host. Any of these expression systems may be applied to the present invention. Animal cells, plant cells, or fungal cells can be used when eukaryotic cells are used as the host. Specific examples of animal cells that can be used in the present invention are mammalian cells (e.g., CHO, COS, myeloma, baby hamster kidney (BHK), Hela, Vero, and for so forth), amphibian cells (e.g., *Xenopus laevis* oocytes and so forth), and insect cells (e.g., sf9, sf21, Tn5, and so forth).

In the case of plant cells, antibody gene expression systems based on cells from genus *Nicotiana*, e.g., *Nicotiana tabacum* and so forth, are known. Callus-cultured cells can be used for plant cell transformation.

The following, for example, can be used as the fungal cells: yeast (e.g., *Saccharomyces* such as *Saccharomyces cerevisiae*, *Pichia* such as *Pichia pastoris*, and so forth), and filamentous fungi (e.g., *Aspergillus* such as *Aspergillus niger*).

Antibody gene expression systems using prokaryotes are also known. Taking bacteria as an example, bacteria such as *E. coli, Bacillus subtilis*, and so forth, can be used in the present invention.

When a mammalian cell is used, an expression vector can be constructed by functionally ligating an effective, commonly used promoter, the antibody gene that is to be expressed, and a polyA signal downstream at the 3'-terminal of the antibody gene. An example of a promoter/enhancer is the human cytomegalovirus immediate early promoter/enhancer.

Other promoter/enhancers that can be used to express the antibody of the present invention are, for example, viral promoter/enhancers and promoter/enhancers that originate in mammalian cells, such as human elongation factor 1α (HEF1α). Specific examples of viruses that can provide usable promoter/enhancers are retroviruses, polyoma viruses, adenoviruses, and simian virus 40 (SV40).

The SV40 promoter/enhancer can be used according to the method of Mulligan et al. (*Nature* (1979) 277, 108). In addition, the HEF1a promoter/enhancer can be readily utilized for the desired gene expression according to the method of Mizushima et al. (*Nucleic Acids Res.* (1990) 18, 5322).

In the case of *E. coli*, expression of the gene under consideration can be achieved by functionally ligating an effective, commonly used promoter, a signal sequence for antibody secretion, and the antibody gene that is to be expressed. The promoter can be, for example, the lacZ promoter or the araB promoter. The lacZ promoter can be used according to the method of Ward et al. (*Nature* (1989) 341, 544-546; FASEBJ. (1992) 6, 2422-2427). Or, the araB promoter can be used for the desired gene expression according to the method of Better et al. (*Science* (1988) 240, 1041-1043).

With regard to the signal sequence for antibody secretion, the pelB signal sequence (Lei, S. P. et al., *J. Bacteriol.* (1987) 169, 4379) may be used in the case of production in the *E. coli* periplasm. After the antibody produced in the periplasm has been isolated, the antibody structure can be reorganized (refolded)—by the use of a protein denaturant such as the guanidine hydrochloride and urea—so as to exhibit the desired binding activity.

The origin of replication inserted into the expression vector can be, for example, an origin of replication originating in SV40, polyoma virus, adenovirus, bovine papilloma virus (BPV), and so forth. In addition, a selection marker can be inserted in the expression vector for amplification of the gene copy number in the host cell system. In specific terms, usable selection markers are the aminoglycoside transferase (APH) gene, the thymidine kinase (TK) gene, the *E. coli* xanthine-guanine phosphoribosyltransferase (Ecogpt) gene, the dihydrofolate reductase (dhfr) gene, and so forth.

The target antibody can be produced by transfecting the expression vector under consideration into a host cell and culturing the transformed host cell in vitro or in vivo. Host cell culture can be carried out according to known methods. For example, DMEM, MEM, RPMI1640, or IMDM can be used as the culture medium; a serum supplement such as fetal calf serum (FCS) can also be added.

The antibody expressed and produced as described above can be purified by the usual methods known for use for protein purification; a single such method can be used or suitable combinations of these methods can be used. The antibody can be isolated and purified using suitable selections and combinations of, for example, an affinity column (for example, a protein A column), column chromatography, filtration, ultrafiltration, salting out, dialysis, and so forth (Antibodies: A Laboratory Manual. Ed Harlow, David Lane, Cold Spring Harbor Laboratory, 1988).

In addition to host cells as described in the preceding, transgenic animals can also be used to produce recombinant antibodies. That is, the antibody under consideration can be obtained from an animal into which a gene encoding the target antibody has been introduced. For example, a fused gene can be fabricated by the in-frame insertion of the antibody gene within a gene coding for a protein that is natively produced in milk. For example, goat β-casein can be used as the protein secreted into milk. A DNA fragment containing the fused gene that incorporates the antibody gene may be injected into a goat embryo and the injected embryo may be introduced into a female goat. The desired antibody can be obtained as a fusion protein with the milk protein from the milk produced by the transgenic goat (or its offspring) born from the embryo-implanted goat. In addition, hormones can be used as appropriate on the transgenic goat in order to increase the amount of milk containing the desired antibody that is produced from the transgenic goat (Ebert, K. M. et al., Bio/Technology (1994) 12, 699-702).

C regions originating in animal antibodies can be used as the C region of the recombinant antibody of the present invention. The mouse antibody H chain C regions designated Cγ1, Cγ2a, Cγ2b, Cγ3, Cμ, Cδ, Cα1, Cα2, and Cε can be used, and the L chain C regions designated as Cκ and Cλ can be used. Animal antibodies from, for example, the rat, rabbit, goat, sheep, camel, monkey, and so forth, can be used as animal antibodies other than mouse antibodies. These sequences are known. The C region can be modified in order to improve the antibody or improve the stability of its production. When the antibody will be administered to humans, an artificially engineered genetically recombinant antibody can be made in the present invention with the goal, for example, of lowering the foreign antigenicity in the human. Such a genetically recombinant antibody includes, for example, chimeric antibodies and humanized antibodies.

These engineered antibodies can be produced using known methods. A chimeric antibody denotes an antibody in which a variable region is ligated to a constant region that has a different origin from the variable region. For example, an antibody having a heavy chain variable region and a light chain variable region from a mouse antibody and a heavy chain constant region and light chain constant region from a human antibody is a mouse-human-heterochimeric antibody. A recombinant vector that expresses chimeric antibody can be constructed by ligating DNA that encodes mouse antibody variable region to DNA that encodes human antibody constant region and incorporating it into an expression vector. A recombinant cell transformed by the vector is then cultured to bring about expression of the incorporated DNA, and the produced chimeric antibody in the culture medium can then be recovered. The C region of human antibody is used for the C region of chimeric antibodies and humanized antibodies. With regard to the H chain, for example, Cγ1, Cγ2, Cγ3, Cγ4, Cμ, Cδ, Cα1, Cα2, and Cε can be used for the C region. For the L chain, Cκ and Cλ can be used for the C region. The amino acid sequences of these C regions are known, as are the base sequences that code for these amino acid sequences. In addition, the human antibody C region can be modified in order to improve the antibody itself or improve the stability of antibody production.

Chimeric antibodies are generally constructed from the V regions of antibodies of nonhuman animal origin and the C regions of antibodies of human origin. In contrast, a humanized antibody is constructed of complementarity determining regions (CDRs) from antibody of nonhuman animal origin, framework regions (FRs) from antibody of human origin, and C regions from antibody of human origin. Humanized antibodies are useful as active ingredients in therapeutic agents of the present invention with the goal of lowering the antigenicity in the human body.

The variable region of an antibody is typically constructed of three CDRs sandwiched in four FRs. The CDRs are regions that substantially determine the binding specificity of an antibody. The amino acid sequences of CDRs are richly diverse. The amino acid sequences that form the FRs, on the other hand, frequently exhibit high homology even between antibodies that have different binding specificities. Due to this, the binding specificity of a certain antibody can typically be grafted into another antibody by CDR grafting.

Humanized antibodies are also known as reshaped human antibodies. In specific terms, for example, humanized antibodies are known in which the CDRs from a nonhuman animal antibody, such as a mouse antibody, have been grafted into a human antibody. General genetic recombination techniques for obtaining humanized antibodies are also known.

In specific terms, for example, overlap extension PCR is known as a method for grafting mouse antibody CDRs into human FRs. In overlap extension PCR, a base sequence encoding the mouse antibody CDR to be grafted is added to a primer for the synthesis of human antibody FR. Primers are prepared for each of the four FRs. The selection of human FR that exhibits a high homology with mouse FR is generally advantageous for maintenance of CDR function in the grafting of mouse CDR to human FR. Thus, the use is generally preferred of human FR that has an amino acid sequence that exhibits high homology with the amino acid sequence of the FR adjacent to the mouse CDR to be grafted.

In addition, the base sequences that are ligated are designed so as to join with each other in-frame. The human FRs are synthesized separately using primers for each. In this way, products are obtained in which DNA encoding mouse CDR is appended to each FR. The base sequences encoding the mouse CDR in each product are designed so as to overlap with each other. Then, the overlapping CDR regions of the products synthesized with the human antibody gene as a template are annealed to each other and a complementary chain synthesis reaction is carried out. This reaction results in ligation of the human FRs via the mouse CDR sequences.

Finally, the variable region gene comprising four FRs ligated with three CDRs is submitted to full length amplification by annealing, at its 5' end and 3' end, primers to which suitable restriction enzyme recognition sequences have been added. An expression vector for human-type antibody can be constructed by inserting the DNA obtained as described above and DNA encoding a human antibody C region into an expression vector in such a manner that they are fused in-frame. The thus-formulated vector is inserted into a host and a recombinant cell is established; the recombinant cell is cultured to express the DNA encoding the humanized antibody; and humanized antibody is thereby produced in the culture medium of the cultured cells (refer to European paten Publication EP 239,400 and International Publication WO 96/02576).

Human antibody FRs that when ligated across CDRs enable the CDRs to form high-quality antigen binding sites, can be suitably selected by qualitatively or quantitatively measuring and evaluating the binding activity to antigen by humanized antibody that has been constructed as described in the preceding. Amino acid substitution can also be carried out on the FRs as necessary so as to enable the CDRs of the reshaped human antibody to form well-adapted antigen binding sites. For example, mutations in the amino acid sequence can be introduced into an FR using the PCR methodology used to graft mouse CDRs onto human FRs. In specific terms, partial base sequence mutations can be introduced in the primers that are annealed to the FR. Base sequence mutations are then introduced into the FR synthesized using such primers. A mutated FR sequence having the desired properties can be selected by measurement and evaluation, by the methods described above, of the antigen binding activity of the mutated, amino acid-substituted antibody (Sato, K. et al., Cancer Res., 1993, 53, 851-856).

Methods for obtaining human antibodies are also known. For example, human lymphocytes can be sensitized in vitro with a desired antigen or with cells that express a desired antigen. The desired human antibody capable of binding to the antigen can then be obtained by fusing the sensitized lymphocytes with human myeloma cells (refer to Japanese Patent Publication No. H 1-59878). For example, U266 can be used for the human myeloma cell employed as the fusion partner.

A desired human antibody can also be obtained by immunizing a transgenic animal having the entire human antibody gene repertoire with a desired antigen (refer to International Publications WO 93/12227, WO 92/03918, WO 94/02602, WO 94/25585, WO 96/34096, and WO 96/33735). Technology for obtaining human antibodies by panning using a human antibody library are also known. For example, the human antibody V region can be expressed as a single chain antibody (scFv) on the surface of a phage by the phage display method and phage that binds to an antigen can be selected. The DNA sequence that codes for the V region of human antibody that binds the antigen can then be established by analysis of the genes of the selected phage. Once the DNA sequence of the antigen-binding scFv has been established, the V region sequence can be in-frame fused with a sequence for the desired human antibody C region, after which an expression vector can be constructed by insertion in an appropriate expression vector. The expression vector can be transfected into an appropriate expression cell as described above and human antibody can be obtained by expression of the gene coding for the human antibody. These methods are already known (International Publications WO 92/01047, WO 92/20791, WO 93/06213, WO 93/11236, WO 93/19172, WO 95/01438, and WO 95/15388).

Insofar as binding to the HB-EGF protein occurs, the antibody according to the present invention encompasses not only bivalent antibody as typified by IgG, but also polyvalent antibody as typified by IgM and monovalent antibody. Polyvalent antibody according to the present invention includes polyvalent antibody in which all the antigen binding sites are the same and polyvalent antibody in which some or all of the antigen binding sites are different. Antibody according to the present invention is not limited to the full length antibody molecule, but includes low molecular weight antibody and modifications thereof, insofar as these can bind to the HB-EGF protein.

Low molecular weight antibody encompasses antibody fragments generated by the deletion of a portion of the whole antibody (for example, whole IgG). A partial deletion of the antibody molecule is permissible as long as the ability to bind to the HB-EGF antigen is present. The antibody fragment used in the present invention preferably comprises either the heavy chain variable region (VH) or the light chain variable region (VL) or both. The amino acid sequence of the VH or VL can comprise substitutions, deletions, additions, and/or insertions. Moreover, a portion of either the VH or VL or of both can also be deleted, insofar as the ability to bind the HB-EGF antigen remains present. The variable region may also be chimerized or humanized. Specific examples of antibody fragments are Fab, Fab', F(ab')2, and Fv. Specific examples of low molecular weight antibodies are Fab, Fab', F(ab')2, Fv, scFv (single chain Fv), diabody, and sc(Fv)2 (single chain (Fv)2). Multimers of these antibodies (e.g., dimers, trimers, tetramers, polymers) are also encompassed by the low molecular weight antibodies of the present invention.

The antibody fragments can be obtained by the enzymatic treatment of an antibody to produce antibody fragments. For example, papain, pepsin, plasmin, and so forth, are known as enzymes that produce antibody fragments. Or, a gene encoding such an antibody fragment can be constructed and inserted into an expression vector followed by expression by a suitable host cell (refer, for example, to Co, M. S. et al., *J. Immunol.* (1994) 152, 2968-2976; Better, M. & Horwitz, A. H. *Methods in Enzymology* (1989) 178, 476-496; Plueckthun, A. & Skerra, A. *Methods in Enzymology* (1989) 178, 476-496; Lamoyi, E. *Methods in Enzymology* (1989) 121, 652-663; Rousseaux, J. et al., *Methods in Enzymology* (1989) 121, 663-669; and Bird, R. E. et al., *TIBTECH* (1991) 9, 132-137).

A digestive enzyme cleaves specific antibody fragment sites to yield antibody fragments with specific structures as described below. Any portion of the antibody can be deleted when genetic engineering techniques are applied to these enzymatically generated antibody fragments.

papain digestion: F(ab)2 or Fab
pepsin digestion: F(ab')2 or Fab'
plasmin digestion: Facb Diabody designates a bivalent antibody fragment that is constructed by gene fusion (Holliger, P. et al., *Proc. Natl. Acad. Sci. USA* 90, 6444-6448 (1993), EP 404,097, WO 93/11161, and so forth). A diabody is a dimer built up from two polypeptide chains. In general, each of the polypeptide chains constituting a diabody is a VL and a VH ligated by a linker into one and the same chain. The linker for a diabody is generally sufficiently short that the VL and VH are unable to bind to one another. In specific terms, for example, about five amino acid residues make up the linker. Due to this, the VL and VH coded on the same polypeptide chain are unable to form a single chain variable region fragment and form a dimer with a separate single chain variable region fragment. Thus a diabody has two antigen binding sites.

scFv is obtained by ligating the H chain V region of an antibody to the L chain V region. The H chain V region and L chain V region in scFv are ligated to each other by a linker and preferably a peptide linker (Huston, J. S. et al., *Proc. Natl. Acad. Sci. USA* 85, 5879-5883 (1988)). The H chain V region and L chain V region in the scFv may originate from any antibody described herein. There are no particular limitations on the peptide linker that links the V regions. For example, any single peptide chain having from about 3 to 25 residues can be used as the linker.

The V regions can be linked, for example, using the PCR techniques described in the preceding. In order to link the V regions by PCR, DNA coding for all or a desired portion of the amino acid sequence from the DNA sequence coding for the H chain or H chain V region of the antibody and DNA coding for all or a desired portion of the amino acid sequence from the DNA sequence coding for the L chain or L chain V region of the antibody are first used as templates.

The DNA encoding the H chain V region and the DNA encoding the L chain V region are each amplified by PCR using pairs of primers that have sequences that correspond to the sequences at the two ends of the DNA to be amplified. DNA coding for the peptide linker region is then prepared. The peptide linker-encoding DNA can also be synthesized using PCR. A base sequence that can join with each of the separately synthesized V region amplification products is added in advance to the 5' side of the primers used. A PCR reaction is then run using assembly PCR primers and each of the DNAs for [H chain V region DNA]-[peptide linker DNA]-[L chain V region DNA]. The assembly PCR primers are a combination of a primer that anneals to the 5' side of the [H chain V region DNA] and a primer that anneals to the 3' side of the [L chain V region DNA]. That is, the assembly PCR primers form a primer set that can amplify DNA that encodes the full length sequence of the scFv that is to be synthesized. On the other hand, base sequences that can join with each V region DNA are added to the [peptide linker DNA]. As a result, these DNAs are joined and, in addition, the full length of the scFv is finally produced as an amplification product by the assembly PCR primers. Once the scFv-encoding DNA has been produced, an expression vector containing the DNA as well as recombinant cells transformed by the expression vector can be obtained by the usual methods. In addition, the recombinant cells thus obtained can be cultured and scFv can be obtained through expression of the scFv-encoding DNA.

sc(Fv)2 is a low molecular weight antibody in which two VHs and two VLs are ligated by, for example, a linker, into a single chain (Hudson et al., *J. Immunol. Methods,* 231, 177-189 (1999)). sc(Fv)2 can be prepared, for example, by joining scFv's with a linker.

This is preferably an antibody that characteristically has the two VHs and the two VLs lined up in the sequence, considered from the N-terminal side of the single chain polypeptide, VH, VL, VH, VL ([VH]linker-[VL]linker-[VH]linker-[VL]).

The sequence of the two VHs and the two VLs is not particularly limited to the arrangement cited above and they may be aligned in any sequence. The following sequences can be provided as examples.

[VL] linker-[VH] linker-[VH] linker-[VL]
[VH] linker-[VL] linker-[VL] linker-[VH]
[VH] linker-[VH] linker-[VL] linker-[VL]
[VL] linker-[VL] linker-[VH] linker-[VH]
[VL]linker-[VH]linker-[VL]linker-[VH]

The linker connecting the variable regions of the antibody can be, for example, any peptide linker that can be inserted by genetic engineering or a synthetic compound linker, for example, as disclosed in *Protein Engineering,* 9(3), 299-305 (1996). Peptide linkers are preferred in the present invention. The length of the peptide linker is not particularly limited and can be selected as appropriate by those skilled in the art in view of the intended application. In general, from 1 to 100 amino acid residues, preferably from 3 to 50 amino acid residues, more preferably from 5 to 30 amino acid residues, and particularly preferably from 12 to 18 amino acid residues (for example, 15 amino acid residues) are in the peptide linker.

The amino acid sequence of the peptide linker can be any sequence that does not interfere with the binding action of the scFv.

Alternatively, the V regions can also be joined using a synthetic chemical linker (chemical crosslinking agent). Those crosslinking agents typically used to crosslink, for example, peptide compounds, can be used in the present invention. The following, for example, can be used: N-hydroxysuccinimide (NHS), disuccinimidyl suberate (DSS), bis(sulfosuccinimidyl) suberate (BS3), dithiobis(succinimidylpropionate) (DSP), dithiobis(sulfosuccinimidylpropionate) (DTSSP), ethylene glycol bis(succinimidylsuccinate) (EGS), ethylene glycol bis(sulfosuccinimidylsuccinate)

(sulfo-EGS), disuccinimidyl tartrate (DST), disulfosuccinimidyl tartrate (sulfo-DST), bis[2-(succinimidooxycarbonyloxy)ethyl]sulfone (BSOCOES), bis[2-(sulfosuccinimidooxycarbonyloxy)ethyl]sulfone (sulfo-BSOCOES), and so forth.

Three linkers are ordinarily required when ligating four antibody variable regions. Linkers in plurality may be the same as each other or different linkers may be used. Diabody and sc(Fv)2 are preferred low molecular weight antibodies for the present invention. To obtain such low molecular weight antibodies, an antibody may be treated with an enzyme (for example, papain, pepsin, and so forth) to produce antibody fragments, or DNA encoding these antibody fragments may be constructed and inserted into an expression vector followed by expression in a suitable host cell (refer, for example, to Co, M. S. et al., *J. Immunol.* (1994) 152, 2968-2976; Better, M. and Horwitz, A. H. *Methods Enzymol.* (1989) 178, 476-496; Plueckthun, A. and Skerra, A. *Methods Enzymol.* (1989) 178, 497-515; Lamoyi, E. *Methods Enzymol.* (1986) 121, 652-663; Rousseaux, J. et al., *Methods Enzymol.* (1986) 121, 663-669; and Bird, R. E. and Walker, B. W. *Trends Biotechnol.* (1991) 9, 132-137).

In addition, the antibody of the present invention can also be used in the form of a modified antibody to which various molecules, for example, polyethylene glycol (PEG) and so forth, are attached. These modified antibodies can be obtained by chemical modification on the antibody according to the present invention. Antibody modification methods have already been established in the art.

The antibody of the present invention may also be a bispecific antibody. A bispecific antibody is an antibody that has, within the same antibody molecule, variable regions that recognize different epitopes, wherein these epitopes may be present in different molecules or may be present in a single molecule. Thus, in the context of the present invention, a bispecific antibody can have antigen binding sites that recognize different epitopes on the HB-EGF molecule. With such a bispecific antibody, two antibody molecules can bind to one HB-EGF molecule. Therefore a stronger cytotoxicity can be expected. These antibodies are also encompassed by the "antibody" according to the present invention.

The present invention also encompasses bispecific antibody that recognizes an antigen other than HB-EGF. For example, the present invention encompasses bispecific antibody that recognizes an antigen different from HB-EGF, wherein the antigen is specifically expressed on the cell surface of cancer cells that are likewise targets for HB-EGF.

Methods of producing bispecific antibodies are known. For example, a bispecific antibody can be produced by joining two antibodies that recognize different antigens. Each of the joined antibodies may be a half-molecule that has an H chain and an L chain or may be a quarter-molecule that has only an H chain. Or, a fused cell that produces bispecific antibody can also be produced by fusing hybridomas that produce different monoclonal antibodies. Bispecific antibodies can additionally be produced by genetic engineering techniques.

The antibody of the present invention may also be an antibody having engineered sugar chains. It is known that antibody cytotoxicity can be enhanced by engineering the sugar chains on an antibody.

The following are examples of antibodies that have engineered sugar chains: glycosylation-engineered antibodies (e.g., WO 99/54342), antibodies in which the fucose present in the sugar chain has been deleted (e.g., WO 00/61739, WO 02/3140, WO 2006/067847, WO 2006/067913), and antibodies bearing a sugar chain that has bisecting GlcNAc (e.g., WO 02/79255).

Fucose-negative antibody is an example of a preferred sugar chain-engineered antibody of the present invention. The sugar chain linked to an antibody can be an N-glycoside linked sugar chain, which is linked to the side-chain N atom of an asparagine in the antibody molecule, or can be an O-glycoside linked sugar chain, which is linked to the side-chain hydroxyl group of a serine or threonine in the antibody molecule; however, in the present invention, the presence/absence of fucose is an issue involving N-glycoside linked sugar chains.

In the context of the present invention, a fucose-negative antibody indicates that the fucose has been deleted in at least 20%, preferably at least 50%, more preferably at least 70%, and even more preferably at least 90% of the N-glycoside linked sugar chains, based on the N-glycoside linked sugar chains on the antibodies in the particular composition.

Fucose-negative antibody can be prepared by methods known to those skilled in the art; for example, it can be produced by expressing the antibody protein in a host cell that has little or no ability to add α-1,6 core fucose. The host cell that has little or no ability to add fucose may include, but not limited to, YB2/3HL.P2.G11.16Ag.20 rat myeloma cells (abbreviated as YB2/0 cells, preserved as ATCC CRL 1662), FTVIII knock out CHO cells (WO 02/31140), Lec13 cells (WO 03/035835), and fucose transporter-negative cells (e.g., WO 2006/067847, WO 2006/067913).

Sugar chain may be analyzed by methods known to those skilled in the art. For example, the sugar chains can be released from an antibody by the action of, for example, N-Glycosidase F (Roche) on the antibody. Then the sample is desalted by solid-phase extraction using a cellulose cartridge (Shimizu Y. et al., *Carbohydrate Research* 332 (2001), 381-388) followed by concentration to dryness and fluorescent labeling with 2-aminopyridine (Kondo A. et al., *Agricultural and Biological Chemistry* 54:8 (1990), 2169-2170). After the reagent has been removed from the obtained PA-labeled sugar chain by solid-phase extraction using a cellulose cartridge, the purified PA-labeled sugar chain is obtained by concentrating on centrifuge, and measured by reverse-phase HPLC analysis using an ODS column. In addition, after the PA-labeled sugar chain is prepared, two-dimensional mapping can also be carried out, in which reverse-phase HPLC analysis with an ODS column is combined with normal-phase HPLC analysis with an amine column.

The antibodies described in [1] to [13] below are examples of antibodies that can be used in the present invention.

[1] antibody comprising a heavy chain variable region having the amino acid sequence of SEQ ID NO: 14 as CDR1, the amino acid sequence of SEQ ID NO: 16 as CDR2, and the amino acid sequence of SEQ ID NO: 18 as CDR3;

[2] antibody comprising a light chain variable region having the amino acid sequence of SEQ ID NO: 20 as CDR1, the amino acid sequence of SEQ ID NO: 22 as CDR2, and the amino acid sequence of SEQ ID NO: 24 as CDR3;

[3] antibody comprising the heavy chain according to [1] and the light chain according to [2];

[4] antibody comprising a heavy chain variable region having the amino acid sequence of SEQ ID NO: 26 as CDR1, the amino acid sequence of SEQ ID NO: 28 as CDR2, and the amino acid sequence of SEQ ID NO: 30 as CDR3;

[5] antibody comprising a light chain variable region having the amino acid sequence of SEQ ID NO: 32 as CDR1, the amino acid sequence of SEQ ID NO: 34 as CDR2, and the amino acid sequence of SEQ ID NO: 36 as CDR3;

[6] antibody comprising the heavy chain according to [4] and the light chain according to [5];

[7] antibody comprising a heavy chain variable region having the amino acid sequence of SEQ ID NO: 76 as CDR1, the amino acid sequence of SEQ ID NO: 77 as CDR2, and the amino acid sequence of SEQ ID NO: 78 as CDR3; (HE-39 Heavy chain)

[8] antibody comprising a light chain variable region having the amino acid sequence of SEQ ID NO: 79 as CDR1, the amino acid sequence of SEQ ID NO: 80 as CDR2, and the amino acid sequence of SEQ ID NO: 81 as CDR3; (HE-39 L chain-1)

[9] antibody comprising a light chain variable region having the amino acid sequence of SEQ ID NO: 82 as CDR1, the amino acid sequence of SEQ ID NO: 83 as CDR2, and the amino acid sequence of SEQ ID NO: 84 as CDR3; (HE-39 L chain-2)

[10] antibody comprising the heavy chain according to [7] and the light chain according to [8];

[11] antibody comprising the heavy chain according to [7] and the light chain according to [9];

[12] antibody having the activity equivalent to that of the antibody described in any of [1] to [11];

[13] antibody that binds an epitope that is the same as the epitope bound by an antibody described in any of [1] to [12].

With reference to the antibody according to [12] above, "equivalent activity" means that the binding activity for HB-EGF is at least 70%, preferably at least 80%, and more preferably at least 90% of the binding activity of the antibody described in any of [1] to [11], or that, in the case of conjugation with a cytotoxic substance, the antitumor activity is at least 70%, preferably at least 80%, and more preferably at least 90% of the antitumor activity of the antibody described in any of [1] to [11].

The introduction of mutation into a polypeptide is a method well known to those skilled in the art for producing a polypeptide that is functionally equivalent to a particular polypeptide. For example, as known to those skilled in the art, antibody that exhibits the activity equivalent to that of an antibody of the present invention can be produced by introducing suitable mutations into the antibody of the present invention using site-specific mutagenesis (Hashimoto-Gotoh, T. et al. (1995) *Gene* 152, 271-275; Zoller, M. J. and Smith, M. (1983) *Methods Enzymol.* 100, 468-500; Kramer, W. et al. (1984) *Nucleic Acids Res.* 12, 9441-9456; Kramer, W. and Fritz, H. J. (1987) *Methods Enzymol.* 154, 350-367; Kunkel, T. A. (1985) *Proc. Natl. Acad. Sci. USA* 82, 488-492; and Kunkel (1988) *Methods Enzymol.* 85, 2763-2766). Amino acid mutations may also be produced by natural mutation. The antibody of the present invention also encompasses antibody that has an amino acid sequence generated by one or more amino acid mutations in the amino acid sequence of an antibody of the present invention and that exhibits the activity equivalent to that of the antibody of the present invention. With regard to the number of amino acids that have been mutated in such a mutant, generally no more than 50 amino acids, preferably no more than 30 amino acids, and more preferably no more than 10 amino acids (for example, no more than 5 amino acids) can be considered.

Preferably, the amino acid residue is mutated to another amino acid residue that conserves the characteristics of the amino acid side chain. For example, the following classification has been established based on the characteristics of the amino acid side chain. hydrophobic amino acids (A, I, L, M, F, P, W, Y, V) hydrophilic amino acids (R, D, N, C, E, Q, G, H, K, S, T) amino acids having an aliphatic side chain (G, A, V, L, I, P) amino acids having a hydroxyl-containing side chain (S, T, Y) amino acids having a sulfur-containing side chain (C, M) amino acids having a carboxyl- or amide-containing side chain (D, N, E, Q) amino acids having a base-containing side chain (R, K, H) amino acids having an aromatic-containing side chain (H, F, Y, W) (The single letter designation for the amino acids is given in the parentheses.)

In the case of a polypeptide having a modified amino sequence generated by deleting and/or adding one or a plurality of amino acid residues from and/or to a particular amino acid sequence and/or by substituting one or a plurality of amino acid residues in the particular amino sequence with another amino acid, it is already known that such a polypeptide can maintain its biological activity (Mark, D. F. et al., *Proc. Natl. Acad. Sci. USA* (1984) 81, 5662-5666; Zoller, M. J. and Smith, M., *Nucleic Acids Research* (1982) 10, 6487-6500; Wang, A. et al., *Science* 224, 1431-1433; Dalbadie-McFarland, G. et al., *Proc. Natl. Acad. Sci. USA* (1982) 79, 6409-6413). That is, in general, when, in the amino acid sequence of a particular polypeptide, the amino acids in a particular classification are substituted by other amino acids in that classification, there is a high probability that the activity of the particular polypeptide will be retained. Substitutions between amino acids in the same classification in the amino acid classification provided above are designated in the present invention as conservative substitutions.

In [13], supra, the present invention also provides antibody that binds to an epitope that is the same as the epitope bound by anti-HB-EGF antibody disclosed by the present invention. Such an antibody can be obtained, for example, by the following method.

Whether a test antibody and a particular antibody have a common epitope can be determined by competition by the two for the same epitope. Competition between antibodies can be detected, for example, by a reciprocal blocking assay. For example, a competitive ELISA assay is a preferred reciprocal blocking assay. In specific terms, in a reciprocal blocking assay, HB-EGF protein is coated on the wells of a microtiter plate; pre-incubated in the presence or absence of the candidate competitive antibody; then the anti-HB-EGF antibody of the present invention is added. The amount of anti-HB-EGF antibody of the present invention that has become bound to the HB-EGF protein in the well is indirectly correlated with the binding activity of the candidate competitive antibody (test antibody) competing for binding to the same epitope. That is, the higher the affinity of the test antibody for the same epitope, the less anti-HB-EGF antibody of the present invention that binds to the HB-EGF protein-coated well and the greater the amount of binding by the test antibody to the HB-EGF protein-coated well.

The amount of well-bound antibody can be conveniently measured by labeling the antibody in advance. For example, biotin-labeled antibody can be measured using an avidin-peroxidase conjugate and a suitable substrate. A reciprocal blocking assay based on an enzyme label such as peroxidase is in particular known as a competitive ELISA assay. The antibody can be labeled with some other label that can be detected or measured. In specific terms, radioactive labels and fluorescent labels are also known.

In addition, when the test antibody has a constant region originating from a species different from that for the anti-HB-EGF antibody of the present invention, the amount of well-bound antibody can also be measured using a labeled secondary antibody that recognizes the constant region of the antibody. Or, even when the antibody originates in the same species but the classes are different, the amount of well-bound antibody can be measured using a secondary antibody that discriminates among the individual classes.

When—in comparison to the binding activity obtained in the control test that is carried out in the absence of the candidate competitive antibody—the candidate antibody can block binding of at least 20%, preferably at least 20 to 50%, and even more preferably at least 50% of the anti-HB-EGF antibody, such a candidate competitive antibody is then an antibody that binds to substantially the same epitope as the anti-HB-EGF antibody of the present invention or that competes for binding to the same epitope.

For example, antibody that recognizes the region in the HB-EGF protein with the sequence APSCICHPGYHGER-CHGLSL is a preferred example of antibody that binds to the same epitope as the epitope to which the antibody in [10] or [11] binds.

Binding Activity by Antibody

Known procedures can be used to measure the antigen binding activity of an antibody (Antibodies: A Laboratory Manual. Ed Harlow, David Lane, Cold Spring Harbor Laboratory, 1988). For example, an enzyme-linked immunosorbent assay (ELISA), enzyme immunoassay (EIA), radioimmunoassay (RIA), or immunofluorescence procedure can be used. The method described on pages 359 to 420 of Antibodies: A Laboratory Manual is an example of a procedure for measuring the binding activity by an antibody for antigen expressed in a cell.

In addition, procedures that in particular employ a flow cytometer can be suitably used to measure binding between antigen expressed on the surface of cells suspended in, for example, buffer, and antibody against the antigen. Examples of usable flow cytometers are as follows: FACSCanto™ II, FACSAria™, FACSArray™, FACSVantage™ SE, and FACSCalibur™ (the preceding instruments are from BD Biosciences), and EPICS ALTRA HyPerSort, Cytomics FC 500, EPICS XL-MCL ADC EPICS XL ADC, and Cell Lab Quanta/Cell Lab Quanta SC (the preceding instruments are from Beckman Coulter).

In one example of a convenient method for measuring the binding activity of a test HB-EGF antibody for an antigen, the test antibody is reacted with a cell that expresses HB-EGF, and stained with FITC-labeled secondary antibody that recognizes the test antibody. The fluorescent intensity is measured with FACSCalibur (Becton, Dickinson and Company) and analyzed with CELL QUEST software (Becton, Dickinson and Company).

Proliferation Inhibiting Activity

The following methods are conveniently used to evaluate or measure the cell proliferation inhibiting effect due to anti-HB-EGF antibody. In a method that can be used to evaluate or measure the cell proliferation inhibiting activity in vitro, the uptake by live cells of [$^3$H]-labeled thymidine added to the medium is measured as an index of the DNA replication ability. Methods that are more convenient include the MTT method and dye exclusion methods in which the ability of cells to exclude a dye (e.g., trypan blue) is measured using a microscope. The MTT method utilizes the fact that live cells have the ability to convert the tetrazolium salt MTT (3-(4,5-dimethylthiazol-2-yl)-2,5-diphenyl tetrazolium bromide) into a blue formazan product. More specifically, the ligand and test antibody are added to the culture fluid of the test cell and, after a specified time has passed, an MTT solution is added to the culture fluid and MTT is incorporated into the cells by standing for a specified period of time. As a result, MTT, which is a yellow compound, is converted into a blue compound by succinate dehydrogenase in the mitochondria within the cells. The blue product is dissolved to provide coloration, and measurement of its absorbance provides an index to the viable cell count. In addition to MTT, reagents such as MTS, XTT, WST-1, WST-8, and so forth are also commercially available (Nacalai Tesque, Inc.) and can be suitably used. In the activity measurement, a control antibody is used in the same way as the anti-HB-EGF antibody; the control antibody is a binding antibody that has the same isotype as the anti-HB-EGF antibody while not having the aforementioned cell proliferation inhibiting activity. The antibody has the cell proliferation inhibiting activity when the anti-HB-EGF antibody exhibits a stronger cell proliferation inhibiting activity than the control antibody.

Tumor-supporting mouse models may also be used as a method for evaluating or measuring the cell proliferation inhibiting activity in vivo. For example, cancer cells whose growth is promoted by HB-EGF may be subcutaneously or intracutaneously grafted into a nonhuman test animal, after which the test antibody may be administered intravenously or intraabdominally every day or on a multiday interval beginning on the day of grafting or on the next day. The cell proliferation inhibiting activity can be evaluated by measuring tumor size with elapsed time. Just as with the in vitro evaluation, a control antibody having the same isotype is administered, and the antibody has a cell proliferating inhibiting activity when the tumor size in the group receiving the anti-HB-EGF antibody is significantly smaller than the tumor size in the group receiving the control antibody. The nude (nu/nu) mouse is suitably employed when the mouse is used as the nonhuman test animal; the nude (nu/nu) mouse lacks T-lymphocyte function due to the genetic loss of the thymus gland. The use of this type of mouse makes it possible to exclude a contribution by T-lymphocytes in the test animal in the evaluation or measurement of the cell proliferation inhibiting activity due to the administered antibody.

The method of inhibiting cell proliferation

The present invention provides a method of inhibiting the proliferation of HB-EGF-expressing cells by bringing such cells into contact with the antibody of the present invention. The antibody of the present invention, which is present in the cell proliferation inhibitor of the present invention, is an HB-EGF protein-binding antibody as has been described above. There are no particular limitations on the cells that may be brought into contact with the anti-HB-EGF antibody other than that these cells express HB-EGF, but disease-related cells are preferred. Cancer cells are a preferred example of the disease-related cells. The cancer is preferably pancreatic cancer, liver cancer, esophageal cancer, melanoma, colorectal cancer, gastric cancer, ovarian cancer, uterine cervical cancer, breast cancer, bladder cancer, a brain tumor, or a hematological cancer. The hematological cancers include, for example, myelomas, lymphomas, and leukemias.

The Delivery Method Using anti-HB-EGF Antibody

The present invention relates to a method of delivering a cytotoxic substance into a cell using anti-HB-EGF antibody. The antibody used in this method is the cytotoxic activity-conjugated anti-HB-EGF antibody that has been described above. Delivery of the cytotoxic substance can be achieved by bringing HB-EGF-expressing cells into contact with the cytotoxic substance-conjugated anti-HB-EGF antibody. There are no particular limitations in the present invention on the cells to which the cytotoxic substance is delivered, but disease-related cells are preferred. Cancer cells are an example of the disease-related cells. The cancer is preferably pancreatic cancer, liver cancer, esophageal cancer, melanoma, colorectal cancer, gastric cancer, ovarian cancer, uterine cervical cancer, breast cancer, bladder cancer, a brain tumor, or a hematological cancer. The hematological cancers include, for example, myelomas, lymphomas, and leukemias.

Contact in the present invention may be carried out in vitro or in vivo. With regard to the state in which the antibody is added here, for example, a solid obtained by freeze-drying or a solution may suitably be used. In those instances where the antibody is added in the form of the aqueous solution, this may be an aqueous solution that contains only the pure antibody or may be a solution that contains, for example, surfactant, excipient, colorant, flavorant, preservative, stabilizer, buffer, suspending agent, tonicity agent, binder, disintegrant, lubricant, fluidity promoter, taste-masking agent, and so forth. While there are no particular limitations on the concentration of addition, suitable final concentrations in the culture fluid are preferably 1 pg/mL to 1 g/mL, more preferably 1 ng/mL to 1 mg/mL, and even more preferably 1 µg/mL to 1 mg/mL.

in vivo "contact" may also be carried out in the present invention by administration to a non-human animal into which HB-EGF-expressing cells have been implanted, transplanted, or grafted, or by administration to an animal that bears HB-EGF-expressing cancer cells. The mode of administration may be oral administration or parenteral administration. Parenteral administration is particularly preferred, and the corresponding routes of administration may include injection, transnasal administration, transpulmonary administration, transdermal administration, and so forth. With regard to examples of administration by injection, the pharmaceutical composition of the present invention, as a cell proliferation inhibitor or anti-cancer agent, can be administered systemically or locally by, for example, intravenous injection, intramuscular injection, intraperitoneal injection, or subcutaneous injection. The appropriate mode of administration can be selected as a function of the age and symptomatology of the animal subject. In those instances where an aqueous solution is administered, this solution may be an aqueous solution that contains only the pure antibody or may be a solution that contains, for example, surfactant, excipient, colorant, flavorant, preservative, stabilizer, buffer, suspending agent, tonicity agent, binder, disintegrant, lubricant, fluidity promoter, taste-masking agent, and so forth. The dosage, for example, may be selected from the range of 0.0001 mg to 1000 mg per 1 kg body weight per administration. Alternatively, the dosage may be selected from the range of 0.001 to 100000 mg/body per patient. However, the dosage of the antibody of the present invention is not limited to the preceding dosages.

The Pharmaceutical Composition

In another aspect, a characteristic feature of the present invention is a pharmaceutical composition that comprises an antibody that binds to HB-EGF protein. An additional characteristic feature of the present invention is a cell proliferation inhibitor, and particularly an anti-cancer agent, that comprises an antibody that binds to HB-EGF protein. The cell proliferation inhibitor of the present invention and the anti-cancer agent of the present invention are preferably administered to a subject suffering from cancer or to a subject at risk for cancer.

In the present invention, the cell proliferation inhibitor comprising HB-EGF protein-binding antibody also subsumes a method of inhibiting cell proliferation comprising a step of administering HB-EGF protein-binding antibody to a subject as well as the use of HB-EGF protein-binding antibody for the production of a cell proliferation inhibitor.

Moreover, in the present invention, the anti-cancer agent comprising HB-EGF protein-binding antibody subsumes a method of preventing or treating cancer comprising a step of administering HB-EGF protein-binding antibody to a subject as well as the use of HB-EGF protein-binding antibody for the production of an anti-cancer agent.

There are no particular limitations on the antibody present in the pharmaceutical composition of the present invention (for example, a cell proliferation inhibitor or an anti-cancer agent; this also applies below) other than that this antibody has the ability to bind to HB-EGF protein, and any of the antibodies provided herein as examples may also be used.

The mode of administration of the pharmaceutical composition of the present invention may be oral administration or parenteral administration. Parenteral administration is particularly preferred, and the corresponding routes of administration may include injection, transnasal administration, transpulmonary administration, transdermal administration, and so forth. With regard to examples of administration by injection, the pharmaceutical composition of the present invention can be administered systemically or locally by, for example, intravenous injection, intramuscular injection, intraperitoneal injection, or subcutaneous injection. The appropriate mode of administration can be selected as a function of the age and symptomatology of the patient. The dosage, for example, may be selected from the range of 0.0001 mg to 1000 mg per 1 kg body weight per administration. Alternatively, the dosage may be selected from the range of 0.001 to 100000 mg/body per patient. However, the pharmaceutical composition of the present invention is not limited to the preceding dosages.

The pharmaceutical composition of the present invention can be formulated according to the usual methods (for example, Remington's Pharmaceutical Science, latest edition, Mack Publishing Company, Easton, USA) and may comprise a pharmaceutically acceptable vehicle and pharmaceutically acceptable additives. Examples are surfactants, excipients, colorants, flavorants, preservatives, stabilizers, buffers, suspending agents, tonicity agents, binders, disintegrants, lubricants, fluidity promoters, taste-masking agents, and so forth, but there is no limitation to the preceding and other generally used vehicles can be employed as appropriate. Specific examples are light silicic anhydride, lactic acid, crystalline cellulose, mannitol, starch, carmellose calcium, carmellose sodium, hydroxypropyl cellulose, hydroxypropylmethyl cellulose, polyvinyl acetal diethylamino acetate, polyvinylpyrrolidone, gelatin, medium-chain fatty acid triglycerides, polyoxyethylene hardened castor oil 60, sucrose, carboxymethyl cellulose, corn starch, inorganic salts, and so forth.

The Method of Producing a Pharmaceutical Product

The present invention additionally provides a method of producing a pharmaceutical product and particularly an anti-cancer agent, comprising the steps of:

(a) providing anti-HB-EGF antibody;

(b) determining whether the antibody of (a) has an internalizing activity;

(c) selecting antibody that has an internalizing activity; and (d) attaching a cytotoxic substance to the antibody selected in (c).

The presence/absence of an internalizing activity can be determined by the methods described above. In addition, the anti-HB-EGF antibody and the cytotoxic substance can be the anti-HB-EGF antibody and the cytotoxic substance already described above.

Cancer Diagnosis

Based on the fact that HB-EGF expression increases in a broad range of cancers, such as pancreatic cancer, liver cancer, esophageal cancer, melanoma, colorectal cancer, gastric cancer, ovarian cancer, uterine cervical cancer, breast cancer, bladder cancer, brain tumors, and hematological tumors, the present invention provides in another of its aspects a method of diagnosing a disease, and particularly a method of diagnosing cancer, using anti-HB-EGF antibody.

The diagnostic method of the present invention can be carried out through detection of the anti-HB-EGF antibody that has become incorporated within a cell. The anti-HB-EGF antibody used in the present invention preferably has an internalizing activity and is preferably labeled with a labeling substance.

Accordingly, a preferred embodiment of the diagnostic method of the present invention is a diagnostic method that employs anti-HB-EGF antibody that has been labeled with a labeling substance and that has an internalizing activity. The abovementioned anti-HB-EGF antibody can be used for an anti-HB-EGF antibody to be bound to the labeling substance.

The labeling substance attached to the anti-HB-EGF antibody is not particularly limited, and those labeling substances known to those skilled in the art can be used, for example, fluorescent dyes, enzymes, co-enzymes, chemiluminescent substances, radioactive substances, and so forth. Specific examples are radioisotopes (e.g., 32P, 14C, 125I, 3H, 131I, and so forth), fluorescein, rhodamine, dansyl chloride, umbelliferone, luciferase, peroxidase, alkali phosphatase, β-galactosidase, β-glucosidase, horseradish peroxidase, glucoamylase, lysozyme, saccharide oxidase, microperoxidase, biotin, and so forth. When biotin is used as the labeling substance, the addition of the biotin-labeled antibody is preferably followed by the addition of avidin attached to an enzyme such as alkali phosphatase. Known methods can be used to attach the labeling substance to the anti-HB-EGF antibody, for example, the glutaraldehyde method, maleimide method, pyridyl disulfide method, periodic acid method, and so forth. The labeling substance may be attached to the antibody by procedures known to those skilled in the art.

There are no particular limitations on the type of cancer when cancer is the disease being diagnosed by the method of the present invention, but the cancer is preferably pancreatic cancer, liver cancer, esophageal cancer, melanoma, colorectal cancer, gastric cancer, ovarian cancer, uterine cervical cancer, breast cancer, bladder cancer, a brain tumor, or a hematological cancer. The hematological cancers include, for example, myelomas, lymphomas, and leukemias.

Diagnosis in the present invention may be carried out in vivo or in vitro.

The in vitro diagnosis may be carried out, for example, according to a method comprising the steps of:
(a) providing a sample collected from a subject;
(b) bringing the sample from (a) into contact with anti-HB-EGF antibody to which a labeling substance is attached; and
(c) detecting the antibody that has become incorporated within cells.

There are no particular limitations on the sample that is collected, and may include cells collected from the subject and tissue collected from the subject. The sample used in the present invention also encompasses secondary samples that have been obtained from the test sample, for example, a cell culture fluid or a specimen prepared by fixing tissue or cells collected from the body of a living organism.

The in vivo diagnosis may be carried out, for example, according to a method comprising the steps of:
(a) administering labeled anti-HB-EGF antibody to a subject; and
(b) detecting the antibody that has become incorporated within cancer cells.

The dosage of the anti-HB-EGF antibody can be set as appropriate by those skilled in the art based on, for example, the type of labeling substance, the disease to be diagnosed, and so forth. The labeled anti-HB-EGF antibody may be formulated using the methods already described above.

The present invention additionally provides a method of producing a diagnostic reagent, and particularly a diagnostic reagent for cancer, comprising the steps of:
(a) providing anti-HB-EGF antibody;
(b) determining whether the antibody of (a) has an internalizing activity;
(c) selecting antibody that has an internalizing activity; and
(d) binding a labeling substance to the antibody selected in (c).

The presence/absence of the internalizing activity can be determined by the methods already described above. In addition, the anti-HB-EGF antibody and the labeling substance can be the anti-HB-EGF antibody and the labeling substance already described above.

The contents of all the patents and reference literature explicitly cited in the specification are herein incorporated by reference in their entirety. The contents of the specification and drawings in Japanese Patent Applications 2006-286824 and 2007-107207, which applications form the basis for the priority cited by the present application, are also herein incorporated by reference in their entirety.

EXAMPLES

The present invention is described in greater detail by the examples provided below, but the present invention is not limited by these examples.

Immunization
1-1. Immunogen Production
1-1-1. Construction of an HB-EGF Expression Vector In order to construct an HB-EGF expression vector, an HB-EGF gene was first cloned as described below. Using human heart cDNA (human Marathon Ready cDNA, Clontech Laboratories, Inc.) as template, RT-PCT was carried out using Pyrobest Taq polymerase (Takara Bio Inc.) and the full-length HG-EGF gene was cloned.

```
                                        (SEQ ID NO: 51)
EGF-1: ATGAAGCTGCTGCCGTCGGTG (SEQ ID NO: 52)
EGF-2: TCAGTGGGAATTAGTCATGCCC
(94° C./30 s, 65° C./30 s, 72° C./60 s: 35 cycles)
```

Using the obtained PCR product as template, PCR was carried out for the second time under the conditions given below and a full-length HB-EGF cDNA fragment was obtained in which SalI and NotI cleavage sequences were added, respectively, at the 5' and 3' terminals.

```
                                        (SEQ ID NO: 53)
EGF-3: TAAGTCGACCACCATGAAGCTGCTGCCGTCGGTG (SEQ ID NO: 54)
EGF-4: TTTGCGGCCGCTCACTTGTCATCGTCGTCCTT
GTAGTCGTGGGAATTAGTCATGCCCAAC
(94° C./30 s, 65° C./30 s, 72° C./60 s: 25 cycles)
```

The fragment was digested with SalI and NotI and was inserted into an expression vector for use with animal cells (pMCN) that had likewise been digested with SalI and NotI, thus constructing an HB-EGF expression vector (pMCN_HB-EGF).

1-1-2. Construction of an HB-EGF_Fc Fusion Protein Expression Vector

A fusion protein (HB-EGF_Fc) between the extracellular domain of HB-EGF and the Fc region of mouse IgG2a was used as the immunogen for acquisition of HB-EGF neutralizing antibody. The structure of the immunizing fusion protein is shown in FIG. 1.

The expression vector for the mouse Fc region/HB-EGF fusion protein was constructed as described below. First, using the HB-EGF expression vector (pMCN_HB-EGF) as template, PCR was carried out under the following conditions using
Pyrobest Tag polymerase (Takara Bio Inc.).

```
EGF-5:
                                          (SEQ ID NO: 55)
AAAGAATTCCACCATGAAGCTGCTGCCGTC

EGF-6:
                                          (SEQ ID NO: 56)
TATCGGTCCGCGAGGTTCGAGGCTCAGCCCATGACACCTC (94° C./30 s, 68° C./30 s, 72° C./30 s:
25 cycles)
```

The obtained PCR product was then digested with EcoRI and CpoI. The resulting DNA fragment was inserted between EcoRI and CpoI in an animal cell expression vector that contained mouse IgG2a_Fc (pMCDN_mIgG2a_Fc) to construct an HB-EGF-Fc expression vector (pMCDN_HB-EGF-Fc).

1-1-3. Creation of an HB-EGF_Fc-Producing Strain

15 µg of the HB-EGF-Fc expression vector pMCDN_HB-EGF-Fc, which had been linearized by digestion with pvuI, was transfected by electroporation at 1.5 kV, 25 µF (Gene Pulser from Bio-Rad Laboratories, Inc.) into DG44 cells ($1\times10^7$ cells/mL, 800 µL) suspended in PBS(-). After dilution to a suitable cell count with a growth medium (CHO-S-SFM II, Invitrogen Corporation) containing penicillin/streptomycin (PS), the cells were seeded to 96-well plates and 500 µg/mL G418 (geneticin, Invitrogen Corporation) was added the next day. After about 2 weeks, wells having a monoclone were selected under a microscope and SDS-PAGE was run using 10 µL of the culture supernatant from each. Cell lines producing HB-EGF-Fc were screened by Western blotting using a PVDF membrane and goat anti-HB-EGF antibody (AF-259-NA, R&D Systems, Inc.) and HRP-anti-goat antibody (ACI3404, BioSource). The highest producing strain was selected and subjected to expansion culture.

1-1-4. Purification of the HB-EGF_Fc Protein

The HB-EGF_Fc protein was purified from the culture supernatant of the obtained HB-EGF_Fc-producing strain using a Hi Trap Protein G HP 1 mL column (Amersham Biosciences #17-0404-01). The culture supernatant was adsorbed at a flow rate of 1 mL/min followed by washing with 20 mL 20 mM phosphate buffer (pH 7.0) and then elution with 3.5 mL 0.1 M glycine-HCl (pH 2.7). The eluate was recovered in 0.5 mL fractions in Eppendorf tubes, each of which already contained 50 µL 1 M Tris-HCl (pH 9.0). The $OD_{280nm}$ was measured. The fractions containing the target protein were combined and PBS(-) was added to bring to a total of 2.5 mL, then the buffer was replaced with PBS(-) using a PD-10 column (Amersham Biosciences #17-0851-01). The purified protein was passed through a 0.22 µm filter (Millipore #SLGV033RS) and was stored at 4° C.

1-2. Immunization

An emulsion of the HB-EGF_Pc protein was prepared with Complete Adjuvant (DIFCO DF263810) for the initial immunization and with Incomplete Adjuvant (DIFCO DC263910) for the second and subsequent immunizations. Three animals [(MRL/lpr, male, age: 4 weeks)(balb/c, female, age: 6 weeks), both purchased from Charles River Japan] were immunized by subcutaneous injection at 50 µg/mouse (1 mL Thermo syringe, 26-gauge needle). The second immunization was given two weeks after the initial immunization, and a total of 4-5 immunizations were given on a one week interval. For the final immunization, the HB-EGF_Fc (50 µg) was suspended in 100 µL PBS and was injected into the tail vein; cell fusion was carried out three days later.

1-3. Hybridoma Production

Cell fusion was carried out as follows. The spleen was aseptically removed from the mouse and a single cell suspension was prepared by grinding in medium 1 (RPMI1640+PS). The suspension was passed through a 70 µm nylon mesh (Falcon) to remove fatty tissue and so forth and the cells were counted. The obtained B cells were mixed with mouse myeloma cells (P3U1 cells) in a cell count ratio of about 2:1; 1 mL 50% PEG (Roche, cat #783 641) was added; and cell fusion was carried out. The fused cells were suspended in medium 2 (RPMI1640+PS, 10% FCS, HAT (Sigma, H0262), 5% BM Condimed H1 (Roche #1088947)), and distributed at 200 µL/well into a suitable number of 96-well plates (10 plates) and cultivated at 37° C. After one week, hybridoma were screened using the culture supernatant and analyzed. The hybridomas originating from two Balb/c mice were designated as the HA series and the HB series, respectively, and the hybridomas originating from one Mrl/lpr mouse were designated as the HC series.

Screening for Anti-HB-EGF Neutralizing Antibody

2-1. Creation of Human HB-EGF-Expressing Cell Lines

2-1-1. Creation of the Strain HB-EGF_DG44

An HB-EGF-expressing DG44 cell line was established as follows. First, 15 µg of the HB-EGF expression vector pMCN_HB-EGF constructed as described in 1-1-1 was digested with pvuI and was transfected into DG44 cells by electroporation using the same procedure as in 1-1-3. Then the G418-resistant strains were picked out and the cells were stained with goat anti-HB-EGF antibody (R&D Systems, Inc.) and FITC-labeled anti-goat IgG antibody. The HB-EGF expressed on the cell surface was analyzed with a FACSCalibur (Becton, Dickinson and Company) and the high-expressing clone was selected.

2-1-2. Creation of the Strain HB-EGF_Ba/F3

A Ba/F3 cell line that expressed HB-EGF on the cell membrane was established as follows. It is known that the HB-EGF expressed on the cell membrane is processed by protease and cleaved into the culture medium. Therefore, an expression vector for proHB-EGF mutated at the protease cleavage site was first constructed.

Using pMCN-HB-EGF as template, separate PCRs were carried out using the following two sets of conditions and Pyrobest Taq polymerase (Takara Bio Inc.).

```
PCR reaction 1
EGF-3:
                                          (SEQ ID NO: 53)
TAAGTCGACCACCATGAAGCTGCTGCCGTCGGTG EGF-7:
                                          (SEQ ID NO: 57)
CGATTTTCCACTGTGCTGCTCAGCCCATGACACCTCTC (94° C./30 s, 68° C./30 s, 72° C./30 s:
20 cycles)
```

-continued

PCR reaction 2
EGF-8:
(SEQ ID NO: 58)
TGGGCTGAGCAGCACAGTGGAAAATCGCTTATATACCTA

EGF-4:
(SEQ ID NO: 54)
TTTGCGGCCGCTCACTTGTCATCGTCGTCCTTGTAGTCGTGGGAAT
TAGTCATGCCCAAC (94° C./30 s, 68° C./30 s, 72° C./30 s:
20 cycles)

The two DNA fragments obtained by PCR reactions 1 and 2 were then mixed; a recombination reaction (94° C./30 s, 72° C./60 s: 5 cycles) was run using Pyrobest Taq polymerase (Takara Bio Inc.); followed by PCR under the following conditions using 1 μL of the preceding reaction solution as template.

EGF-3:
(SEQ ID NO: 53)
TAAGTCGACCACCATGAAGCTGCTGCCGTCGGTG

EGF-4:
(SEQ ID NO: 54)
TTTGCGGCCGCTCACTTGTCATCGTCGTCCTTGTAGTCGTGGGAAT
TAGTCATGCCCAAC (94° C./30 s, 68° C./30 s, 72° C./60 s:
22 cycles)

The obtained PCR product was digested with SalI and NotI followed by insertion into an expression vector for use in animal cells (pMCN) that had likewise been digested with SalI and NotI, in order to construct a proHB-EGF expression vector (pMCN-MHB-EGF).

A Ba/F3 cell line that expressed proHB-EGF was then created as described in the following. 15 μg of the previously constructed proHB-EGF expression vector pMCN-MHB-EGF was cleaved with pvuI and then transfected by electroporation at 0.33 kV, 950 μF (Gene Pulser from Bio-Rad Laboratories, Inc.) into Ba/F3 cells suspended in PBS(–) ($1\times10^7$ cells/mL, 800 μL). These cells were then cultured in 96-well plates on medium (RPMI1640, 10% FCS, PS) containing 1 ng/mL IL-3 and 500 μg/mL G418, and after two weeks the G418-resistant strains were picked out. The cells were stained with goat anti-HB-EGF antibody (R&D Systems, Inc.) and FITC-labeled anti-mouse IgG antibody (Beckman Coulter, PN IM0819) and the clone was selected that presented a high level of expression of cell surface HB-EGF according to FACS (Becton, Dickinson and Company).

2-2. Creation of HB-EGF-Expressing SKOV-3 Cells

A SKOV-3 cell line that expressed HB-EGF was established as described in the following. SKOV-3 (purchased from ATTC), which is an ovarian cancer cell line, was cultured on a growth medium (McCoy's 5A medium, Invitrogen Corporation) that contained 10% FCS and penicillin/streptomycin (P/S).

15 μg of the HB-EGF expression vector pMCN_HB-EGF constructed in 1-1-1 was digested with pvuI. This was followed by transfection by electroporation at 1.5 kV, 25 μF (Gene Pulser from Bio-Rad Laboratories, Inc.) into SKOV-3 cells suspended in PBS(–) ($1\times10^7$ cells/mL, 800 μL). Dilution to a suitable cell count using the growth medium cited above was followed by seeding to 96-well plates. G418 (geneticin, Invitrogen Corporation) was added the next day at 500 μg/mL. After about two weeks the G418-resistant monoclones were selected and screened for HB-EGF-expressing cell lines by Western blotting. The highest producing line was selected and used in subsequent experiments.

2-3. Creation of an EGFR_Ba/F3 Cell Line that Exhibits HB-EGF-Dependent Growth 2-3-1. Construction of pCV-hEGFR/G-CSFR In order to evaluate the activity of antibody of the present invention, a vector was constructed that expressed a chimeric receptor (hEGFR/mG-CSFR) composed of the extracellular region of human EGFR and the intracellular region of mouse G-CSFR. The effect on a cell that expresses the chimeric receptor when HB-EGF binds to such a cell is shown schematically in FIG. 2a.

In order to clone the gene encoding the extracellular region of the human epidermal growth factor receptor (EGFR), PCR was carried out with human liver cDNA (Marathon Ready cDNA, Clontech Laboratories, Inc.) as a template using the primer set specified below. The base sequence (MN_005228) and the amino acid sequence (NP_005219) of human EGFR are shown, respectively, in SEQ ID NO: 59 and SEQ ID NO: 60.

EGFR-1:
ATGCGACCCTCCGGGACGGC          (SEQ ID NO: 61)

EGFR-2:
CAGTGGCGATGGACGGGATCT         (SEQ ID NO: 62)

(94° C./30 s, 65° C./30 s, 72° C./2 min:
35 cycles)

The amplified cDNA (approximately 2 Kb) was excised from the agarose gel and was inserted into the pCR-TOPO vector (Invitrogen Corporation). The base sequence of the fragment inserted into this plasmid was analyzed and confirmed that the obtained EGFR gene had the correct sequence. PCR was then carried out with the plasmid obtained as above as a template using the following primer set.

EGFR-5:
(SEQ ID NO: 63)
TTGCGGCCGCCACCATGCGACCCTCCGGGACGGC

EGFR-6:
(SEQ ID NO: 64)
ACCAGATCTCCAGGAAAATGTTTAAGTCAGATGGATCGGACGGGATC
TTAGGCCCATTCGT (94° C./30 s, 68° C./30 s, 72° C./2 min:
25 cycles)

A gene fragment was obtained that encoded the EGFR extracellular region and that had a 5' NotI site and a 3' BglII site. This fragment was digested with NotI-BglII and inserted between NotI-BamHI in pCV_mG-CSFR.

The expression plasmid vector pCV was constructed by replacing the poly(A) addition signal of pCOS1 (International Publication No. WO 98/13388) with the poly(A) addition signal from human G-CSF. pEF-BOS (Mizushima S. et al., Nuc. Acids Res. 18, 5322 (1990)) was digested with EcoRI and XbaI to obtain the poly(A) addition signal fragment originating from human G-CSF. This fragment was inserted into pBacPAK8 (Clontech Laboratories, Inc.) at the EcoRI/XbaI sites. After digested with EcoRI, both terminals were blunted and digested with BamHI, resulted in the production of a fragment containing the poly(A) addition signal of human G-CSF origin having a BamHI site added at the 5' terminal and a blunted 3' terminal. This fragment was exchanged with the poly(A) addition signal of pCOS1 at the BamHI/EcoRV sites, giving the expression plasmid vector designated pCV.

pCV_mG-CSFR comprises the mouse G-CSF receptor from the asparagine residue at position 623 to the C terminal, which is the intracellular region, in pCV. The base sequence (M58288) of the mouse G-CSF receptor is shown in SEQ ID NO: 65 and the amino acid sequence (AAA37673) of the mouse G-CSF receptor is shown in SEQ ID NO: 66. However, the glycine reside at position 632 in SEQ ID NO: 66 is replaced by a glutamic, acid residue due to the creation of a BamHI site (restriction enzyme site) in the coding cDNA sequence at the N-terminal region in the insertion sequence of pCV_mG-CSFR.

Construction of the vector pCV_hEGFR/mG-CSFR expressing the chimeric receptor hEGFR/mG-CSFR composed of the extracellular region of human EGFR and the intracellular region of mouse G-CSFR was completed by confirming the base sequence of the gene fragment inserted in pCV_mG-CSFR.

The base sequence and amino acid sequence for the protein expressed by the expression vector, i.e., a human EGFR/mouse G-CSFR chimeric receptor, are shown, respectively, in SEQ ID NO: 67 and SEQ ID NO: 68.

2-3-2. Creation of an HB-EGF-Dependent Cell Line

15 μg of the hEGFR/mG-CSFR chimeric receptor expression vector pCV_hEGFR/mG-CSFR, linearized by digestion with pvuI, was transfected by electroporation (Gene Pulser, Bio-Rad Laboratories, Inc.) at 0.33 kV, 950 μF into Ba/F3 cells. These cells were cultured for 2 weeks on medium (RPMI1640, 10% FCS, PS) containing 10 ng/mL HB-EGF and 500 μg/mL G418 and the emergent colony was picked up.

It was then determined in the following experiment if the obtained cell line exhibited growth dependent on the HB-EGF concentration. The EGFR_Ba/F3 cells were seeded to 96-well plates at 1×10³ cells/well in the presence of 0 to 100 ng/mL HB-EGF (R&D Systems, Inc., 259-HE) followed by incubation for 3 days. Then the cell count was measured using the WST-8 reagent (Cell Counting Kit-8, Dojindo Laboratories) in accordance with the manufacturers instructions.

The results showed that growth of the established EGFR_Ba/F3 cell line was promoted in a manner dependent on the HB-EGF concentration (FIG. 2b).

2-4. Hybridoma Screening 2-4-1. Screening for HB-EGF-Binding Antibodies (Primary Screening)

In order to obtain anti-HB-EGF neutralizing antibodies, HB-EGF-binding antibodies was first screened. ELISA and FACS were used to screen for binding antibodies.

2-4-1-1. ELISA

The hybridoma culture supernatant was reacted by incubation for 1 hour in ELISA plates (NUNC) coated with 1 μg/mL HB-EGF protein (R&D Systems, Inc., 259-HE). This was followed by reaction for 1 hour with alkali phosphatase (AP)-labeled anti-mouse IgG (Zymed Laboratories, Inc., #62-6622), after which color development was brought about by the addition of 1 mg/mL substrate (Sigma, S0942-50TAB). The $OD_{405}$ was measured with a plate reader (Bio-Rad Laboratories, Inc.) and the ELISA-positive wells were selected.

2-4-1-2. FACS

The hybridoma culture supernatant was added to HB-EGF_Ba/F3 cells (approximately 1×10⁵ cells) and incubated for 1 hour at 4° C. FITC-labeled anti-mouse IgG antibody (Beckman Coulter, PN IM0819) was then added and incubated for 30 minutes at 4° C. The binding activity to cell surface HB-EGF was then analyzed for each hybridoma culture supernatant by FACS (Becton, Dickinson and Company).

2-4-1-3. Limit Dilution

Limit dilution (LD) was carried out in order to divide the clones exhibiting HB-EGF binding activity according to ELISA or FACS analysis into monoclones. The cell count in positive wells was measured, and seeding to 96-well plates was done so as to provide 3 cells/well. After incubation for approximately 10 days, the binding activity was again analyzed by ELISA or FACS on the culture supernatant in wells in which colonies had emerged. Using this series of procedures, five monoclones exhibiting HB-EGF binding activity were obtained in the HA series, four monoclones exhibiting HB-EGF binding activity were obtained in the HB series, and five monoclones exhibiting HB-EGF binding activity were obtained in the HC series.

2-4-1-4. Subtype Determination

The antibody subtype was determined using IsoStrip (Roche #1,493,027). The hybridoma culture supernatant diluted 10 times with PBS (−) was used for subtype determination.

TABLE 1

Characteristics of the isolated antibodies

| mouse strain | clone ID | EXP. 1 | | EXP. 2 | | iso-type |
| | | ELISA (OD405) | FACS (CEO-mean) | ELISA (OD405) | FACS (CEO-mean) | |
|---|---|---|---|---|---|---|
| | no-mAb | | 19.1 | | 6.9 | |
| bab #1 | HA-1 | 0.40 | 17.1 | | | 2b |
| | HA-3 | 0.42 | 59.0 | | | 2a |
| | HA-9 | 4.00 | 18.1 | | 10.2 | 2b |
| | HA-10 | 2.68 | 17.7 | | | G1 |
| | HA-20 | 4.00 | 18.9 | | | G1 |
| bab #2 | HB-10 | 2.55 | 108.0 | | | 2a |
| | HB-13 | 1.42 | 21.2 | | | G1 |
| | HB-20 | 3.91 | 188.2 | 4.00 | 98.9 | 2a |
| | HB-22 | 1.34 | 450.4 | | | 2b |
| MRL #1 | HC-15 | | 594.1 | 4.00 | 233.8 | 2a |
| | HC-19 | | 65.1 | 0.06 | 41.7 | 2a |
| | HC-26 | | 149.2 | 0.05 | 60.6 | 2a |
| | HC-42 | | 47.5 | 0.05 | 40.5 | 2a |
| | HC-74 | | | 0.05 | 45.2 | 2a |

2-4-2. Antibody Purification

The antibody was purified from 80 mL of the culture supernatant for the obtained monoclonal hybridoma using a HiTrap Protein G HP 1 mL column (Amersham Biosciences #17-0404-01). The hybridoma supernatant was adsorbed at a flow rate of 1 mL/min followed by washing with 20 mL 20 mM phosphate buffer (pH 7.0) and then elution with 3.5 mL 0.1 M glycine-HCl (pH 2.7). The eluate was recovered in 0.5 mL fractions in Eppendorf tubes, each of which already contained 50 μL 1 M Tris-HCL (pH 9.0). The $OD_{280nm}$ was measured. The fractions containing antibody were combined and PBS (−) was added to bring to a total of 2.5 mL, then the buffer was replaced to PBS(−) using a PD-10 column (Amersham Biosciences #17-0851-01). The purified antibody was passed through a 0.22 μm filter (Millipore #SLGV033RS) and the properties of the individual purified antibodies were investigated in detail as follows.

2-4-3. Analysis of the Growth Neutralizing Activity in EGFR_Ba/F3 Cells (Secondary Screening)

The neutralizing activity on the HB-EGF-dependent growth of EGFR_Ba/F3 cells was analyzed for each of the purified antibodies. EGFR_Ba/F3 cells were seeded to 96-well plates at 2×10⁴ cells/well in the presence of HB-EGF (80 ng/mL) and the particular purified antibody was added at 0 to 200 ng/mL. After incubation for 3 days, the cell count was measured using WST-8 (Cell Counting Kit-8).

The results showed that HA-20 in the HA series, HB-20 in the HB series, and HC-15 in the HC series exhibit a strong neutralizing activity (FIGS. 3a to 3c).

Analysis of the Properties of HB-EGF Neutralizing Antibodies (HA-20, HB-20, HC-15)

3-1. Cloning of the Variable Region and Determination of the Amino Acid Sequence for HA-20, HB-20, and HC-15

The total RNA was purified using Trizol (#15596-018, Life Technologies) from approximately $5 \times 10^6$ hybridomas. Using a SMART RACE cDNA Amplification Kit (Clontech Laboratories, Inc., #PT3269-1), full-length cDNA synthesis was carried out according to the manual provided with the kit from 1 µg of the obtained total RNA. For each antibody, the gene encoding the variable region of the heavy chain (VH) and the variable region of the light chain (VL) was amplified using the obtained cDNA as template and an Advantage 2 PCR Enzyme System (Clontech Laboratories, Inc. #PT3281-1).

Cloning Primers for the Light Chain Variable Region

UPM—k(VL-k)

UPM: provided with the kit

```
VL-k:
   GCT CAC TGG ATG GTG GGA AGA TG   (SEQ ID NO: 69)
```

Cloning Primers for the Heavy Chain Variable Region

HA-20: UPM—VH-G1

HB-20, HC-15: UPM—VH-2a

UPM: provided with the kit

```
VH-G1:
GGG CCA GTG GAT AGA CAG ATG          (SEQ ID NO: 70)

VH-2a:
CAG GGG CCA GTG GAT AGA CCG ATG      (SEQ ID NO: 71)

94° C./5 s, 72° C./2 min, 5 cycles

94° C./5 s, 70° C./10 s, 72° C./2 min, 5 cycles

94° C./5 s, 68° C./10 s, 72° C./2 min,
27 cycles
```

The gene fragments amplified in the preceding procedures were TA-cloned into pCR11—TOPO (Invitrogen TOPO TA-cloning Kit, #45-0640) and the base sequence for each insert was identified. The identified variable region sequences are shown in FIG. 4A and FIG. 4B.

3-2. Analysis of the Binding Activity for the Active Form of HB-EGF

The following experiment was run in order to compare the ability of the thus obtained three antibodies (HA-20, HB-20, HC-15) to bind to active-form HB-EGF protein. The HA-20, HB-20, or HC-15 antibody was reacted at various concentrations in ELISA plates (NUNC) coated with 1 µg/mL HB-EGF protein (R&D Systems, Inc., 259-HE). This was followed by reaction for 1 hour with alkali phosphatase (AP)-labeled anti-mouse IgG (Zymed Laboratories, Inc., #62-6622), and addition of 1 mg/mL substrate (Sigma, 50942-50TAB) for color development. The OD405 was measured with a plate reader and the antibody concentration that gave 50% binding ($ED_{50}$) was calculated based on the binding curve obtained for the particular antibody. With regard to the binding activity for active-form HB-EGF, $ED_{50}$ values of 0.2 to 1.4 nM were observed and a strong binding activity was thus found to be present in all instances (FIG. 5).

TABLE 2

$ED_{50}$ value for binding to HB-EGF for the antibodies HA-20, HB-20, and HC-15

| mAb | HB-EGF binding ($ED_{50}$, nmol/L) |
|---|---|
| HA-20 | 0.8 |
| HB-20 | 1.4 |
| HC-15 | 0.2 |

3-3. Analysis of the Binding Activity for proHB-EGF

The binding activity for proHB-EGF was then analyzed for the obtained three antibodies. RMG1 cells (ovarian cancer cell line, purchased from the Japan Health Sciences Foundation), which are known to intrinsically express HB-EGF, were cultured on a growth medium (Ham's F12 medium, Invitrogen Corporation) containing 10% FCS. Each of the antibodies (10 µg/mL) was reacted for 1 hour at 4° C. with the RMG1 cells, which intrinsically expressed HB-EGF, and the Ba/F3 cells (HB-EGF_Ba/F3), HB-EGF-expressing DG44 cells (HB-EGF_DG44), and SKOV-3 cells (HB-EGF_SKOV-3), which were cells overexpressing HB-EGF, followed by staining with FITC-labeled anti-mouse IgG antibody (Beckman Coulter, PN IM0819). Binding to the cell surface HB-EGF was then analyzed by FACS (Becton, Dickinson and Company) for each antibody.

The histograms shown in FIG. 6 compare the binding activity of the HA-20, HB-20, and HC-15 antibodies according to FACS analysis to the proHB-EGF intrinsically expressed in RMG1 cells and the proHB-EGF overexpressed in the Ba/F3, DG44, and SKOV-3 cells. The grey waveform shows the staining pattern in the absence of the primary antibody (control), while the staining pattern in the presence of the particular antibody is shown with a solid line. The horizontal axis shows the staining intensity and the vertical axis shows the number of cells. As shown in FIG. 6, HB-20 and HC-15 recognized the HB-EGF overexpressed on the cell membrane and the HB-EGF intrinsically expressed on the cell membrane by the ovarian cancer line, while the HA-20 either did not bind at all or was bound only very weakly. These results showed that HA-20 was an antibody that, while strongly binding to active-form HB-EGF, did not recognize proHB-EGF.

3-4. Analysis of the Neutralizing Activity 3-4-1. Solid-Phase Analysis of the Ability to Inhibit EGFR/HB-EGF Binding 3-4-1-1. Production of EGFR-Fc Protein In order to construct an ELISA system that could check binding between HB-EGF and its receptor (EGFR) under solid phase conditions, a fusion protein (EGFR-Fc) from the extracellular region of EGFR and the Fc region of human IgG1 was first prepared to serve as the receptor protein. The mode of inhibition of binding between HB-EGF and EGFR by HB-EGF antibody on the solid phase are schematically illustrated in FIG. 7.

An EGFR-Fc expression vector was first constructed. PCR was carried out using the following primers and using the pCV_hEGFR/mG-CSFR constructed in example 2-3-1 as the template.

```
EGFR-7:
                                   (SEQ ID NO: 72)
GTTAAGCTTCCACCATGCGACCCTCCGGGAC

EGFR-8:
                                   (SEQ ID NO: 73)
GTTGGTGACCGACGGGATCTTAGGCCCATTCGTTG (94° C./30 s, 72° C./30 s: 25 cycles)
```

The amplified gene fragment coding for the extracellular region of EGFR was cleaved with BstEII and HindIII and was inserted between BstEII-HindIII in pMCDN2-Fc. The base sequence of the inserted gene fragment was confirmed to complete construction of a vector (pMCDN2_EGFR-Fc) expressing a fusion protein (EGFR-Fc) of the extracellular region of human EGFR and the Fc region of human IgG1. The base sequence and the amino acid sequence of the protein expressed by the expression vector, i.e., EGFR-Fc, are shown, respectively, in SEQ ID NO: 74 and SEQ ID NO: 75.

An EGFR-Fc protein-producing cell line was then established as follows. 15 μg of the EGFR-Fc expression vector pMCDN2_EGFR-Fc was first digested with pvuI and was then transfected by electroporation into DG44 cells. The EGFR-Fc protein produced in the culture supernatant of the G418-resistant strains was subsequently analyzed by Western blotting. Thus, 10 μL of the particular culture supernatant was separated by SDS-PAGE; blotted to a PVDF membrane; and the target protein was detected with HRP-labeled anti-human IgG antibody (Amersham, NA933V). The clone providing the highest production level was selected and run through expansion culture and the culture supernatant was recovered.

Purification of the EGFR-F protein was carried out as follows. The culture supernatant from the obtained EGFR-Fc-producing strain was adsorbed at a flow rate of 1 mL/min on a HiTrap Protein G HP 1 mL column (Amersham Biosciences #17-0404-01). After washing with 20 mL 20 mM phosphate buffer (pH 7.0), the protein was eluted with 3.5 mL 0.1 M glycine-HCl (pH 2.7). To identify the fraction containing the target protein, 10 μL of each of the recovered fractions was separated by SDS-PAGE followed by Western blotting and staining with Coomassie Brilliant Blue. The buffer was replaced to PBS(−) using a PD-10 column (Amersham Biosciences #17-0851-01). The purified protein was passed through a 0.22 μm filter (Millipore #SLGV033RS) and was stored at 4° C.

3-4-1-2. Analysis of Binding Between HB-EGF and EGFR Using ELISA

The purified EGFR-Fc was reacted at 0.5 μg/mL for 1 hour in ELISA plates coated with anti-human IgG antibody. 0 to 250 ng/mL HB-EGF (R&D Systems, Inc., 259-HE) was reacted for 1 hour, followed by detection of the HB-EGF protein bound to the EGFR-Fc with biotin-labeled anti-HB-EGF antibody (R&D Systems, Inc., BAF259) and AP-labeled streptavidin (Zymed, #43-8322). The model for analyzing the EGFR/HB-EGF binding mode using ELISA is shown in FIG. 8. The results showed that HB-EGF binding to EGFR could be detected with the solid-phase system beginning at a concentration of about 4 ng/mL (FIG. 9).

3-4-1-3. Analysis of the Antibody-Mediated Inhibitory Activity on HB-EGF/EGFR Binding The solid-phase system described in the preceding was used to analyze the inhibitory activity on HB-EGF/EGFR binding by the antibodies obtained in 2-4-2. The individual antibody and HB-EGF (50 ng/mL) were added to ELISA plates on which EGFR-Fc had been immobilized and a reacted for one hour at room temperature. The plates were washed with TBS-T and the HB-EGF bound to the EGFR was detected by the previously described procedure (FIG. 10).

A concentration-dependent activity to inhibit binding was observed for all the antibodies, and a particularly strong binding inhibition was recognized for HA-20, HB-20, and HC-15.

3-4-2. Growth Inhibiting Activity on EGFR_Ba/F3 Cells

The neutralizing activity on the HB-EGF-dependent growth of EGFR_Ba/F3 cells was compared for HA-20, HB-20, and HC-15. As above, the EGFR_Ba/F3 cells were seeded to 96-well plates at 2×10⁴ cells/well in the presence of HB-EGF (80 ng/mL) and the particular purified antibody was added. After cultivation for 3 days, the cell count was measured using WST-8 (Cell Counting Kit-8) and a growth curve was constructed. The antibody concentration at 50% of the maximum inhibitory effect ($EC_{50}$ value) was calculated based on the obtained results.

According to the results, the strongest growth inhibiting effect on EGFR_Ba/F3 cells was exhibited by HC-15 ($EC_{50}$=3.8 nM) followed by HA-20 ($EC_{50}$=32.6 nM) and HB-20 ($EC_{50}$=40.3 nM) (FIG. 11).

TABLE 3

$ED_{50}$ values exhibited by HA-20, HB-20, and HC-15 antibodies for the growth-inhibiting effect on EGFR_Ba/F3 cells

|  | HA-20 | HB-20 | HC-15 |
|---|---|---|---|
| EC50 (nM) | 32.6 | 40.3 | 3.8 |

3-4-3. Growth Inhibiting Activity for RMG-1 Cells

The neutralizing activity on RMG-1 cells was analyzed as follows. RMG-1 cells (6×10³ cells/well) were seeded into Ham's F12 medium containing 8% or 2% FCS in 96-well plates and the particular antibody was then added. After cultivation for one week, the cell count was measured using the WST-8 reagent.

According to the result, HA-20 inhibited the growth of RMG-1 cells in an antibody concentration-dependent manner (FIG. 12). The growth inhibiting activity was particularly significant at a 2% FCS concentration.

3-5. Analysis of the Cytotoxicity Mediated by the Antibody's Internalizing Activity 3-5-1. System for Evaluating the Internalizing Activity-Mediated Induction of Cell Death The activity to induce cell death through antibody internalization was evaluated using a saporin (toxin)-labeled anti-mouse IgG antibody (Mab-ZAP, Advanced Targeting Systems). An indirectly toxin-labeled antibody was first prepared by mixing the primary antibody and Mab-ZAP and reacting for 15 minutes at room temperature, and added to the target cells. When the added antibody was internalized into the cells, the Mab-ZAP was then also incorporated into the cells along with the primary antibody, resulted in the induction of cell death by the saporin released within the cell. This is shown schematically in FIG. 13.

3-5-2. Internalization-Mediated Induction of Cell Death in a High HB-EGF-Expressing Cell Line The antibody was examined using HC-15 for its ability to induce cell death by the internalizing activity. SKOV-3 cells and HB-EGF_SKOV3 cells (SKOV-3 cells that overexpress HB-EGF) were seeded to 96-well plates at 2×10³ cells/well. After culture overnight, Mab-ZAP was reacted, at 100 ng/well, with the obtained anti-HB-EGF antibody (100 ng/well) and added to the cells. A viable cell count was taken using WST-8 four days after antibody addition. In the case of the original SKOV-3 cells, which only weakly expressed HB-EGF, an ability to induce cell death was not seen for any of the antibodies; however, for the SKOV-3 cells that overexpressing HB-EGF, a cell death inducing activity in the presence of Mab-ZAP was seen for each antibody. In particular, a strong cell death inducing activity was seen for HB-20 and HC-15, which bind to proHB-EGF (FIG. 14).

3-5-3. Internalization-Mediated Cell Death Induction in an Ovarian Cancer Line 3-5-3-1. Analysis of Cytotoxicity for an Ovarian Cancer Line (ES-2)

3-5-3-1-1. Binding Activity for ES-2 by Individual Antibodies

The ability to induce cell death in an ovarian cell line that intrinsically expresses HB-EGF (ES-2) was then investigated. ES-2 cells (ovarian cancer cell line, purchased from the ATCC) were cultured in a growth medium (McCoy's 5A medium, Invitrogen Corporation) containing 10% FCS and penicillin/streptomycin (P/S).

The ability of each antibody to bind to the cell surface of ES-2 cells was first analyzed using FACS. The cells were detached with 1 mM EDTA; the cells and the particular antibody (10 µg/mL) were reacted for 1 hour at 4° C. in FACS buffer (PBS containing 2% FCS and 0.05% $NaN_3$); and stained with FITC-labeled anti-mouse IgG antibody (Beckman Coulter, PN IM0819) for 30 minutes at 4° C. The antibody binding to the HB-EGF expressed on the cell surface was analyzed using FACS (Becton, Dickinson and Company).

FIG. 15 provides histograms that compare, via FACS analysis, the binding activity of the HA-20, HB-20, and HC-15 antibodies for ES-2 cells. The grey waveform shows the staining pattern in the absence of the primary antibody (control), while the staining pattern in the presence of the particular antibody is shown with a solid line. The horizontal axis shows the staining intensity and the vertical axis shows the number of cells. As shown in FIG. 15, binding to the HB-EGF expressed on the cell membrane of ES-2 cells was detected in particular for HC-15.

3-5-3-1-2. Ability to Induce Cell Death in ES-2

Internalization-mediated cytotoxicity of each antibody for ES-2 cells was investigated. ES-2 cells were seeded at $2\times10^3$ cells/well to 96-well plates. After culture overnight, the particular antibody (100 ng/well) and Mab-ZAP (100 ng/well) were reacted and added to the cells. After three days, the viable cell count was measured using WST-8. According to the results shown in FIG. 16, a cell death inducing activity in the presence of Mab-ZAP was seen for HC-15, which exhibited the strongest HB-EGF binding activity.

3-5-3-2. Analysis of the Ability to Inhibit the Growth of Ovarian Cancer Lines (RMG-1, MCAS)

3-5-3-2-1. Binding Activity of HC-15 for MCAS and RMG-1

The ability of the antibodies to inhibit growth was then investigated using separate ovarian cancer cell lines (RMG-1, MCAS). MCAS cells (purchased from JCRB) were cultured on a growth medium (Eagle's Minimal Essential Medium, Invitrogen Corporation) that contained 20% FCS.

In order to investigate whether and to what degree MCAS and RMG-1 express HB-EGF on the cell surface, FACS analysis was carried out using the HC-15 antibody. The cells were detached with 1 mM EDTA; the cells and the HC-15 antibody (10 µg/mL) were reacted for 1 hour at 4° C. in FACS buffer (PBS containing 2% FCS and 0.05% $NaNO_3$) ; and stained with FITC-labeled anti-mouse IgG antibody (Beckman Coulter, PN IM0819) for 30 minutes at 4° C. The antibody binding to the HB-EGF expressed on the cell surface was analyzed using FACS (Becton, Dickinson and Company).

Histograms are provided in FIG. 17 that compare, via FACS analysis, the binding activity by the HC-15 antibody for RMG-1 and MCAS cells. It was revealed that HB-EGF was expressed on the cell surface of both the RMG-1 cells and the MCAS cells.

3-5-3-2-2. Analysis Using the Soft Agar Colony Formation Assay of the Ability of the Antibodies to Inhibit the Proliferation of RMG-1 and MCAS The activity of the antibodies on the anchorage-independent proliferation of RMG-1 and MCAS cells was then investigated using the soft agar colony formation assay. The soft agar colony formation assay was carried out as described in the following.

MEM medium containing 0.6% agar (3:1 NuSieve, Cambrex) was added at 100 µL/well to each well in 96-well plates in order to prepare agar bottoms. The cells were then suspended at 8000 cells/well in medium containing 0.3% agar. Each test substance (antibody, Mab-ZAP) was mixed together with the cells into the agar; the preparation was dripped at 100 µL/well onto the agar bottoms. After cultivation at 37° C. for from 3 weeks to 1 month, the emerged colonies were stained with 1% iodonitrotetrazolium chloride (Sigma, 18377) and the colonies were examined under a microscope.

The action of individual antibodies (HA-20, HC-15) on colony formation by RMG-1 cells was first analyzed. The HA-20 or HC-15 antibody was mixed into the RMG-1 cells so as to provide 50 µg/mL, and the colonies formed in the agar were observed after approximately 3 weeks. According to the results, colony formation by the RMG-1 cells had been inhibited in the HC-15 antibody addition group in comparison to the non-addition group (FIG. 18). It was thus found that the HC-15 antibody, just through its neutralizing activity alone, could inhibit anchorage-independent colony formation by RMG-1 cells.

The toxin-mediated activity to inhibit colony formation was then analyzed for the HA-20 and HC-15 antibodies. Mab-ZAP (1 µg/mL) was mixed into the agar together with the RMG-1 cells and MCAS cells and HA-20 or HC-15 antibody (10 µg/mL), and cultured for approximately 3 weeks to 1 month. The colonies formed was stained and observed by microscopy.

According to the results, an inhibition of colony formation was observed due to the simultaneous addition of HC-15 antibody and Mab-ZAP in both the RMG-1 cells (FIG. 19) and the MCAS cells (FIG. 20). Based on the preceding, it was demonstrated that the HC-15 antibody can inhibit the ability of ovarian cancer cells to form colonies not only through the exhibition of its neutralizing activity but also through the exhibition of an internalization activity.

3-5-4. Internalization-Mediated Cell Death Induction in Hematological Cancer Lines 3-5-4-1. Analysis of HB-EGF Expression by Hematological Cancer Lines It was then examined whether the internalization-mediated antitumor effect of HC-15 is also seen with hematological cancers. The following were cultured on RPMI1640 (Invitrogen Corporation) containing 10% FCS: RPMI8226 (multiple myeloma, purchased from the ATCC), Jurkat (acute T-cell leukemia, purchased from the ATCC), HL-60 (acute myeloid leukemia, purchased from JCRB), THP-1 (acute monocytic leukemia, purchased from JCRB), and U937 (monocytic leukemia, purchased from JCRB).

FACS analysis was carried out to investigate the expression of HB-EGF by these cells. The HC-15 (10 µg/mL) antibody was reacted with the particular cell line ($2\times10^5$ cells) for 60 minutes on ice, and stained with FITC-labeled anti-mouse IgG antibody (Beckman Coulter, PN IM0819). Binding by the antibody to the HB-EGF expressed on the cell surface was then analyzed by FACS (Becton, Dickinson and Company).

Histograms are given in FIG. 21 that compare, based on FACS analysis, the expression of HB-EGF by the individual hematological cancer cell lines. THP-1 and U937 were shown to exhibit a particularly strong HB-EGF expression. In contrast, almost no expression was seen with Jurkat and RPMI8226.

3-5-4-2. Analysis of Cytotoxicity for Hematological Cell Lines

The particular hematological cell line was seeded to 96-well plates at 1 to $2 \times 10^4$ cells/well. Mab-ZAP was then reacted, at 100 ng/well, with the particular anti-HB-EGF antibody (100 ng/well) and added to the cells. Five days after antibody addition, the viable cell count was measured using WST-8. An inhibition of proliferation was seen for the simultaneous addition of HC-15 antibody and Mab-ZAP to U937 cells and THP-1 cells. Based on these results, the internalization activity of the HC-15 antibody was shown to be effective as an antitumor agent against several hematological cancers.

Analysis of Cell Death Induction by Saporin-Labeled Antibodies 4-1. Saporin Labeling of the Antibodies Cytotoxicity mediated by the antibody's internalization activity was investigated using HA-20 antibody directly labeled with toxin (HA-SAP) and HC-15 antibody directly labeled with toxin (HC-SAP).

Saporin labeling of the purified HA-20 antibody and purified HC-15 antibody was outsourced to Advanced Targeting Systems. Antibodies were thus obtained consisting of HA-20 labeled with an average of 3 saporin molecules and HC-15 labeled with an average of 2.4 saporin molecules (respectively designated HA-SAP and HC-SAP). These were employed in an investigation of the ability to induce cell death in cancer cells.

4-2. Analysis of the Cytotoxicity of Saporin-Labeled Antibodies 4-2-1. Analysis of the Cytotoxicity of Saporin-Labeled Antibodies for Solid Cancer Cell Lines The following cancer cells were used in the analysis: ES-2, MCAS (ovarian cancer), Capan-2 (pancreatic cancer, purchased from the Japan Health Sciences Foundation), BxPC-3, 22Rv1 (prostate cancer, purchased from the ATCC), and HUVEC (human endothelial cells, purchased from Takara Bio Inc.). These cells were in each case cultured using the culture conditions indicated in the instructions supplied by the vendor.

The cytotoxicity was analyzed as follows. Each of the cell lines was seeded to 96-well plates at 1 to $5 \times 10^3$ cells/well and cultured overnight. The next day, HA-SAP, HC-SAP, or the control antibody (saporin-labeled mouse IgG (IgG-SAP), Advanced Targeting Systems) was added so as to provide from approximately 100 nM to 1 fM and cultured for 3 to 5 days. The viable cell count was measured using WST-8.

According to the results shown in FIG. 23a, HC-SAP strongly induced cell death in ES-2 and MCAS, which are ovarian cancer cell lines. The HC-SAP activity was as follows: $EC_{50}=0.09$ nM in ES-2 cells, $EC_{50}=0.86$ nM in MCAS cells. On the other hand, no effect at all was shown against HUVEC (normal human endothelial cells).

4-2-2. Analysis of the Cytotoxicity Exhibited by Saporin-Labeled Antibodies on Hematological Cancer Cell Lines The following cell lines were cultured on RPMI1640 (Invitrogen Corporation) containing 10% FCS: RPMI8226 (multiple myeloma, purchased from the ATCC), HL-60 (acute myeloid leukemia, purchased from JCRB), SKM-1 and THP-1 (acute monocytic leukemia, purchased from JCRB), and U937 (monocytic leukemia, purchased from JCRB).

The cytotoxicity exhibited by HA-SAP and HC-SAP on these hematological cancer cell lines was examined as follows. Each of the cell lines was seeded to 96-well plates at 1 to $5 \xi 10^3$ cells/well followed by the addition of HA-SAP or HC-SAP at from approximately 100 nM to 1 fM and cultivation for 3 to 5 days. The viable cell count was then measured using WST-8.

According to the results shown in FIG. 23b, cell death was substantially induced by HC-SAP in the U937, SKM-1, and THP-1 cells. The HC-SAP activity was as follows: $EC_{50}=0.33$ nM for U937 cells, $EC_{50}=0.02$ nM for SKM-1 cells, and $EC_{50}=0.01$ nM for THP-1 cells. These results showed that an antibody labeled with, for example, toxin, and targeted to HB-EGF was also effective on hematological cancers.

DNA Immunization 5-1. Construction of an Expression Vector for Secreted-Form HB-EGF An expression vector for the secreted form of HB-EGF was constructed as follows. PCR was first carried out under the following conditions using Pyrobest Taq polymerase (Takara Bio Inc.) and the HB-EGF expression vector pMCN_HB-EGF as template, in order to amplify a fragment coding for the extracellular region of HB-EGF (amino acids 1-148).

```
EGF-9:
                                       (SEQ ID NO: 91)
TCC GAA TTC CAC CAT GAA GCT GCT GCC GTC GGT G

EGF-10:
                                       (SEQ ID NO: 92)
TTT GCG GCC GCT AGA GGC TCA GCC CAT GAC ACC T (94° C./30 s, 65° C./30 s, 72° C./30 s:
25 cycles)
```

The resulting PCR product was digested with EcoRI and NotI. The resulting DNA fragment was inserted between EcoRI and NotI in the pMCDN2 expression vector for animal cells, thus constructing the pMCDN_sHB-EGF expression vector for secreted-form HB-EGF.

5-2. DNA Immunization

50 μg of the secreted-form HB-EGF expression vector pMCDN_sHB-EGF was coated on gold particles according to the instructions (#165-2431) provided by Bio-Rad Laboratories, Inc. The DNA-conjugated gold particles obtained in this manner were coated within tubing using a Tubing Prep Station (Bio-Rad Laboratories, Inc.), and the tubing was cut to a suitable length with a tubing cutter, and stored as the immunizing DNA at 4° C.

DNA immunization was then carried out. Using a Helios Gene Gun (Bio-Rad Laboratories, Inc.), DNA was introduced by bombardment into the abdomen to three animals [(MRL/lpr, male, age: 4 weeks) (balb/c, female, age: 6 weeks), purchased from Charles River Japan]. Then a total of eleven immunizations were given by the same procedure at 3 to 4 day intervals. For the final immunization, 50 μg HB-EGF_Fc was suspended in 100 μL PBS and injected into the tail vein. Cell fusion was carried out three days later. Hybridoma were prepared by the same procedure as in 1 to 3.

The process of screening the candidate antibodies by comparing the clones with regard to HB-EGF binding activity and neutralizing activity was conducted by the same procedures as described in 2-4. Then, limit dilution, subtype determination, and antibody purification were carried out by the methods described in 2-4. The antibody HE-39, which exhibited a strong HB-EGF binding activity and neutralizing activity, was finally obtained by the DNA immunization.

Analysis of the properties of the novel HB-EGF-neutralizing antibody (HE-39)

6-1. Analysis of the Ability of HE-39 to Bind to Active-Form HB-EGF

The following experiment was carried out in order to compare the ability of the obtained HE-39 to bind to active-form HB-EGF protein with that of the three previously obtained antibodies (HA-20, HB-20, HC-15). The HA-20, HB-20, HC-15, or HE-39 antibody was reacted at various concentrations in ELISA plates (NUNC) coated with 1 μg/mL HB-EGF protein (R&D Systems, Inc., 259-HE), reacted with alkali phosphatase (AP)-labeled anti-mouse IgG (Zymed Laboratories, Inc., #62-6622), for 1 hour. Color development was brought about by the addition of 1 mg/mL substrate (Sigma, S0942-50TAB). The $OD_{405}$ was measured with a plate reader and the antibody concentration that gave 50% binding ($ED_{50}$) was calculated based on the binding curve obtained for the particular antibody. As a result, the binding activity by HE-39 for active-form HB-EGF was shown to have an $ED_{50}$ value of approximately 0.016 nM, and HE-39 was thus shown to have a much stronger binding activity than the other three antibodies (FIG. 24).

TABLE 4

| Binding to HB-EGF ($ED_{50}$, nmol/L) | | | |
|---|---|---|---|
| HA20 | HB20 | HC15 | HE39 |
| 3.01 | 5.49 | 0.65 | 0.016 |

6-2. Analysis of the Binding Activity by HE-39 for proHB-EGF

The following experiment was run in order to compare the binding activity by HE-39 for proHB-EGF with that of the three previously obtained antibodies (HA-20, HB-20, and HC-15).

The particular antibody (10 μg/mL) was reacted for 1 hour at 4° C. with HB-EGF-expressing DG44 cells (HB-EGF_DG44) followed by staining with FITC-labeled anti-mouse IgG antibody (Beckman Coulter, PN IM0819). Binding by the particular antibody to the cell surface HB-EGF was subsequently analyzed by FACS (Becton, Dickinson and Company).

Histograms are provided in FIG. 25 that compare, based on FACS analysis, the binding activities of the antibodies HA-20, HB-20, HC-15, and HE-39 for the proHB-EGF overexpressed in DG44 cells. The grey waveform shows the staining pattern in the absence of the primary antibody (control), while the staining pattern in the presence of the particular antibody is shown with a solid line. The horizontal axis shows the staining intensity and the vertical axis shows the number of cells. As shown in FIG. 25, the HE-39 antibody, like HB-20 and HC-15, was an antibody that recognized the HB-EGF on the cell membrane.

6-3. Analysis of the Neutralizing Activity 6-3-1. Ability to Inhibit Binding by HB-EGF to EGFR The ability of the HE-39 antibody to inhibit binding between HB-EGF and EGFR was compared with that of the three previously obtained antibodies (HA-20, HB-20, and HC-15) using the solid-phase evaluation system described in 3-4-1. HB-EGF (50 ng/mL) and the serially diluted antibody were added to the ELISA plates on which EFGR-Fc had been immobilized, and reacted for 1 hour at room temperature. The plates were washed with TBS-T and HB-EGF bound to EGFR was detected by the procedure described in 3-4-1 (FIG. 26).

The results demonstrated that binding by HB-EGF to the receptor was strongly inhibited in particular by the HC-15 and HE-39 antibodies.

TABLE 5

| Inhibition of HB-EGF binding to EGFR ($EC_{50}$, nmol/L) | | | |
|---|---|---|---|
| HA20 | HB20 | HC15 | HE39 |
| 21.7 | 4.51 | 0.52 | 0.86 |

6-3-2. Ability to Inhibit the Growth of EGFR_Ba/F3 Cells

The neutralizing activity of the HE-39 antibody on the HB-EGF-dependent growth of EGFR_Ba/F3 cells was then analyzed and compared with the neutralizing activity of HA-20, HB-20, and HC-15. In accordance with the method described in 3-4-2, EGFR_Ba/F3 cells were seeded at $2 \times 10^4$ cells/well into 96-well plates in the presence of HB-EGF (80 ng/mL) and the particular purified antibody was added. After culture for 3 days, the cell count was measured using WST-8 (Cell Counting Kit-8) and a growth curve was constructed. The antibody concentration at 50% of the maximum inhibitory effect ($EC_{50}$ value) was calculated based on the obtained results.

According to the results, HE-39 exhibited a growth inhibiting activity ($EC_{50}$=0.83 nM) that was substantially better than that of HC-15 ($EC_{50}$=2.06 nM), which had otherwise exhibited the strongest growth inhibiting effect on EGFR_Ba/F3 cells (FIG. 27).

TABLE 6

| Inhibition of HB-EGF-dependent growth ($EC_{50}$, nmol/L) | | | |
|---|---|---|---|
| HA20 | HB20 | HC15 | HE39 |
| 9.52 | 9.51 | 2.06 | 0.83 |

Cloning of the Variable Regions of the HE-39 Antibody 7.1 Cloning of the Variable Regions Cloning of the variable regions of the HE-39 antibody and analysis of their amino acid sequences were carried out according to the methods described in 3-1. Since HE-39 is IgG1, the light chain variable region was cloned using the VL-k primer (SEQ ID NO: 69) and the heavy chain variable region was cloned using the VH-G1 primer (SEQ ID NO: 70).

The gene fragments amplified in the preceding procedure were TA-cloned into pCR11—TOPO (Invitrogen TOPO TA-Cloning Kit, #45-0640), after which the base sequence of each insert was identified. The identified variable chain sequences are shown in FIG. 28.

7-2. Identification of the Light Chain Variable Region

According to the results from cloning the variable regions, two different genes (VL-1, VL-2) were present for the light chain variable region originating from the HE-39 hybridoma. This led to the hypothesis that the HE-39 hybridoma had not been completely monocloned. Monocloning by limit dilution was therefore pursued again. HE-39 was seeded into a 96-well plate so as to give 1 cell/well. After culture for approximately 10 days, the culture supernatant from colony-emerged wells was analyzed with FACS using the HB-EGF-expressing Ba/F3 cells. As a result, three monoclonal antibodies exhibiting HB-EGF binding activity were obtained (HE39-1, HE39-5, HE39-14) as shown in FIG. 29a.

The following experiment was then carried out in order to identify which light chain variable regions (VL-1, VL-2) were expressed in these monocloned hybridomas.

The RNA was purified from each of the hybridomas (HE39, HE39-1, HE39-5, HE39-14) and the cDNA was synthesized using a SuperScript III First Strand System (Invitrogen Corporation). In order to examine which light chains were expressed in the individual hybridomas, RT-PCR was carried out with the synthesized cDNA originating from each hybridoma as template under the following conditions using a primer specific for the HE-39 heavy chain (HE39VH) and primers (HE39VL1, HE39VL2) specific for the two types of light chains (VL-1, VL-2).

HE-39 Heavy Chain Variable Region-Specific Primers

```
VH-G1:
GGG CCA GTG GAT AGA CAG ATG         (SEQ ID NO: 70)

HE39VH:
CTG GGT CTT TCT CTT CCT CCT GTC A   (SEQ ID NO: 93)
```

HE-39 light chain variable region-specific primers

```
VL-1
VL-k:
GCT CAC TGG ATG GTG GGA AGA TG      (SEQ ID NO: 69)

HE39VL1:
TGA GAT TGT GAT GAC CCA GAC TCC A   (SEQ ID NO: 94)

VL-2
VL-k:
GCT CAC TGG ATG GTG GGA AGA TG      (SEQ ID NO: 69)

HE39VL2:
TTC TCA CCC AGT CTC CAG CAA TCA     (SEQ ID NO: 95)

94° C./5 s, 72° C./2 min: 5 cycles

94° C./5 s, 70° C./10 s, 72° C./2 min: 5 cycles

94° C./5 s, 68° C./10 s, 72° C./2 min: 27 cycles
```

According to the Results, it was Determined as Shown in FIG. 29b that the two types of light chains (VL-1, VL-2) are expressed not only in HE39, but are also expressed in the hybridomas (HE39-1, HE39-5, HE39-14) that had been monocloned by the additional limit dilution. These results indicated that the two types, VL-1 and VL-2, are present in the light chain of HE-39.

Analysis of the Internalizing Activity of the HE-39 Antibody 8-1. Analysis of the Internalizing Activity-Mediated Cytotoxicity of the HE-39 Antibody The presence/absence of an internalizing activity-mediated cytotoxicity was also investigated for the HE-39 antibody obtained by DNA immunization.

HB-EGF_DG44 (DG44 cells that overexpress HB-EGF) were seeded at 2×10³ cells/well into 96-well plates. These cells were reacted with HA-20, HC-15, or HE-39 antibody (100 ng/well or 1000 ng/well) and Mab-ZAP (100 ng/well) and were cultured for 4 days, and measured for the viable cell count using WST-8.

An ability to induce cell death was seen for the groups in which both anti-HB-EGF antibody and Mab-ZAP were added. A particularly strong ability to induce cell death was seen for HC-15 and HE-39 (FIG. 30).

Epitope Analysis for the HE-39 Antibody 9-1. Analysis of the Binding Domain of the HE-39 Antibody HB-EGF has the structure shown in FIG. 31a. Mature-form HB-EGF is composed of two different domains, i.e., the heparin-binding domain and the EGF-like domain. The following E. coli expression vectors for the expression of GST fusion proteins were first constructed with the goal of determining which of these two domains is the domain recognized by the HE-39 antibody.

9-1-1. Preparing GST Fusion Protein Expression Vectors for Epitope Mapping 9-1-1-1. Construction of a GST-HBEGF Mature Expression Vector An expression vector for a GST protein/mature-form HB-EGF fusion protein was prepared as follows. PCR templated on the HB-EGF expression vector pMCN_HB-EGF was carried out under the following conditions using Pyrobest Taq polymerase (Takara Bio Inc.) in order to amplify a fragment encoding mature-form HB-EGF.

```
EGF11:
TTGGATCCGTCACTTTATCCTCCAAGCCACA    (SEQ ID NO: 96)

EGF12:
TTCTCGAGGAGGCTCAGCCCATGACACCT      (SEQ ID NO: 97)

(94° C./30 s, 65° C./30 s, 72° C./30 s:
30 cycles)
```

The obtained PCR product was then digested with BamHI and XhoI and was inserted downstream from the GST coding region of an E. coli GST fusion expression vector (pGEX-6P-1) that had been similarly digested with BamHI and XhoI, in order to construct a mature-form HB-EGF/GST fusion protein expression vector (pGEX-HBEGF mature).

9-1-1-2. Construction of a GST-HBEGF HBD Expression Vector

A vector expressing a GST protein/HBD (heparin-binding domain of HB-EGF) fusion protein was prepared as follows. PCR templated on the HB-EGF expression vector pMCN_HB-EGF was first carried out under the following conditions using Pyrobest Taq polymerase (Takara Bio Inc.) in order to amplify a fragment encoding the heparin binding domain.

```
EGF11:
TTGGATCCGTCACTTTATCCTCCAAGCCACA    (SEQ ID NO: 96)

EGF13:
TTCTCGAGCCGAAGACATGGGTCCCTCTT      (SEQ ID NO: 98)

(94° C./30 s, 65° C./30 s, 72° C./30 s:
30 cycles)
```

The obtained PCR product was then digested with BamHI and XhoI and was inserted downstream from the GST coding region of an E. coli GST fusion expression vector (pGEX-6P-1) that had been similarly digested with BamHI and XhoI, in order to construct an HB-EGF heparin binding domain/GST fusion protein expression vector (pGEX-HBEGF_HBD).

9-1-1-3. Construction of a GST-HBEGF EGFD Expression Vector

A vector expressing a GST protein/EGFD (EGF-like domain of HB-EGF) fusion protein was prepared as follows. PCR templated on the HB-EGF expression vector pMCN_HB-EGF was first carried out under the following conditions using Pyrobest Taq polymerase (Takara Bio Inc.) in order to amplify a fragment encoding the EGF-like domain.

EGF14:
TAGGATCCAAGAGGGACCCATGTCTTCGG (SEQ ID NO: 99)

EGF12:
TTCTCGAGGAGGCTCAGCCCATGACACCT (SEQ ID NO: 97)

(94° C./30 s, 65° C./30 s, 72° C./30 s: 30 cycles)

The obtained PCR product was then digested with BamHI and XhoI and was inserted downstream from the GST coding region of an *E. coli* GST fusion expression vector (pGEX-6P-1) that had been similarly digested with BamHI and XhoI, in order to construct an HB-EGF EGF-like domain/GST fusion protein expression vector (pGEX-HBEGF_EGFD).

9-1-2. Induction of the Expression of the Individual GST Fusion Proteins

The various *E. coli* expression vectors constructed as described above were transformed into *E. coli* BL21. The *E. coli* transformants were cultured on LB medium (1 mL each) and IPTG (final 1 mM) was added during the logarithmic growth phase to induce protein expression. The *E. coli* was recovered after 4 to 5 hours; a lysate was prepared by lysis in SDS sample buffer (0.5 mL); and 5 µL of the lysate was used for SDS-PAGE by a standard method, and then blotting to a PVDF membrane for Western blotting.

9-1-3. Analysis of the HE-39 Recognition Domain on the Mature HB-EGF Protein

The region of the mature HB-EGF protein recognized by the HE-39 antibody was investigated by Western blotting using the GST fusion proteins prepared as described above in which the individual regions of the mature HB-EGF protein (heparin-binding domain, EGF-like domain) were fused. The results of the Western blotting shown in FIG. 31*b* demonstrated that the HE-39 antibody recognized the EGF-like domain of the mature HB-EGF protein.

9-2. Analysis of the Epitope in the EGF Domain

Given that HE-39 recognized the EGF-like domain of the mature HB-EGF protein, the EGF-like domain was more finely partitioned, as shown in FIG. 32*a*, in an attempt to identify the epitope sequence.

9-2-1. Construction of the GST-EGFD5, GST-EGFD6, and GST-EGFD7 expression vectors

*E. coli* expression vectors for GST fusion proteins with EGF domain divided into three fragments (EGFD5, EGFD6, EGFD7) were prepared as follows.

In order to construct DNA fragments encoding each region (EGFD5, EGFD6, EGFD7), two oligomers were first designed for each region as follows.
Oligomers for EGFD5 Synthesis HEP9:
(SEQ ID NO: 100)
GAT CCA AGA GGG ACC CAT GTC TTC GGA AAT ACA AGG
ACT TCT GCA TCC ATG GAG AAT GCA AAT ATC HEP10:
(SEQ ID NO: 101)
TCG AGA TAT TTG CAT TCT CCA TGG ATG CAG AAG TCC
TTG TAT TTC CGA AGA CAT GGG TCC CTC TTG Oligomers for EGFD6 synthesis
HEP11:
(SEQ ID NO: 102)
GAT CCT GCA TCC ATG GAG AAT GCA AAT ATG TGA AGG
AGC TCC GGG CTC CCT CCT GCA TCT GCC ACC CGC HEP12:
(SEQ ID NO: 103)
TCG AGC GGG TGG CAG ATG CAG GAG GGA GCC CGG AGC
TCC TTC ACA TAT TTG CAT TCT CCA TGG ATG CAG Oligomers for EGFD7 synthesis
HEP13:
(SEQ ID NO: 104)
GAT CCG CTC CCT CCT GCA TCT GCC ACC CGG GTT ACC
ATG GAG AGA GGT GTC ATG GGC TGA GCC TCC HEP14:
(SEQ ID NO: 105)
TCG AGG AGG CTC AGC CCA TGA CAC CTC TCT CCA TGG
TAA CCC GGG TGG CAG ATG CAG GAG GGA GCG In each case, the two oligomers were combined and annealed by a standard method to prepare a double-stranded DNA fragment, and inserted downstream from the GST coding region of an *E. coli* GST fusion expression vector (pGEX-6P-1) that had been digested with BamHI and XhoI, to produce the individual constructs (pGEX-HBEGF_EGFD5, pGEX-HBEGF_EGFD6, pGEX-HBEGF_EGFD7).

9-2-2. Induction of Expression of Each Gst Fusion Protein

Each of the *E. coli* expression vectors constructed as described above was transformed into *E. coli* BL21. The *E. coli* transformant was cultured on LB medium (1 mL each) and IPTG (final 1 mM) was added during the logarithmic growth phase to induce protein expression. The *E. coli* was recovered after 4 to 5 hours; a lysate was prepared by lysis in SDS sample buffer (0.5 mL); and 5 µL of the lysate was used for SDS-PAGE by a standard method, and then blotting to a PVDF membrane for Western blotting.

9-2-3. Epitope Mapping for HE-39

The recognition sequence for the HE-39 antibody was investigated by Western blotting using the GST fusion proteins (GST-EGFD5, GST-EGFD6, GST-EGFD7) prepared as described above using the one of the three fragments of the EGF-like domain. The results of the Western blotting shown in FIG. 32*b* demonstrated that, because the HE-39 antibody bound to GST-EGFD7, the HE-39 antibody recognized the sequence [APSCICHPGYHGERCHGLSL] in the EGF-like domain Analysis of the ADCC Activity Mediated by the Anti-HB-EGF Antibodies 10-1. Analysis of the Binding Activity Exhibited by the Individual Antibodies on Membrane-Expressed HB-EGF The binding activity for membrane-expressed HB-EGF was compared, via FACS analysis, for the antibodies obtained so far. The particular antibody (10 µg/mL) was reacted for 1 hour at 4° C. with HB-EGF_Ba/F3 cells (Ba/F3 cells that overexpress HB-EGF), followed by staining with FITC-labeled anti-mouse IgG antibody (Beckman Coulter, PN IM0819). Binding by the particular antibody to the cell surface HB-EGF was analyzed by FACS (Becton, Dickinson and Company).

The binding activity for HB-EGF_Ba/F3 measured by FACS analysis for each antibody is represented graphically in FIG. 33*a*. The G-mean value (GEO-mean) on the vertical axis is a value obtained by converting the antibody-induced fluorescence intensity of the cells into numerical values. The results of the analysis showed that HC-15 was the antibody with the strongest binding activity to HB-EGF on the cell membrane, and that HE-39, HE-48, and HE-58 also had strong binding activities.

10-2. Analysis of the Antibody-Dependent Cellular Cytotoxicity (ADCC) of the Anti-HB-EGF Antibodies The ADCC activity on HB-EGF_Ba/F3 cells was analyzed using the chromium release method and the antibodies (HB- 10, HB-20, HB-22, HC-15, HE-39, HE-48, HE-58) that had exhibited binding activity to HB-EGF_Ba/F3 cells.

Chromium-51 was added to HB-EGF_Ba/F3 cells propagated in 96-well plates and cultivation was continued for several hours. The culture medium was removed; the cells were washed with culture medium; and fresh culture medium was then added. The antibody was added to give a final concentration of 10 μg/mL; effector cells (recombinant cells obtained by inducing the forced expression of the mouse Fc-gamma receptor (NM_010188) in NK-92 (ATCC, CRL-2407)) were also added to each well at approximately 5× or 10× with reference to the target cells; and the plates were allowed to stand for 4 hours at 37° C. in a 5% $CO_2$ incubator. After standing, the plates were centrifuged and a constant amount of supernatant was recovered from each well; the radioactivity was measured using a Wallac 1480 gamma counter; and the specific chromium release (%) was determined. According to the results, which are shown in the upper graph in FIG. 33b, HB-22, HC-15, HE-39, HE-48, and HE-58 in particular induced a very strong ADCC activity among the anti-HB-EGF monoclonal antibodies used in the test. These results are results that show that anti-tumor antibody therapy targeted to HB-EGF is very useful.

The specific chromium release rate was calculated using the following formula.

$$\text{specific chromium release (\%)} = (A-C) \times 100/(B-C)$$

where: A is the radioactivity in a particular well; B is the average value of the radioactivity released into the medium by cell lysis with Nonidet P-40 at a final concentration of 1%; and C is the average value of the radioactivity for the addition of only medium.

10-3. Measurement of the Complement-Dependent Cytotoxicity (CDC) of the Anti-HB-EGF Antibodies HB-EGF_Ba/F3 cells were recovered by centrifugal separation (1000 rpm, 5 minutes, 4° C.); the cell pellet was suspended in approximately 200 μL medium and 3.7 MBq chromium-51 (Code No. CJS4, Amersham Pharmacia Biotech); and cultured for 1 hour at 37° C. in a 5% $CO_2$ incubator. The cells were then washed three times with medium; the cell density was subsequently adjusted to $1 \times 10^4$/mL with medium; and 100 μL was added to each well in 96-well flat-bottom plates.

The anti-HB-EGF monoclonal antibody (HB-10, HB-20, HB-22, HC-15, HE-39, HE-48, HE-58) and the control mouse IgG2a antibody (Cat. No. 553453, BD Biosciences Pharmingen) were diluted with medium and then added at 50 μL per well. The antibody was adjusted to a final concentration of 10 μg/mL. Baby rabbit complement (Cat. No. CL3441, Cedarlane) was then added to each plate well so as to provide a concentration of 3% or 10%, followed by standing for 1.5 hours at 37° C. in a 5% $CO_2$ incubator. After standing, the plates were centrifuged (1000 rpm, 5 minutes, 4° C.); 100 μL supernatant was recovered from each well; and the radioactivity in the recovered supernatant was measured with a gamma counter (1480 WIZARD 3", Wallace).

According to the results as shown in the lower graph in FIG. 33b, HB-20, HB-22, HC-15, and HE-48 exhibited a CDC activity among the anti-HB-EGF monoclonal antibodies used in this test. On the other, the mouse IgG2a antibody used as a control did not exhibit CDC activity at the same concentration.

INDUSTRIAL APPLICABILITY

The antibody of the present invention and pharmaceutical compositions comprising the antibody of the present invention are useful for the treatment and diagnosis of cancer.

What is claimed is:

1. An isolated anti-HB-EGF antibody selected from the following (1) to (4):
   (1) an isolated antibody comprising a heavy chain variable region having the amino acid sequence of SEQ ID NO:26 as CDR1, the amino acid sequence of SEQ ID NO:28 as CDR2, and the amino acid sequence of SEQ ID NO:30 as CDR3 and comprising a light chain variable region having the amino acid sequence of SEQ ID NO:32 as CDR1, the amino acid sequence of SEQ ID NO:34 as CDR2, and the amino acid sequence of SEQ ID NO:36 as CDR3;
   (2) an isolated antibody comprising a heavy chain variable region having the amino acid sequence of SEQ ID NO:76 as CDR1, the amino acid sequence of SEQ ID NO:77 as CDR2, and the amino acid sequence of SEQ ID NO:78 as CDR3 and comprising a light chain variable region having the amino acid sequence of SEQ ID NO:79 as CDR1, the amino acid sequence of SEQ ID NO:80 as CDR2, and the amino acid sequence of SEQ ID NO:81 as CDR3;
   (3) an isolated antibody comprising a heavy chain variable region having the amino acid sequence of SEQ ID NO:76 as CDR1, the amino acid sequence of SEQ ID NO:77 as CDR2, and the amino acid sequence of SEQ ID NO:78 as CDR3 and comprising a light chain variable region having the amino acid sequence of SEQ ID NO:82 as CDR1, the amino acid sequence of SEQ ID NO:83 as CDR2, and the amino acid sequence of SEQ ID NO:84 as CDR36; and (4) an antibody that binds an epitope that is the same as the epitope bound by the antibody according to any of (1) to (3).

2. A pharmaceutical composition comprising the antibody according to claim 1.

3. A pharmaceutical composition comprising a cytotoxic substance attached to the antibody according to claim 1.

4. The pharmaceutical composition according to claim 2, which is a cell proliferation inhibitor.

5. The pharmaceutical composition according to claim 4, which is an anti-cancer agent.

6. The pharmaceutical composition according to claim 5, wherein the cancer is pancreatic cancer, liver cancer, esophageal cancer, melanoma, colorectal cancer, gastric cancer, ovarian cancer, uterine cervical cancer, breast cancer, bladder cancer, a brain tumor, or a hematological cancer.

7. The antibody according to claim 1, having an internalizing activity.

8. The antibody according to claim 7 to which a cytotoxic substance is attached.

9. The antibody according to claim 1, having an ADCC activity or a CDC activity.

10. The antibody according to claim 8, having an ADCC activity or a CDC activity.

* * * * *

SEQUENCE LISTING

```
<160> NUMBER OF SEQ ID NOS: 105

<210> SEQ ID NO 1
<211> LENGTH: 15
<212> TYPE: DNA
<213> ORGANISM: Mus musculus

<400> SEQUENCE: 1
agctactgga tgcac                                                      15

<210> SEQ ID NO 2
<211> LENGTH: 5
<212> TYPE: PRT
<213> ORGANISM: Mus musculus

<400> SEQUENCE: 2

Ser Tyr Trp Met His
1               5

<210> SEQ ID NO 3
<211> LENGTH: 51
<212> TYPE: DNA
<213> ORGANISM: Mus musculus

<400> SEQUENCE: 3
gagattaatc ctagcaacgg tcgtactaac tacaatgaga agttcaagag c              51

<210> SEQ ID NO 4
<211> LENGTH: 17
```

<212> TYPE: PRT
<213> ORGANISM: Mus musculus

<400> SEQUENCE: 4

Glu Ile Asn Pro Ser Asn Gly Arg Thr Asn Tyr Asn Glu Lys Phe Lys
1               5                   10                  15

Ser

<210> SEQ ID NO 5
<211> LENGTH: 15
<212> TYPE: DNA
<213> ORGANISM: Mus musculus

<400> SEQUENCE: 5
tccctctttg actac                                                     15

<210> SEQ ID NO 6
<211> LENGTH: 5
<212> TYPE: PRT
<213> ORGANISM: Mus musculus

<400> SEQUENCE: 6

Ser Leu Phe Asp Tyr
1               5

<210> SEQ ID NO 7
<211> LENGTH: 36
<212> TYPE: DNA
<213> ORGANISM: Mus musculus

<400> SEQUENCE: 7
agtgccagct caagtataag ttccaattac ttgcat                              36

<210> SEQ ID NO 8
<211> LENGTH: 12
<212> TYPE: PRT
<213> ORGANISM: Mus musculus

<400> SEQUENCE: 8

Ser Ala Ser Ser Ser Ile Ser Ser Asn Tyr Leu His
1               5                   10

<210> SEQ ID NO 9
<211> LENGTH: 21
<212> TYPE: DNA
<213> ORGANISM: Mus musculus

<400> SEQUENCE: 9
aggacatcca atctggcttc t                                              21

<210> SEQ ID NO 10
<211> LENGTH: 7
<212> TYPE: PRT
<213> ORGANISM: Mus musculus

<400> SEQUENCE: 10

Arg Thr Ser Asn Leu Ala Ser
1               5

<210> SEQ ID NO 11
<211> LENGTH: 27
<212> TYPE: DNA
<213> ORGANISM: Mus musculus

<400> SEQUENCE: 11
cagcagggta gtagtatacc attcacg                                        27

<210> SEQ ID NO 12
<211> LENGTH: 9
<212> TYPE: PRT
<213> ORGANISM: Mus musculus

<400> SEQUENCE: 12

Gln Gln Gly Ser Ser Ile Pro Phe Thr
1               5

<210> SEQ ID NO 13
<211> LENGTH: 15
<212> TYPE: DNA
<213> ORGANISM: Mus musculus

<400> SEQUENCE: 13
ggctatggta taaac                                                     15

<210> SEQ ID NO 14
<211> LENGTH: 5
<212> TYPE: PRT
<213> ORGANISM: Mus musculus

<400> SEQUENCE: 14

Gly Tyr Gly Ile Asn
1               5

<210> SEQ ID NO 15
<211> LENGTH: 48
<212> TYPE: DNA
<213> ORGANISM: Mus musculus

<400> SEQUENCE: 15
atgatctggg gtgatggaag cgcagactat aattcagctc tcaaatcc                 48

<210> SEQ ID NO 16
<211> LENGTH: 16
<212> TYPE: PRT
<213> ORGANISM: Mus musculus

<400> SEQUENCE: 16

Met Ile Trp Gly Asp Gly Ser Ala Asp Tyr Asn Ser Ala Leu Lys Ser
1               5                   10                  15

<210> SEQ ID NO 17
<211> LENGTH: 30
<212> TYPE: DNA
<213> ORGANISM: Mus musculus

<400> SEQUENCE: 17
ggggattact acggctacag gttttcttac                                     30

<210> SEQ ID NO 18
<211> LENGTH: 10
<212> TYPE: PRT
<213> ORGANISM: Mus musculus

<400> SEQUENCE: 18

Gly Asp Tyr Tyr Gly Tyr Arg Phe Ser Tyr
1               5                   10

```
<210> SEQ ID NO 19
<211> LENGTH: 51
<212> TYPE: DNA
<213> ORGANISM: Mus musculus

<400> SEQUENCE: 19
aagtccagtc aaagtgtttt atacagttca aatcagaaga acttcttggc c          51

<210> SEQ ID NO 20
<211> LENGTH: 17
<212> TYPE: PRT
<213> ORGANISM: Mus musculus

<400> SEQUENCE: 20

Lys Ser Ser Gln Ser Val Leu Tyr Ser Ser Asn Gln Lys Asn Phe Leu
1               5                   10                  15

Ala

<210> SEQ ID NO 21
<211> LENGTH: 21
<212> TYPE: DNA
<213> ORGANISM: Mus musculus

<400> SEQUENCE: 21
tgggcatcca ctagggaatc t                                            21

<210> SEQ ID NO 22
<211> LENGTH: 7
<212> TYPE: PRT
<213> ORGANISM: Mus musculus

<400> SEQUENCE: 22

Trp Ala Ser Thr Arg Glu Ser
1               5

<210> SEQ ID NO 23
<211> LENGTH: 24
<212> TYPE: DNA
<213> ORGANISM: Mus musculus

<400> SEQUENCE: 23
catcaatacc tctcctcgta tacg                                         24

<210> SEQ ID NO 24
<211> LENGTH: 8
<212> TYPE: PRT
<213> ORGANISM: Mus musculus

<400> SEQUENCE: 24

His Gln Tyr Leu Ser Ser Tyr Thr
1               5

<210> SEQ ID NO 25
<211> LENGTH: 15
<212> TYPE: DNA
<213> ORGANISM: Mus musculus

<400> SEQUENCE: 25
ggctactaca tgcac                                                   15

<210> SEQ ID NO 26
<211> LENGTH: 5
<212> TYPE: PRT
<213> ORGANISM: Mus musculus
```

```
<400> SEQUENCE: 26

Gly Tyr Tyr Met His
1               5

<210> SEQ ID NO 27
<211> LENGTH: 51
<212> TYPE: DNA
<213> ORGANISM: Mus musculus

<400> SEQUENCE: 27
gagattaatc ctagaactgg tattactacc tacaaccaga agttcaaggc c          51

<210> SEQ ID NO 28
<211> LENGTH: 17
<212> TYPE: PRT
<213> ORGANISM: Mus musculus

<400> SEQUENCE: 28

Glu Ile Asn Pro Arg Thr Gly Ile Thr Thr Tyr Asn Gln Lys Phe Lys
1               5                   10                  15

Ala

<210> SEQ ID NO 29
<211> LENGTH: 27
<212> TYPE: DNA
<213> ORGANISM: Mus musculus

<400> SEQUENCE: 29
gttggcagct cgggccctttt tacgtac                                     27

<210> SEQ ID NO 30
<211> LENGTH: 9
<212> TYPE: PRT
<213> ORGANISM: Mus musculus

<400> SEQUENCE: 30

Val Gly Ser Ser Gly Pro Phe Thr Tyr
1               5

<210> SEQ ID NO 31
<211> LENGTH: 51
<212> TYPE: DNA
<213> ORGANISM: Mus musculus

<400> SEQUENCE: 31
aagtccagtc agagtctgtt aaatagtaga aaccaaaaga actacttggc c          51

<210> SEQ ID NO 32
<211> LENGTH: 17
<212> TYPE: PRT
<213> ORGANISM: Mus musculus

<400> SEQUENCE: 32

Lys Ser Ser Gln Ser Leu Leu Asn Ser Arg Asn Gln Lys Asn Tyr Leu
1               5                   10                  15

Ala

<210> SEQ ID NO 33
<211> LENGTH: 21
<212> TYPE: DNA
<213> ORGANISM: Mus musculus
```

```
<400> SEQUENCE: 33
ggggcatcca ctagggaatc t                                                    21

<210> SEQ ID NO 34
<211> LENGTH: 7
<212> TYPE: PRT
<213> ORGANISM: Mus musculus

<400> SEQUENCE: 34

Gly Ala Ser Thr Arg Glu Ser
1               5

<210> SEQ ID NO 35
<211> LENGTH: 27
<212> TYPE: DNA
<213> ORGANISM: Mus musculus

<400> SEQUENCE: 35
cagaatgatt atagttatcc attcacg                                              27

<210> SEQ ID NO 36
<211> LENGTH: 9
<212> TYPE: PRT
<213> ORGANISM: Mus musculus

<400> SEQUENCE: 36

Gln Asn Asp Tyr Ser Tyr Pro Phe Thr
1               5

<210> SEQ ID NO 37
<211> LENGTH: 399
<212> TYPE: DNA
<213> ORGANISM: Mus musculus

<400> SEQUENCE: 37
atgggatgga gctatatcat cctcttttg gtagcaacag ctacagatgt ccactcccag           60
gtccaactgc agcagcctgg ggctgaactg gtgaagcctg ggcttcagt gaagctgtcc         120 tgcaaggctt ctggctacac cttcaccagc tactggatgc actgggtgaa gcagaggcct        180
ggacaaggcc ttgagtggat tggagagatt aatcctagca acggtcgtac taactacaat        240
gagaagttca agagcaaggc cacactgact gtagacaaat cctccagcac agcctacatg        300
caactcagca gcctgacatc tgaggactct gcggtctatt actgtgtatg gtccctcttt        360
gactactggg gccaaggcac cactctcaca gtctcctca                               399

<210> SEQ ID NO 38
<211> LENGTH: 133
<212> TYPE: PRT
<213> ORGANISM: Mus musculus

<400> SEQUENCE: 38

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asn Pro Ser Asn Gly Arg Thr Asn Tyr Asn
```

```
                65                  70                  75                  80
        Glu Lys Phe Lys Ser Lys Ala Thr Leu Thr Val Asp Lys Ser Ser
                            85                  90                  95

Thr Ala Tyr Met Gln Leu Ser Ser Leu Thr Ser Glu Asp Ser Ala Val
                        100                 105                 110

Tyr Tyr Cys Val Trp Ser Leu Phe Asp Tyr Trp Gly Gln Gly Thr Thr
                    115                 120                 125

Leu Thr Val Ser Ser
                130

<210> SEQ ID NO 39
        <211> LENGTH: 378
        <212> TYPE: DNA
        <213> ORGANISM: Mus musculus

<400> SEQUENCE: 39
atgcagatta tcagcttgct gctaatcagt gtcacagtca tagtgtctaa tggagaaatt      60
gtgctcaccc agtctccaac caccatggct gcatctcccg gggagaagat cactatcacc     120
tgcagtgcca gctcaagtat aagttccaat tacttgcatt ggtatcagca gaagccagga     180
ttctccccta aactcttgat ttataggaca tccaatctgg cttctggagt cccagctcgc     240
ttcagtggca gtgggtctgg gacctcttac tctctcacaa ttggcaccat ggaggctgaa     300
gatgttgcca cttactactg ccagcagggt agtagtatac cattcacgtt cggctcgggg     360
acaaagttgg aaataaaa                                                  378

<210> SEQ ID NO 40
        <211> LENGTH: 126
        <212> TYPE: PRT
        <213> ORGANISM: Mus musculus

<400> SEQUENCE: 40

Met Gln Ile Ile Ser Leu Leu Leu Ile Ser Val Thr Val Ile Val Ser
        1               5                   10                  15

Asn Gly Glu Ile Val Leu Thr Gln Ser Pro Thr Thr Met Ala Ala Ser
                    20                  25                  30

Pro Gly Glu Lys Ile Thr Ile Thr Cys Ser Ala Ser Ser Ile Ser
                35                  40                  45

Ser Asn Tyr Leu His Trp Tyr Gln Gln Lys Pro Gly Phe Ser Pro Lys
            50                  55                  60

Leu Leu Ile Tyr Arg Thr Ser Asn Leu Ala Ser Gly Val Pro Ala Arg
        65                  70                  75                  80

Phe Ser Gly Ser Gly Ser Gly Thr Ser Tyr Ser Leu Thr Ile Gly Thr
                        85                  90                  95

Met Glu Ala Glu Asp Val Ala Thr Tyr Tyr Cys Gln Gln Gly Ser Ser
                    100                 105                 110

Ile Pro Phe Thr Phe Gly Ser Gly Thr Lys Leu Glu Ile Lys
                115                 120                 125

<210> SEQ ID NO 41
        <211> LENGTH: 411
        <212> TYPE: DNA
        <213> ORGANISM: Mus musculus

<400> SEQUENCE: 41
atggctgtcc tggcattact cttctgcctg gtaacattcc caagctgtat ccttttccag      60
gtgcagctga aggagtcagg acctggcctg gtggcgccct cacagagcct gtccatcaca     120
```

```
tgcaccgtct cagggttctc attaaccggc tatggtataa actgggttcg ccagcctcca    180
ggaaagggtc tggagtggct gggaatgatc tggggtgatg aagcgcaga ctataattca    240 gctctcaaat ccagactgag catccgcaag acaactcca agagccaagt tttcttagaa    300
atgaacagtc tgcaaactga tgacacagcc aggtactact gtgccagagg ggattactac    360
ggctacaggt tttcttactg gggccaaggg actctggtca ctgtctctgc a            411
```

<210> SEQ ID NO 42
<211> LENGTH: 137
<212> TYPE: PRT
<213> ORGANISM: Mus musculus

<400> SEQUENCE: 42

```
Met Ala Val Leu Ala Leu Leu Phe Cys Leu Val Thr Phe Pro Ser Cys
1               5                   10                  15

Ile Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Gly Tyr Gly Ile Asn Trp Val Arg Gln Pro Pro Lys Gly Leu
    50                  55                  60

Glu Trp Leu Gly Met Ile Trp Gly Asp Gly Ser Ala Asp Tyr Asn Ser
65                  70                  75                  80

Ala Leu Lys Ser Arg Leu Ser Ile Arg Lys Asp Asn Ser Lys Ser Gln
                85                  90                  95

Val Phe Leu Glu Met Asn Ser Leu Gln Thr Asp Asp Thr Ala Arg Tyr
            100                 105                 110

Tyr Cys Ala Arg Gly Asp Tyr Tyr Gly Tyr Arg Phe Ser Tyr Trp Gly
        115                 120                 125

Gln Gly Thr Leu Val Thr Val Ser Ala
    130                 135
```

<210> SEQ ID NO 43
<211> LENGTH: 396
<212> TYPE: DNA
<213> ORGANISM: Mus musculus

<400> SEQUENCE: 43

```
atggaatcac agactcaggt cttcctctcc ctgctgctct ggtatctgg taccttggg     60 aacattatgc tgacacagtc gccatcatct ctggctgtgt ctgcaggaga aaaggtcact    120
atgagctgta agtccagtca agtgttttta tacagttcaa atcagaagaa cttcttggcc    180
tggtaccagc agaaaccagg gcagtctcct aaactgctga tctactgggc atccactagg    240
gaatctggtg tccctgatcg cttcgcaggc agtggatctg ggacagattt tactcttacc    300
atcagcagtg tacaaactga agacctggca gtttattact gtcatcaata cctctcctcg    360
tatacgttcg gaggggggac caagctggaa ataaaa                              396
```

<210> SEQ ID NO 44
<211> LENGTH: 132
<212> TYPE: PRT
<213> ORGANISM: Mus musculus

<400> SEQUENCE: 44

```
Met Glu Ser Gln Thr Gln Val Phe Leu Ser Leu Leu Leu Trp Val Ser
1               5                   10                  15
```

Gly Thr Phe Gly Asn Ile Met Leu Thr Gln Ser Pro Ser Ser Leu Ala
            20                  25                  30

Val Ser Ala Gly Glu Lys Val Thr Met Ser Cys Lys Ser Ser Gln Ser
        35                  40                  45

Val Leu Tyr Ser Ser Asn Gln Lys Asn Phe Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Ala Gly Ser Gly Ser Gly Thr Asp
                85                  90                  95

Phe Thr Leu Thr Ile Ser Ser Val Gln Thr Glu Asp Leu Ala Val Tyr
            100                 105                 110

Tyr Cys His Gln Tyr Leu Ser Ser Tyr Thr Phe Gly Gly Gly Thr Lys
        115                 120                 125

Leu Glu Ile Lys
    130

<210> SEQ ID NO 45
<211> LENGTH: 411
<212> TYPE: DNA
<213> ORGANISM: Mus musculus

<400> SEQUENCE: 45
atgggatgga actggatctt tattttaatc ctgtcagtaa ctacaggtgt ccactctgag      60
gtccagctgc agcagtctgg acctgagctg gtgaagcctg ggcttcagt gaagatatcc     120 tgcaaggctt ctggttactc attcactggc tactacatgc actgggtgaa gcaaagtcct    180
gaaaagagac ttgagtggat tggagagatt aatcctagaa ctggtattac tacctacaac    240
cagaagttca aggccaaggc cacattgact gtagacaaat cctccagcac agcctacatg    300
cagctcaaga gcctgacatc tgaggactct gcagtctatt actgtgcaag agttggcagc    360
tcgggccctt ttacgtactg gggccaaggg actctggtca ctgtctctgc a             411

<210> SEQ ID NO 46
<211> LENGTH: 137
<212> TYPE: PRT
<213> ORGANISM: Mus musculus

<400> SEQUENCE: 46

Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Tyr Met His Trp Val Lys Gln Ser Pro Glu Lys Arg Leu
    50                  55                  60

Glu Trp Ile Gly Glu Ile Asn Pro Arg Thr Gly Ile Thr Thr Tyr Asn
65                  70                  75                  80

Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Val Gly Ser Ser Gly Pro Phe Thr Tyr Trp Gly
        115                 120                 125

Gln Gly Thr Leu Val Thr Val Ser Ala

<210> SEQ ID NO 47
<211> LENGTH: 399
<212> TYPE: DNA
<213> ORGANISM: Mus musculus

<400> SEQUENCE: 47

```
atggaatcac agactcaggt cctcatgtcc ctgctgctct gggtatctgg tacctgtggg      60
gacattgtga tgacacagtc tccatcctcc ctgagtgtgt cagcaggaga taaggtcact     120
atgagctgca gtccagtca gagtctgtta aatagtagaa accaaaagaa ctacttggcc      180
tggtaccagc agaaaccatg gcagcctcct aaattgctga tctacggggc atccactagg     240
gaatctgggg tccctgatcg cttcacaggc agtggatctg gaacagattt cactctcacc     300
atcagcagtg tgcaggctga agacctggca gtttattact gtcagaatga ttatagttat     360
ccattcacgt tcggcacggg gacaaaattg gaaataaaa                            399
```

<210> SEQ ID NO 48
<211> LENGTH: 133
<212> TYPE: PRT
<213> ORGANISM: Mus musculus

<400> SEQUENCE: 48

Met Glu Ser Gln Thr Gln Val Leu Met Ser Leu Leu Leu Trp Val Ser
1               5                   10                  15

Gly Thr Cys Gly Asp Ile Val Met Thr Gln Ser Pro Ser Ser Leu Ser
                20                  25                  30

Val Ser Ala Gly Asp Lys Val Thr Met Ser Cys Lys Ser Ser Gln Ser
            35                  40                  45

Leu Leu Asn Ser Arg Asn Gln Lys Asn Tyr Leu Ala Trp Tyr Gln Gln
        50                  55                  60

Lys Pro Trp Gln Pro Pro Lys Leu Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
                100                 105                 110

Tyr Cys Gln Asn Asp Tyr Ser Tyr Pro Phe Thr Phe Gly Thr Gly Thr
            115                 120                 125

Lys Leu Glu Ile Lys
        130

<210> SEQ ID NO 49
<211> LENGTH: 627
<212> TYPE: DNA
<213> ORGANISM: homo sapiens

<400> SEQUENCE: 49

```
atgaagctgc tgccgtcggt ggtgctgaag ctctttctgg ctgcagttct ctcggcactg      60
gtgactggcg agagcctgga gcggcttcgg agagggctag ctgctggaac cagcaacccg     120
gaccctccca ctgtatccac ggaccagctg ctaccccctag gaggcggccg ggaccggaaa    180
gtccgtgact tgcaagaggc agatctggac cttttgagag tcactttatc ctccaagcca     240
caagcactgg ccacaccaaa caaggaggag cacgggaaaa gaagaagaa aggcaagggg      300
ctagggaaga gagggaccc atgtcttcgg aaatacaagg acttctgcat ccatggagaa     360
```

```
tgcaaatatg tgaaggagct ccgggctccc tcctgcatct gccacccggg ttaccatgga    420
gagaggtgtc atgggctgag cctcccagtg gaaaatcgct tatataccta tgaccacaca    480
accatcctgg ccgtggtggc tgtggtgctg tcatctgtct gtctgctggt catcgtgggg    540
cttctcatgt ttaggtacca taggagagga ggttatgatg tggaaaatga agagaaagtg    600
aagttgggca tgactaattc ccactga                                        627
```

<210> SEQ ID NO 50
<211> LENGTH: 208
<212> TYPE: PRT
<213> ORGANISM: homo sapiens

<400> SEQUENCE: 50

```
Met Lys Leu Leu Pro Ser Val Val Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
            35                  40                  45

Gln Leu Leu Pro Leu Gly Gly Gly Arg Asp Arg Lys Val Arg Asp Leu
 50                  55                  60

Gln Glu Ala Asp Leu Asp Leu Arg Val Thr Leu Ser Ser Lys Pro
 65              70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
                100                 105                 110

Lys Asp Phe Cys Ile His Gly Glu Cys Lys Tyr Val Lys Glu Leu Arg
            115                 120                 125

Ala Pro Ser Cys Ile Cys His Pro Gly Tyr His Gly Glu Arg Cys His
 130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
            195                 200                 205
```

<210> SEQ ID NO 51
<211> LENGTH: 21
<212> TYPE: DNA
<213> ORGANISM: Artificial
<220> FEATURE:
<223> OTHER INFORMATION: PCR primer

<400> SEQUENCE: 51

```
atgaagctgc tgccgtcggt g                                              21
```

<210> SEQ ID NO 52
<211> LENGTH: 22
<212> TYPE: DNA
<213> ORGANISM: Artificial
<220> FEATURE:
<223> OTHER INFORMATION: PCR primer

<400> SEQUENCE: 52
tcagtgggaa ttagtcatgc cc                                      22

<210> SEQ ID NO 53
<211> LENGTH: 34
<212> TYPE: DNA
<213> ORGANISM: Artificial
<220> FEATURE:
<223> OTHER INFORMATION: PCR primer

<400> SEQUENCE: 53
taagtcgacc accatgaagc tgctgccgtc ggtg                         34

<210> SEQ ID NO 54
<211> LENGTH: 60
<212> TYPE: DNA
<213> ORGANISM: Artificial
<220> FEATURE:
<223> OTHER INFORMATION: PCR primer

<400> SEQUENCE: 54
tttgcggccg ctcacttgtc atcgtcgtcc ttgtagtcgt gggaattagt catgcccaac    60

<210> SEQ ID NO 55
<211> LENGTH: 30
<212> TYPE: DNA
<213> ORGANISM: Artificial
<220> FEATURE:
<223> OTHER INFORMATION: PCR primer

<400> SEQUENCE: 55
aaagaattcc accatgaagc tgctgccgtc                              30

<210> SEQ ID NO 56
<211> LENGTH: 40
<212> TYPE: DNA
<213> ORGANISM: Artificial
<220> FEATURE:
<223> OTHER INFORMATION: PCR primer

<400> SEQUENCE: 56
tatcggtccg cgaggttcga ggctcagccc atgacacctc                   40

<210> SEQ ID NO 57
<211> LENGTH: 38
<212> TYPE: DNA
<213> ORGANISM: Artificial
<220> FEATURE:
<223> OTHER INFORMATION: PCR primer

<400> SEQUENCE: 57
cgattttcca ctgtgctgct cagcccatga cacctctc                     38

<210> SEQ ID NO 58
<211> LENGTH: 39
<212> TYPE: DNA
<213> ORGANISM: Artificial
<220> FEATURE:
<223> OTHER INFORMATION: PCR primer

<400> SEQUENCE: 58
tgggctgagc agcacagtgg aaaatcgctt atataccta                    39

<210> SEQ ID NO 59
<211> LENGTH: 3633
<212> TYPE: DNA
<213> ORGANISM: homo sapiens

<400> SEQUENCE: 59

```
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca tttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tgggcagctg ccaaaagtgt gatccaagct gtcccaatgg agctgctgg     600
ggtgcaggag aggagaactg ccagaaactg accaaaatca tctgtgccca gcagtgctcc     660
gggcgctgcc gtggcaagtc ccccagtgac tgctgccaca accagtgtgc tgcaggctgc     720
acaggccccc gggagagcga ctgcctggtc tgccgcaaat ccgagacga agccacgtgc     780
aaggacacct gcccccccact catgctctac aaccccacca cgtaccagat ggatgtgaac     840
cccgagggca aatacagctt tggtgccacc tgcgtgaaga agtgtcccg taattatgtg     900
gtgacagatc acggctcgtg cgtccgagcc tgtggggccg acagctatga gatggaggaa     960
gacgcgtcc gcaagtgtaa gaagtgcgaa gggccttgcc gcaaagtgtg taacggaata    1020
ggtattggtg aatttaaaga ctcactctcc ataaatgcta cgaatattaa acacttcaaa    1080
aactgcacct ccatcagtgg cgatctccac atcctgccgg tggcatttag gggtgactcc    1140
ttcacacata ctcctcctct ggatccacag gaactggata ttctgaaaac cgtaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg gaaaaaactg    1440
tttgggaccct ccggtcagaa aaccaaaatt ataagcaaca gaggtgaaaa cagctgcaag    1500
gccacaggcc aggtctgcca tgccttgtgc tcccccgagg ctgctgggg cccggagccc    1560
agggactgcg tctcttgccg gaatgtcagc cgaggcaggg aatgcgtgga caagtgcaac    1620
cttctggagg tgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggccccac tgcgtcaaga cctgcccggc aggagtcatg    1800
ggagaaaaca caccctggt ctggaagtac gcagacgccg ccatgtgtg ccacctgtgc    1860
catccaaact gcacctacgg atgcactggg ccaggtcttg aaggctgtcc aacgaatggg    1920
cctaagatcc cgtccatcgc cactgggatg gtgggggccc tcctcttgct gctggtggtg    1980
gccctgggga tcggcctctt catgcgaagg cgccacatcg ttcggaagcg cacgctgcgg    2040
aggctgctgc aggagaggga gcttgtgcag cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaat    2220
cccgtcgcta tcaaggaatt aagagaagca acatctccga aagccaacaa ggaaatcctc    2280
```

| | | | | |
|---|---|---|---|---|
| gatgaagcct acgtgatggc cagcgtggac aaccccacg tgtgccgcct gctgggcatc | 2340 |
| tgcctcacct ccaccgtgca gctcatcacg cagctcatgc ccttcggctg cctcctggac | 2400 |
| tatgtccggg aacacaaaga caatattggc tcccagtacc tgctcaactg tgtgtgcag | 2460 |
| atcgcaaagg gcatgaacta cttggaggac cgtcgcttgg tgcaccgcga cctggcagcc | 2520 |
| aggaacgtac tggtgaaaac accgcagcat gtcaagatca cagattttgg gctggccaaa | 2580 |
| ctgctgggtg cggaagagaa agaataccat gcagaaggag gcaaagtgcc tatcaagtgg | 2640 |
| atggcattgg aatcaattt acacagaatc tatacccacc agagtgatgt ctggagctac | 2700 |
| ggggtgaccg tttgggagtt gatgaccttt ggatccaagc catatgacgg aatccctgcc | 2760 |
| agcgagatct cctccatcct ggagaaagga gaacgcctcc ctcagccacc catatgtacc | 2820 |
| atcgatgtct acatgatcat ggtcaagtgc tggatgatag acgcagatag tcgcccaaag | 2880 |
| ttccgtgagt tgatcatcga attctccaaa atggcccgag accccagcg ctaccttgtc | 2940 |
| attcagggg atgaaagaat gcatttgcca agtcctacag actccaactt ctaccgtgcc | 3000 |
| ctgatggatg aagaagacat ggacgacgtg gtggatgccg acgagtacct catcccacag | 3060 |
| cagggcttct tcagcagccc ctccacgtca cggactcccc tcctgagctc tctgagtgca | 3120 |
| accagcaaca attccaccgt ggcttgcatt gatagaaatg ggctgcaaag ctgtcccatc | 3180 |
| aaggaagaca gcttcttgca gcgatacagc tcagacccca caggcgccctt gactgaggac | 3240 |
| agcatagacg acaccttcct cccagtgcct gaatacataa accagtccgt tcccaaaagg | 3300 |
| cccgctggct ctgtgcagaa tcctgtctat cacaatcagc ctctgaaccc cgcgcccagc | 3360 |
| agagacccac actaccagga ccccacagc actgcagtgg caaccccga gtatctcaac | 3420 |
| actgtccagc ccacctgtgt caacagcaca ttcgacagcc ctgcccactg ggcccagaaa | 3480 |
| ggcagccacc aaattagcct ggacaaccct gactaccagc aggacttctt tcccaaggaa | 3540 |
| gccaagccaa atggcatctt taagggctcc acagctgaaa atgcagaata cctaagggtc | 3600 |
| gcgccacaaa gcagtgaatt tattggagca tga | 3633 |

<210> SEQ ID NO 60
<211> LENGTH: 1210
<212> TYPE: PRT
<213> ORGANISM: homo sapiens

<400> SEQUENCE: 60

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu

```
            130                 135                 140
His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560
```

```
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
```

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 61
<211> LENGTH: 20
<212> TYPE: DNA
<213> ORGANISM: Artificial
<220> FEATURE:
<223> OTHER INFORMATION: PCR primer

<400> SEQUENCE: 61
atgcgaccct ccgggacggc                                          20

<210> SEQ ID NO 62
<211> LENGTH: 21
<212> TYPE: DNA
<213> ORGANISM: Artificial
<220> FEATURE:
<223> OTHER INFORMATION: PCR primer

<400> SEQUENCE: 62
cagtggcgat ggacgggatc t                                        21

<210> SEQ ID NO 63
<211> LENGTH: 34
<212> TYPE: DNA
<213> ORGANISM: Artificial
<220> FEATURE:
<223> OTHER INFORMATION: PCR primer

<400> SEQUENCE: 63
ttgcggccgc caccatgcga ccctccggga cggc                         34

<210> SEQ ID NO 64
<211> LENGTH: 61
<212> TYPE: DNA
<213> ORGANISM: Artificial
<220> FEATURE:
<223> OTHER INFORMATION: PCR primer

<400> SEQUENCE: 64
accagatctc caggaaaatg tttaagtcag atggatcgga cgggatctta ggcccattcg    60
t                                                                    61

<210> SEQ ID NO 65
<211> LENGTH: 2514
<212> TYPE: DNA
<213> ORGANISM: Mus musculus

<400> SEQUENCE: 65
atggtagggc tgggagcctg caccctgact ggagttaccc tgatcttctt gctactcccc     60
agaagtctgg agagctgtgg acacatcgag atttcacccc ctgttgtccg cctgggggac    120
cctgtcctgg cctcttgcac catcagccca aactgcagca aactggacca acaggcaaag    180
atcttatgga gactgcaaga tgagcccatc aacctgggg acagacagca tcatctgcct    240
gatgggaccc aagagtccct catcactctg cctcacttga actacaccca ggccttcctc    300
ttctgcttag tgccatggga agacagcgtc caactcctgg atcaagctga gcttcacgca    360
ggctatcccc ctgccagccc ctcaaaccta tcctgcctca tgcacctcac caccaacagc    420
ctggtctgcc agtgggagcc aggtcctgag acccacctgc ccaccagctt catcctaaag    480
agcttcagga gccgcgccga ctgtcagtac caaggggaca ccatcccgga ttgtgtggca    540
aagaagaggc agaacaactg ctccatcccc cgaaaaaact tgctcctgta ccagtatatg    600
gccatctggg tgcaagcaga gaatatgcta gggtccagcg agtccccaaa gctgtgcctc    660
gaccccatgg atgttgtgaa attggagcct cccatgctgc aggccctgga cattggcccc    720
gatgtagtct ctcaccagcc tggctgcctg tggctgagct ggaagccatg gaagcccagt    780
gagtacatgg aacaggagtg tgaacttcgc taccagccac agctcaaagg agccaactgg    840
actctggtgt ccacctgcc ttccagcaag gaccagtttg agctctgcgg gctccatcag    900
gccccagtct acacccctaca gatgcgatgc attcgctcat ctctgcctgg attctggagc    960
ccctggagcc ccggcctgca gctgaggcct accatgaagg cccccaccat cagactggac   1020
acgtggtgtc agaagaagca actagatcca gggacagtga gtgtgcagct gttctggaag   1080
ccaacgcccc tgcaggaaga cagtggacag atccagggct acctgctgtc ctggaattcc   1140
ccagatcatc aagggcagga catacacctt gcaacacca cgcagctcag ctgtatcttc   1200
ctcctgcccct cagaggccca gaacgtgacc cttgtggcct acaacaaagc agggacctct   1260
tcacctacta cagtggttt cctggagaac gaaggtccag ctgtgaccgg actccatgcc   1320
atggcccaag accttaacac catctgggta gactgggaag cccccagcct tctgcctcag   1380
ggctatctca ttgagtggga aatgagttct cccagctaca ataacagcta taagtcctgg   1440
atgatagaac taacgggaa catcactgga attctgttaa aggacaacat aaatcccttt   1500
cagctctaca gaattacagt ggctcccctg tacccaggca tcgtgggacc ccctgtaaat   1560

-continued

```
gtctacacct tcgctggaga gagagctcct cctcatgctc cagcgctgca tctaaagcat    1620
gttggcacaa cctgggcaca gctggagtgg gtacctgagg cccctaggct ggggatgata    1680
cccctcaccc actacaccat cttctgggcc gatgctgggg accactcctt ctccgtcacc    1740
ctaaacatct ccctccatga ctttgtcctg aagcacctgg agcccgccag tttgtatcat    1800
gtctacctca tggccaccag tcgagcaggg tccaccaata gtacaggcct taccctgagg    1860
accctagatc catctgactt aaacattttc ctgggcatac tttgcttagt actcttgtcc    1920
actacctgtg tagtgacctg gctctgctgc aaacgcagag gaaagacttc cttctggtca    1980
gatgtgccag acccagccca cagtagcctg agctcctggt tgcccaccat catgacagag    2040
gaaaccttcc agttacccag cttctgggac tccagcgtgc catcaatcac caagatcact    2100
gaactggagg aagacaagaa accgacccac tgggattccg aaagctctgg gaatggtagc    2160
cttccagccc tggttcaggc ctatgtgctc caaggagatc aagagaaat ttccaaccag    2220 tcccagcctc cctctcgcac tggtgaccag gtcctctatg gtcaggtgct tgagagcccc    2280
accagcccag gagtaatgca gtacattcgc tctgactcca ctcagcccct cttgggggc    2340 cccacccta gccctaaatc ttatgaaaac atctggttcc attcaagacc ccaggagacc    2400
tttgtgcccc aacctccaaa ccaggaagat gactgtgtct ttgggcctcc atttgatttt    2460
cccctctttc aggggctcca ggtccatgga gttgaagaac aagggggttt ctag         2514
```

```
<210> SEQ ID NO 66
<211> LENGTH: 837
<212> TYPE: PRT
<213> ORGANISM: Mus musculus

<400> SEQUENCE: 66
```

Met Val Gly Leu Gly Ala Cys Thr Leu Thr Gly Val Thr Leu Ile Phe
1               5                   10                  15

Leu Leu Leu Pro Arg Ser Leu Glu Ser Cys Gly His Ile Glu Ile Ser
            20                  25                  30

Pro Pro Val Val Arg Leu Gly Asp Pro Val Leu Ala Ser Cys Thr Ile
        35                  40                  45

Ser Pro Asn Cys Ser Lys Leu Asp Gln Gln Ala Lys Ile Leu Trp Arg
    50                  55                  60

Leu Gln Asp Glu Pro Ile Gln Pro Gly Asp Arg Gln His His Leu Pro
65                  70                  75                  80

Asp Gly Thr Gln Glu Ser Leu Ile Thr Leu Pro His Leu Asn Tyr Thr
                85                  90                  95

Gln Ala Phe Leu Phe Cys Leu Val Pro Trp Glu Asp Ser Val Gln Leu
            100                 105                 110

Leu Asp Gln Ala Glu Leu His Ala Gly Tyr Pro Pro Ala Ser Pro Ser
        115                 120                 125

Asn Leu Ser Cys Leu Met His Leu Thr Thr Asn Ser Leu Val Cys Gln
    130                 135                 140

Trp Glu Pro Gly Pro Glu Thr His Leu Pro Thr Ser Phe Ile Leu Lys
145                 150                 155                 160

Ser Phe Arg Ser Arg Ala Asp Cys Gln Tyr Gln Gly Asp Thr Ile Pro
                165                 170                 175

Asp Cys Val Ala Lys Lys Arg Gln Asn Asn Cys Ser Ile Pro Arg Lys
            180                 185                 190

Asn Leu Leu Leu Tyr Gln Tyr Met Ala Ile Trp Val Gln Ala Glu Asn
        195                 200                 205

```
Met Leu Gly Ser Ser Glu Ser Pro Lys Leu Cys Leu Asp Pro Met Asp
    210                 215                 220
Val Val Lys Leu Glu Pro Pro Met Leu Gln Ala Leu Asp Ile Gly Pro
225                 230                 235                 240
Asp Val Val Ser His Gln Pro Gly Cys Leu Trp Leu Ser Trp Lys Pro
                245                 250                 255
Trp Lys Pro Ser Glu Tyr Met Glu Gln Glu Cys Glu Leu Arg Tyr Gln
            260                 265                 270
Pro Gln Leu Lys Gly Ala Asn Trp Thr Leu Val Phe His Leu Pro Ser
        275                 280                 285
Ser Lys Asp Gln Phe Glu Leu Cys Gly Leu His Gln Ala Pro Val Tyr
    290                 295                 300
Thr Leu Gln Met Arg Cys Ile Arg Ser Ser Leu Pro Gly Phe Trp Ser
305                 310                 315                 320
Pro Trp Ser Pro Gly Leu Gln Leu Arg Pro Thr Met Lys Ala Pro Thr
                325                 330                 335
Ile Arg Leu Asp Thr Trp Cys Gln Lys Lys Gln Leu Asp Pro Gly Thr
            340                 345                 350
Val Ser Val Gln Leu Phe Trp Lys Pro Thr Pro Leu Gln Glu Asp Ser
        355                 360                 365
Gly Gln Ile Gln Gly Tyr Leu Leu Ser Trp Asn Ser Pro Asp His Gln
    370                 375                 380
Gly Gln Asp Ile His Leu Cys Asn Thr Thr Gln Leu Ser Cys Ile Phe
385                 390                 395                 400
Leu Leu Pro Ser Glu Ala Gln Asn Val Thr Leu Val Ala Tyr Asn Lys
                405                 410                 415
Ala Gly Thr Ser Ser Pro Thr Thr Val Val Phe Leu Glu Asn Glu Gly
            420                 425                 430
Pro Ala Val Thr Gly Leu His Ala Met Ala Gln Asp Leu Asn Thr Ile
        435                 440                 445
Trp Val Asp Trp Glu Ala Pro Ser Leu Leu Pro Gln Gly Tyr Leu Ile
    450                 455                 460
Glu Trp Glu Met Ser Ser Pro Ser Tyr Asn Asn Ser Tyr Lys Ser Trp
465                 470                 475                 480
Met Ile Glu Pro Asn Gly Asn Ile Thr Gly Ile Leu Leu Lys Asp Asn
                485                 490                 495
Ile Asn Pro Phe Gln Leu Tyr Arg Ile Thr Val Ala Pro Leu Tyr Pro
            500                 505                 510
Gly Ile Val Gly Pro Pro Val Asn Val Tyr Thr Phe Ala Gly Glu Arg
        515                 520                 525
Ala Pro Pro His Ala Pro Ala Leu His Leu Lys His Val Gly Thr Thr
    530                 535                 540
Trp Ala Gln Leu Glu Trp Val Pro Glu Ala Pro Arg Leu Gly Met Ile
545                 550                 555                 560
Pro Leu Thr His Tyr Thr Ile Phe Trp Ala Asp Ala Gly Asp His Ser
                565                 570                 575
Phe Ser Val Thr Leu Asn Ile Ser Leu His Asp Phe Val Leu Lys His
            580                 585                 590
Leu Glu Pro Ala Ser Leu Tyr His Val Tyr Leu Met Ala Thr Ser Arg
        595                 600                 605
Ala Gly Ser Thr Asn Ser Thr Gly Leu Thr Leu Arg Thr Leu Asp Pro
    610                 615                 620
Ser Asp Leu Asn Ile Phe Leu Gly Ile Leu Cys Leu Val Leu Leu Ser
```

```
                625                630                635                640
            Thr Thr Cys Val Val Thr Trp Leu Cys Cys Lys Arg Arg Gly Lys Thr
                            645                650                655
            Ser Phe Trp Ser Asp Val Pro Asp Pro Ala His Ser Ser Leu Ser Ser
                            660                665                670
            Trp Leu Pro Thr Ile Met Thr Glu Glu Thr Phe Gln Leu Pro Ser Phe
                            675                680                685
            Trp Asp Ser Ser Val Pro Ser Ile Thr Lys Ile Thr Glu Leu Glu Glu
                            690                695                700
            Asp Lys Lys Pro Thr His Trp Asp Ser Glu Ser Ser Gly Asn Gly Ser
            705                710                715                720
            Leu Pro Ala Leu Val Gln Ala Tyr Val Leu Gln Gly Asp Pro Arg Glu
                            725                730                735
            Ile Ser Asn Gln Ser Gln Pro Pro Ser Arg Thr Gly Asp Gln Val Leu
                            740                745                750
            Tyr Gly Gln Val Leu Glu Ser Pro Thr Ser Pro Gly Val Met Gln Tyr
                            755                760                765
            Ile Arg Ser Asp Ser Thr Gln Pro Leu Leu Gly Gly Pro Thr Pro Ser
                            770                775                780
            Pro Lys Ser Tyr Glu Asn Ile Trp Phe His Ser Arg Pro Gln Glu Thr
            785                790                795                800
            Phe Val Pro Gln Pro Pro Asn Gln Glu Asp Asp Cys Val Phe Gly Pro
                            805                810                815
            Pro Phe Asp Phe Pro Leu Phe Gln Gly Leu Gln Val His Gly Val Glu
                            820                825                830
            Glu Gln Gly Gly Phe
                            835

<210> SEQ ID NO 67
<211> LENGTH: 2583
<212> TYPE: DNA
<213> ORGANISM: Artificial
<220> FEATURE:
<223> OTHER INFORMATION: Chimera protein

<400> SEQUENCE: 67
atgcgacctt ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca tttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caatgtggag    480
agcatccagt ggcgggacat agtcagcagt gactttctca gcaacatgtc gatggacttc    540
cagaaccacc tgggcagctg ccaaaagtgt gatccaagct gtcccaatgg agctgctggg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720 acaggcccc gggagagcga ctgcctggtc tgccgcaaat tccgagacga agccacgtgc    780
aaggacacct gccccccact catgctctac aaccccacca cgtaccagat ggatgtgaac    840
```

```
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggcctttgcc gcaaagtgtg taacggaata   1020
ggtattggtg aatttaaaga ctcactctcc ataaatgcta cgaatattaa acacttcaaa    1080
aactgcacct ccatcagtgg cgatctccac atcctgccgg tggcatttag gggtgactcc    1140
ttcacacata ctcctcctct ggatccacag gaactggata ttctgaaaac cgtaaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg gaaaaaactg    1440
tttgggacct ccggtcagaa aaccaaaatt ataagcaaca gaggtgaaaa cagctgcaag    1500
gccacaggcc aggtctgcca tgccttgtgc tcccccgagg gctgctgggg cccggagccc    1560
agggactgcg tctcttgccg gaatgtcagc cgaggcaggg aatgcgtgga caagtgcaac    1620
cttctggagg gtgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggccccac tgcgtcaaga cctgcccggc aggagtcatg    1800
ggagaaaaca cacccctggt ctggaagtac gcagacgccg ccatgtgtg ccacctgtgc    1860
catccaaact gcacctacgg atgcactggg ccaggtcttg aaggctgtcc aacgaatggg    1920
cctaagatcc cgtccgatcc atctgactta aacattttcc tggagatcct ttgcttagta    1980
ctcttgtcca ctacctgtgt agtgacctgg ctctgctgca aacgcagagg aaagacttcc    2040
ttctggtcag atgtgccaga cccagcccac agtagcctga gctcctggtt gcccaccatc    2100
atgacagagg aaaccttcca gttacccagc ttctgggact ccagcgtgcc atcaatcacc    2160
aagatcactg aactggagga agacaagaaa ccgaccccact gggattccga agctctgggg    2220
aatggtagcc ttccagcccct ggttcaggcc tatgtgctcc aaggagatcc aagagaaatt    2280
tccaaccagt cccagcctcc ctctcgcact ggtgaccagg tcctctatgg tcaggtgctt    2340
gagagcccca ccagcccagg agtaatgcag tacattcgct ctgactccac tcagcccctc    2400
ttgggggggcc ccaccctag ccctaaatct tatgaaaaca tctggttcca ttcaagaccc    2460
caggagacct tgtgccccca acctccaaac caggaagatg actgtgtctt tgggcctcca    2520
tttgattttc ccctctttca ggggctccag gtccatggag ttgaagaaca agggggtttc    2580
tag                                                                  2583
```

<210> SEQ ID NO 68
<211> LENGTH: 860
<212> TYPE: PRT
<213> ORGANISM: Artificial
<220> FEATURE:
<223> OTHER INFORMATION: Chimera protein

<400> SEQUENCE: 68

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

```
Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
```

```
            465                 470                 475                 480
        Phe Gly Thr Ser Gly Gln Lys Thr Lys Ile Ile Ser Asn Arg Gly Glu
                        485                 490                 495

Asn Ser Cys Lys Ala Thr Gly Gln Val Cys His Ala Leu Cys Ser Pro
                        500                 505                 510

Glu Gly Cys Trp Gly Pro Glu Pro Arg Asp Cys Val Ser Cys Arg Asn
                        515                 520                 525

Val Ser Arg Gly Arg Glu Cys Val Asp Lys Cys Asn Leu Leu Glu Gly
                        530                 535                 540

Glu Pro Arg Glu Phe Val Glu Asn Ser Glu Cys Ile Gln Cys His Pro
        545                 550                 555                 560

Glu Cys Leu Pro Gln Ala Met Asn Ile Thr Cys Thr Gly Arg Gly Pro
                        565                 570                 575

Asp Asn Cys Ile Gln Cys Ala His Tyr Ile Asp Gly Pro His Cys Val
                        580                 585                 590

Lys Thr Cys Pro Ala Gly Val Met Gly Glu Asn Asn Thr Leu Val Trp
                        595                 600                 605

Lys Tyr Ala Asp Ala Gly His Val Cys His Leu Cys His Pro Asn Cys
                        610                 615                 620

Thr Tyr Gly Cys Thr Gly Pro Gly Leu Glu Gly Cys Pro Thr Asn Gly
        625                 630                 635                 640

Pro Lys Ile Pro Ser Asp Pro Ser Asp Leu Asn Ile Phe Leu Glu Ile
                        645                 650                 655

Leu Cys Leu Val Leu Leu Ser Thr Thr Cys Val Val Thr Trp Leu Cys
                        660                 665                 670

Cys Lys Arg Arg Gly Lys Thr Ser Phe Trp Ser Asp Val Pro Asp Pro
                        675                 680                 685

Ala His Ser Ser Leu Ser Ser Trp Leu Pro Thr Ile Met Thr Glu Glu
                        690                 695                 700

Thr Phe Gln Leu Pro Ser Phe Trp Asp Ser Ser Val Pro Ser Ile Thr
        705                 710                 715                 720

Lys Ile Thr Glu Leu Glu Glu Asp Lys Lys Pro Thr His Trp Asp Ser
                        725                 730                 735

Glu Ser Ser Gly Asn Gly Ser Leu Pro Ala Leu Val Gln Ala Tyr Val
                        740                 745                 750

Leu Gln Gly Asp Pro Arg Glu Ile Ser Asn Gln Ser Gln Pro Pro Ser
                        755                 760                 765

Arg Thr Gly Asp Gln Val Leu Tyr Gly Gln Val Leu Glu Ser Pro Thr
                        770                 775                 780

Ser Pro Gly Val Met Gln Tyr Ile Arg Ser Asp Ser Thr Gln Pro Leu
        785                 790                 795                 800

Leu Gly Gly Pro Thr Pro Ser Pro Lys Ser Tyr Glu Asn Ile Trp Phe
                        805                 810                 815

His Ser Arg Pro Gln Glu Thr Phe Val Pro Gln Pro Asn Gln Glu
                        820                 825                 830

Asp Asp Cys Val Phe Gly Pro Pro Phe Asp Phe Pro Leu Phe Gln Gly
                        835                 840                 845

Leu Gln Val His Gly Val Glu Glu Gln Gly Phe
                        850                 855                 860

<210> SEQ ID NO 69
<211> LENGTH: 23
<212> TYPE: DNA
<213> ORGANISM: Artificial
```

```
<220> FEATURE:
<223> OTHER INFORMATION: PCR primer

<400> SEQUENCE: 69
gctcactgga tggtgggaag atg                                              23

<210> SEQ ID NO 70
<211> LENGTH: 21
<212> TYPE: DNA
<213> ORGANISM: Artificial
<220> FEATURE:
<223> OTHER INFORMATION: PCR primer

<400> SEQUENCE: 70
gggccagtgg atagacagat g                                                21

<210> SEQ ID NO 71
<211> LENGTH: 24
<212> TYPE: DNA
<213> ORGANISM: Artificial
<220> FEATURE:
<223> OTHER INFORMATION: PCR primer

<400> SEQUENCE: 71 cagggccag tggatagacc gatg                                              24

<210> SEQ ID NO 72
<211> LENGTH: 31
<212> TYPE: DNA
<213> ORGANISM: Artificial
<220> FEATURE:
<223> OTHER INFORMATION: PCR primer

<400> SEQUENCE: 72
gttaagcttc caccatgcga ccctccggga c                                     31

<210> SEQ ID NO 73
<211> LENGTH: 35
<212> TYPE: DNA
<213> ORGANISM: Artificial
<220> FEATURE:
<223> OTHER INFORMATION: PCR primer

<400> SEQUENCE: 73
gttggtgacc gacgggatct taggcccatt cgttg                                 35

<210> SEQ ID NO 74
<211> LENGTH: 1146
<212> TYPE: DNA
<213> ORGANISM: Artificial
<220> FEATURE:
<223> OTHER INFORMATION: Chimera protein

<400> SEQUENCE: 74
atgaagctgc tgccgtcggt ggtgctgaag ctctttctgg ctgcagttct ctcggcactg      60
gtgactggcg agagcctgga gcggcttcgg agagggctag ctgctggaac cagcaacccg     120
gaccctccca ctgtatccac ggaccagctg ctaccctag gaggcggccg ggaccggaaa      180
gtccgtgact gcaagaggc agatctggac cttttgagag tcactttatc ctccaagcca      240
caagcactgg ccacaccaaa caaggaggag cacgggaaaa gaaagaagaa aggcaagggg     300
ctagggaaga gagggaccc atgtcttcgg aaatacaagg acttctgcat ccatggagaa      360
tgcaaatatg tgaaggagct ccgggctccc tcctgcatct gccaccccggg ttaccatgga     420
```

-continued

```
gagaggtgtc atgggctgag cctcgaacct cgcggaccga caatcaagcc ctgtcctcca    480
tgcaaatgcc cagcacctaa cctcttgggt ggaccatccg tcttcatctt ccctccaaag    540
atcaaggatg tactcatgat ctccctgagc cccatagtca catgtgtggt ggtggatgtg    600
agcgaggatg acccagatgt ccagatcagc tggtttgtga acaacgtgga agtacacaca    660
gctcagacac aaacccatag agaggattac aacagtactc tccgggtggt cagtgccctc    720
cccatccagc accaggactg gatgagtggc aaggagttca atgcaaggt caacaacaaa     780 gacctgccag cgcccatcga gaaccatc tcaaaaccca aagggtcagt aagagctcca      840
caggtatatg tcttgcctcc accagaagaa gagatgacta gaaacaggt cactctgacc     900 tgcatggtca cagacttcat gcctgaagac atttacgtgg agtggaccaa caacgggaaa   960
acagagctaa actacaagaa cactgaacca gtcctggact ctgatggttc ttacttcatg   1020
tacagcaagc tgagagtgga aagaagaac tgggtggaaa gaaatagcta ctcctgttca    1080
gtggtccacg agggtctgca caatcaccac acgactaaga gcttctcccg gactccgggt   1140
aaatga                                                               1146
```

<210> SEQ ID NO 75
<211> LENGTH: 381
<212> TYPE: PRT
<213> ORGANISM: Artificial
<220> FEATURE:
<223> OTHER INFORMATION: Chimera protein

<400> SEQUENCE: 75

```
Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Glu Pro Arg Gly Pro Thr Ile Lys Pro Cys Pro Pro
145                 150                 155                 160

Cys Lys Cys Pro Ala Pro Asn Leu Leu Gly Gly Pro Ser Val Phe Ile
                165                 170                 175

Phe Pro Pro Lys Ile Lys Asp Val Leu Met Ile Ser Leu Ser Pro Ile
            180                 185                 190

Val Thr Cys Val Val Asp Val Ser Glu Asp Asp Pro Asp Val Gln
        195                 200                 205

Ile Ser Trp Phe Val Asn Asn Val Glu Val His Thr Ala Gln Thr Gln
    210                 215                 220

Thr His Arg Glu Asp Tyr Asn Ser Thr Leu Arg Val Val Ser Ala Leu
```

```
                225                 230                 235                 240

Pro Ile Gln His Gln Asp Trp Met Ser Gly Lys Glu Phe Lys Cys Lys
                245                 250                 255

Val Asn Asn Lys Asp Leu Pro Ala Pro Ile Glu Arg Thr Ile Ser Lys
                260                 265                 270

Pro Lys Gly Ser Val Arg Ala Pro Gln Val Tyr Val Leu Pro Pro Pro
                275                 280                 285

Glu Glu Glu Met Thr Lys Lys Gln Val Thr Leu Thr Cys Met Val Thr
                290                 295                 300

Asp Phe Met Pro Glu Asp Ile Tyr Val Glu Trp Thr Asn Asn Gly Lys
305                 310                 315                 320

Thr Glu Leu Asn Tyr Lys Asn Thr Glu Pro Val Leu Asp Ser Asp Gly
                325                 330                 335

Ser Tyr Phe Met Tyr Ser Lys Leu Arg Val Glu Lys Lys Asn Trp Val
                340                 345                 350

Glu Arg Asn Ser Tyr Ser Cys Ser Val Val His Glu Gly Leu His Asn
                355                 360                 365

His His Thr Thr Lys Ser Phe Ser Arg Thr Pro Gly Lys
                370                 375                 380

<210> SEQ ID NO 76
<211> LENGTH: 5
<212> TYPE: PRT
<213> ORGANISM: Mus musculus

<400> SEQUENCE: 76

Asp Tyr Tyr Met Asn
1               5

<210> SEQ ID NO 77
<211> LENGTH: 17
<212> TYPE: PRT
<213> ORGANISM: Mus musculus

<400> SEQUENCE: 77

Arg Val Asn Pro Asn Asn Gly Gly Thr Ser Tyr Ser Gln Lys Phe Lys
1               5                   10                  15

Asp

<210> SEQ ID NO 78
<211> LENGTH: 7
<212> TYPE: PRT
<213> ORGANISM: Mus musculus

<400> SEQUENCE: 78

Ile Tyr Tyr Gly Gly Ser Asp
1               5

<210> SEQ ID NO 79
<211> LENGTH: 16
<212> TYPE: PRT
<213> ORGANISM: Mus musculus

<400> SEQUENCE: 79

Lys Ser Ser Gln Ser Leu Leu Tyr Thr Thr Gly Lys Thr Tyr Leu Asn
1               5                   10                  15

<210> SEQ ID NO 80
<211> LENGTH: 7
<212> TYPE: PRT
```

<210> SEQ ID NO 80
<211> LENGTH: 6
<212> TYPE: PRT
<213> ORGANISM: Mus musculus

<400> SEQUENCE: 80

Gln Val Ser Lys Leu Val Pro
1               5

<210> SEQ ID NO 81
<211> LENGTH: 9
<212> TYPE: PRT
<213> ORGANISM: Mus musculus

<400> SEQUENCE: 81

Leu Gln Gly Thr Tyr Tyr Pro His Thr
1               5

<210> SEQ ID NO 82
<211> LENGTH: 11
<212> TYPE: PRT
<213> ORGANISM: Mus musculus

<400> SEQUENCE: 82

Ala Ser Ser Ser Val Ser Ser Met Tyr Leu His
1               5                   10

<210> SEQ ID NO 83
<211> LENGTH: 7
<212> TYPE: PRT
<213> ORGANISM: Mus musculus

<400> SEQUENCE: 83

Gly Thr Ser Asn Leu Ala Ser
1               5

<210> SEQ ID NO 84
<211> LENGTH: 9
<212> TYPE: PRT
<213> ORGANISM: Mus musculus

<400> SEQUENCE: 84

Gln Gln Tyr His Ser Asp Pro Phe Thr
1               5

<210> SEQ ID NO 85
<211> LENGTH: 444
<212> TYPE: DNA
<213> ORGANISM: Mus musculus

<400> SEQUENCE: 85

```
atgtcctctc cacagacact gaacacactg actctaaaca tgggatggag ctgggtcttt      60
ctcttcctcc tgtcaggaac tgcaggtgtc cactctgagg tccagctgca acagtctgga     120
cctgagctga tgaagcctgg ggcttcagtg aagatgtcct gtaaggcttc tggatacatt     180
ttcactgact attacatgaa ctgggtgaag cagagtcatg gaaagagcct tgaatggatt     240
ggacgtgtta atcctaacaa tggtggaact agctacagcc agaagttcaa ggacaaggcc     300
acattgacag tagacaaatc cctcaacaca gcctacatgc aggtcaacag cctgacatct     360
gaggactctg cggtctatta ctgtgcaaga atctactatg gtggttcgga ctggggccaa     420
ggcaccactc tcacagtctc ctca                                            444
```

<210> SEQ ID NO 86
<211> LENGTH: 148
<212> TYPE: PRT

<213> ORGANISM: Mus musculus

<400> SEQUENCE: 86

Met Ser Ser Pro Gln Thr Leu Asn Thr Leu Thr Leu Asn Met Gly Trp
1               5                   10                  15

Ser Trp Val Phe Leu Phe Leu Leu Ser Gly Thr Ala Gly Val His Ser
            20                  25                  30

Glu Val Gln Leu Gln Gln Ser Gly Pro Glu Leu Met Lys Pro Gly Ala
        35                  40                  45

Ser Val Lys Met Ser Cys Lys Ala Ser Gly Tyr Ile Phe Thr Asp Tyr
    50                  55                  60

Tyr Met Asn Trp Val Lys Gln Ser His Gly Lys Ser Leu Glu Trp Ile
65                  70                  75                  80

Gly Arg Val Asn Pro Asn Asn Gly Gly Thr Ser Tyr Ser Gln Lys Phe
                85                  90                  95

Lys Asp Lys Ala Thr Leu Thr Val Asp Lys Ser Leu Asn Thr Ala Tyr
            100                 105                 110

Met Gln Val Asn Ser Leu Thr Ser Glu Asp Ser Ala Val Tyr Tyr Cys
        115                 120                 125

Ala Arg Ile Tyr Tyr Gly Gly Ser Asp Trp Gly Gln Gly Thr Thr Leu
    130                 135                 140

Thr Val Ser Ser
145

<210> SEQ ID NO 87
<211> LENGTH: 396
<212> TYPE: DNA
<213> ORGANISM: Mus musculus

<400> SEQUENCE: 87
atgatgagtc ctgtccagtt cctgtttctg ttaatgctct ggattcagga atccaacggt      60
gagattgtga tgacccagac tccactgtct ttgtcggtta ccattggaca accagcctct     120
atctcttgca agtcaagtca gagcctctta tatactactg gaaagacata tttgaattgg     180
ttacaacaga ggcctggcca ggctccaaaa cacctgatgt atcaggtgtc caaactggtc     240
cctggcatcc ctgacaggtt cagtggcagt ggatcagaaa cagattttac acttaaaatc     300
agcagagtgg aggctgaaga tttgggagtt tattactgct tgcaaggtac atattatcct     360
catacgttcg gatcggggac caagctggaa ataaaa                               396

<210> SEQ ID NO 88
<211> LENGTH: 132
<212> TYPE: PRT
<213> ORGANISM: Mus musculus

<400> SEQUENCE: 88

Met Met Ser Pro Val Gln Phe Leu Phe Leu Leu Met Leu Trp Ile Gln
1               5                   10                  15

Glu Ser Asn Gly Glu Ile Val Met Thr Gln Thr Pro Leu Ser Leu Ser
            20                  25                  30

Val Thr Ile Gly Gln Pro Ala Ser Ile Ser Cys Lys Ser Ser Gln Ser
        35                  40                  45

Leu Leu Tyr Thr Thr Gly Lys Thr Tyr Leu Asn Trp Leu Gln Gln Arg
    50                  55                  60

Pro Gly Gln Ala Pro Lys His Leu Met Tyr Gln Val Ser Lys Leu Val
65                  70                  75                  80

```
Pro Gly Ile Pro Asp Arg Phe Ser Gly Ser Gly Ser Glu Thr Asp Phe
                85                  90                  95

Thr Leu Lys Ile Ser Arg Val Glu Ala Glu Asp Leu Gly Val Tyr Tyr
            100                 105                 110

Cys Leu Gln Gly Thr Tyr Tyr Pro His Thr Phe Gly Ser Gly Thr Lys
        115                 120                 125

Leu Glu Ile Lys
    130

<210> SEQ ID NO 89
<211> LENGTH: 390
<212> TYPE: DNA
<213> ORGANISM: Mus musculus

<400> SEQUENCE: 89
atggattttc aagtgcagat tttcagcttc ttgctgatca gtgcctcagt cataatgacc      60
agaggacaaa atgttctcac ccagtctcca gcaatcatgt ctgcctctcc aggggagaag     120
gtcaccatga cctgcagtgc cagctcaagt gtaagttcca tgtacttgca ctggtaccag     180
cagaagtcag gagcctcccc caaactctgg atttatggca catccaacct ggcttctgga     240
gtccctactc gcctcagtgg cagtgggtct gggacctctt actctctcac aatcagcagc     300
gtggaggctg aaaatgctgc cacttattac tgccagcagt atcatagtga cccattcacg     360
ttcggcacgg ggacaaaatt ggaaataaaa                                      390

<210> SEQ ID NO 90
<211> LENGTH: 130
<212> TYPE: PRT
<213> ORGANISM: Mus musculus

<400> SEQUENCE: 90

Met Asp Phe Gln Val Gln Ile Phe Ser Phe Leu Leu Ile Ser Ala Ser
1               5                   10                  15

Val Ile Met Thr Arg Gly Gln Asn Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Ser Met Tyr Leu His Trp Tyr Gln Gln Lys Ser Gly
    50                  55                  60

Ala Ser Pro Lys Leu Trp Ile Tyr Gly Thr Ser Asn Leu Ala Ser Gly
65                  70                  75                  80

Val Pro Thr Arg Leu Ser Gly Ser Gly Ser Gly Thr Ser Tyr Ser Leu
                85                  90                  95

Thr Ile Ser Ser Val Glu Ala Glu Asn Ala Ala Thr Tyr Tyr Cys Gln
            100                 105                 110

Gln Tyr His Ser Asp Pro Phe Thr Phe Gly Thr Gly Thr Lys Leu Glu
        115                 120                 125

Ile Lys
    130

<210> SEQ ID NO 91
<211> LENGTH: 34
<212> TYPE: DNA
<213> ORGANISM: Artificial
<220> FEATURE:
<223> OTHER INFORMATION: PCR primer

<400> SEQUENCE: 91
```
tccgaattcc accatgaagc tgctgccgtc ggtg                34

<210> SEQ ID NO 92
<211> LENGTH: 34
<212> TYPE: DNA
<213> ORGANISM: Artificial
<220> FEATURE:
<223> OTHER INFORMATION: PCR primer

<400> SEQUENCE: 92
tttgcggccg ctagaggctc agcccatgac acct                34

<210> SEQ ID NO 93
<211> LENGTH: 25
<212> TYPE: DNA
<213> ORGANISM: Artificial
<220> FEATURE:
<223> OTHER INFORMATION: PCR primer

<400> SEQUENCE: 93
ctgggtcttt ctcttcctcc tgtca                25

<210> SEQ ID NO 94
<211> LENGTH: 25
<212> TYPE: DNA
<213> ORGANISM: Artificial
<220> FEATURE:
<223> OTHER INFORMATION: PCR primer

<400> SEQUENCE: 94
tgagattgtg atgacccaga ctcca                25

<210> SEQ ID NO 95
<211> LENGTH: 24
<212> TYPE: DNA
<213> ORGANISM: Artificial
<220> FEATURE:
<223> OTHER INFORMATION: PCR primer

<400> SEQUENCE: 95
ttctcaccca gtctccagca atca                24

<210> SEQ ID NO 96
<211> LENGTH: 31
<212> TYPE: DNA
<213> ORGANISM: Artificial
<220> FEATURE:
<223> OTHER INFORMATION: PCR primer

<400> SEQUENCE: 96
ttggatccgt cactttatcc tccaagccac a                31

<210> SEQ ID NO 97
<211> LENGTH: 29
<212> TYPE: DNA
<213> ORGANISM: Artificial
<220> FEATURE:
<223> OTHER INFORMATION: PCR primer

<400> SEQUENCE: 97
ttctcgagga ggctcagccc atgacacct                29

<210> SEQ ID NO 98
<211> LENGTH: 29
<212> TYPE: DNA
<213> ORGANISM: Artificial

<220> FEATURE:
<223> OTHER INFORMATION: PCR primer

<400> SEQUENCE: 98
ttctcgagcc gaagacatgg gtccctctt                                29

<210> SEQ ID NO 99
<211> LENGTH: 29
<212> TYPE: DNA
<213> ORGANISM: Artificial
<220> FEATURE:
<223> OTHER INFORMATION: PCR primer

<400> SEQUENCE: 99
taggatccaa gagggaccca tgtcttcgg                                29

<210> SEQ ID NO 100
<211> LENGTH: 66
<212> TYPE: DNA
<213> ORGANISM: Artificial
<220> FEATURE:
<223> OTHER INFORMATION: PCR primer

<400> SEQUENCE: 100
gatccaagag ggacccatgt cttcggaaat acaaggactt ctgcatccat ggagaatgca    60
aatatc                                                              66

<210> SEQ ID NO 101
<211> LENGTH: 66
<212> TYPE: DNA
<213> ORGANISM: Artificial
<220> FEATURE:
<223> OTHER INFORMATION: Chimera protein

<400> SEQUENCE: 101
tcgagatatt tgcattctcc atggatgcag aagtccttgt atttccgaag acatgggtcc    60
ctcttg                                                              66

<210> SEQ ID NO 102
<211> LENGTH: 69
<212> TYPE: DNA
<213> ORGANISM: Artificial
<220> FEATURE:
<223> OTHER INFORMATION: Chimera protein

<400> SEQUENCE: 102
gatcctgcat ccatggagaa tgcaaatatg tgaaggagct ccgggctccc tcctgcatct    60
gccacccgc                                                           69

<210> SEQ ID NO 103
<211> LENGTH: 69
<212> TYPE: DNA
<213> ORGANISM: Artificial
<220> FEATURE:
<223> OTHER INFORMATION: Chimera protein

<400> SEQUENCE: 103
tcgagcgggt ggcagatgca ggagggagcc cggagctcct tcacatattt gcattctcca    60
tggatgcag                                                           69

<210> SEQ ID NO 104
<211> LENGTH: 66
<212> TYPE: DNA

```
<213> ORGANISM: Artificial
<220> FEATURE:
<223> OTHER INFORMATION: Chimera protein

<400> SEQUENCE: 104
gatccgctcc ctcctgcatc tgccacccgg gttaccatgg agagaggtgt catgggctga      60
gcctcc                                                                66

<210> SEQ ID NO 105
<211> LENGTH: 66
<212> TYPE: DNA
<213> ORGANISM: Artificial
<220> FEATURE:
<223> OTHER INFORMATION: Chimera protein

<400> SEQUENCE: 105
tcgaggaggc tcagcccatg acacctctct ccatggtaac ccgggtggca gatgcaggag      60
ggagcg                                                                66
```